US012780993B2

(12) United States Patent
Abe et al.

(10) Patent No.: US 12,780,993 B2
(45) Date of Patent: Nov. 3, 2026

(54) CROSSLINKED ORGANIC SILICON RESIN, A METHOD FOR PREPARING THE SAME, AND A COSMETIC

(71) Applicant: Shin-Etsu Chemical Co., Ltd., Tokyo (JP)

(72) Inventors: Takuya Abe, Annaka (JP); Masayuki Konishi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 471 days.

(21) Appl. No.: 18/576,768

(22) PCT Filed: Jun. 21, 2022

(86) PCT No.: PCT/JP2022/024692
§ 371 (c)(1),
(2) Date: Jan. 5, 2024

(87) PCT Pub. No.: WO2023/282052
PCT Pub. Date: Jan. 12, 2023

(65) Prior Publication Data

US 2024/0384039 A1 Nov. 21, 2024

(30) Foreign Application Priority Data

Jul. 9, 2021 (JP) ................................ 2021-114401

(51) Int. Cl.
*C08G 77/46* (2006.01)
*A61K 8/06* (2006.01)
(Continued)

(52) U.S. Cl.
CPC ................ *C08G 77/46* (2013.01); *A61K 8/06* (2013.01); *A61K 8/894* (2013.01); *A61Q 1/00* (2013.01); *A61Q 17/04* (2013.01)

(58) Field of Classification Search
CPC .......... C08G 77/46; A61K 8/06; A61K 8/894; A61Q 1/00; A61Q 17/04
See application file for complete search history.

(56) References Cited

U.S. PATENT DOCUMENTS 5,412,004 A 5/1995 Tachibana et al.
2002/0114771 A1 8/2002 Nakanishi
(Continued)

FOREIGN PATENT DOCUMENTS

JP S61293903 A 12/1986
JP H05140320 A 6/1993
JP 2001002520 A 1/2001
JP 2001002521 A 1/2001
JP 2002179548 A 6/2002
JP 2005089340 A 4/2005
JP 2010532413 A 10/2010
JP 2010540721 A 12/2010
JP 2015067654 A 4/2015
JP 2019085388 A 6/2019
JP 2021070719 A 5/2021
WO 2017169278 A1 10/2017
WO 2019107497 A1 6/2019

OTHER PUBLICATIONS

Extended European Search Report corresponding to European Patent Application No. 22837469.0 (6 pages) (dated Jun. 3, 2025).
(Continued)

*Primary Examiner* — Jiangtian Xu
(74) *Attorney, Agent, or Firm* — Myers Bigel, P.A.

(57) ABSTRACT

[Problem]

A purpose of the present invention is to provide a crosslinked organic silicon resin that can be dissolved in an oil agent that is liquid at room temperature, the crosslinked organic silicon resin becoming liquid, gum, or solid at room temperature when the oil agent is volatilized; and a method for preparing the same. Another purpose is to provide a cosmetic having exceptional applicability and richness and an excellent feeling on use, the cosmetic forming an emulsified product having a high-water content, freshness, and excellent stability over time, and to provide a crosslinked organic silicon resin that is capable of imparting a sunscreen effect and is less likely to form white residue or cause whitening in cosmetics that contain a UV scattering agent.

[Solution]

The present invention provides a crosslinked organic silicon resin represented by the average composition formula (1) and the method for preparing the same, wherein $R^1$ is, independently of each other, unsubstituted or substituted, an alkyl group having 1 to 30 carbon atoms, an aryl group having 6 to 30 carbon atoms, or an aralkyl group having 7 to 30 carbon atoms, $R^2$ is, independently of each other, a polyoxyalkylene-containing group, a polyhydric alcohol-containing hydrocarbon group having two or more hydroxyl groups and/or alkoxy groups, or a group selected from the groups for $R^1$, one or more of $R^2$ in each $R^2_3SiO_{1/2}$ unit are a polyoxyalkylene-containing group or a polyhydric alcohol-containing hydrocarbon group having two or more hydroxyl groups and/or alkoxy groups, $R^3$ is, independently of each other, an organopolysiloxane-containing group or a group selected from the groups for $R^1$, each $R^3_3SiO_{1/2}$ unit has one or more organopolysiloxane-containing group, X is a divalent polyoxyalkylene-containing group represented by the formula (2) or a divalent group represented by the following formula (3), some of $R^2$, $R^3$ and X are optionally a hydroxyl group, a1, a2, a3, a4, b, c and d are numbers satisfying equations $0<a1\leq400$, $0\leq a2\leq200$, $0\leq a3\leq400$, $0<a4\leq50$, $0\leq b\leq320$, $0\leq c\leq320$, $0<d\leq1000$, and $0.5\leq(a1+a2+a3+a4)/(c+d)\leq1.5$, and p is a number satisfying $1\leq p\leq3$.

22 Claims, No Drawings

(51) Int. Cl.

| | |
|---|---|
| ***A61K 8/894*** | (2006.01) |
| ***A61Q 1/00*** | (2006.01) |
| ***A61Q 17/04*** | (2006.01) |

(56) References Cited

U.S. PATENT DOCUMENTS

| | | | | |
|---|---|---|---|---|
| 2003/0064046 | A1 | 4/2003 | Omura et al. | |
| 2003/0198869 | A1 | 10/2003 | West et al. | |
| 2010/0247460 | A1 | 9/2010 | Lin et al. | |
| 2010/0330011 | A1 | 12/2010 | Kennan et al. | |
| 2018/0265642 | A1 | 9/2018 | Abe et al. | |
| 2019/0077920 | A1 | 3/2019 | Kamei | |
| 2020/0332065 | A1* | 10/2020 | Abe ..................... | C08K 5/5425 |
| 2024/0166888 | A1 | 5/2024 | Goto | |

OTHER PUBLICATIONS

English translation of International Search Report corresponding to International Patent Application No. PCT/JP2022/024692 (3 pages) (mailed Jul. 26, 2022).

* cited by examiner

CROSSLINKED ORGANIC SILICON RESIN, A METHOD FOR PREPARING THE SAME, AND A COSMETIC

TECHNICAL FIELD

The present invention relates to a crosslinked organic silicon resin. Specifically, the present invention relates to a novel crosslinked organic silicon resin and a cosmetic containing the same.

BACKGROUND OF THE INVENTION

Conventionally, cosmetics have contained silicone oil to increase water repellency in order to maintain protective effects on skin. In water-in-oil emulsion compositions, silicone oil is used as an oil agent to yield refreshing, non-sticky, and favorable water repellent properties. It is known that in water-in-oil emulsions containing silicone oil, in order to obtain water-in-oil cosmetics with refreshing textures, emulsions with high water content and large particle diameters can be produced using crosslinked silicone activators to obtain cosmetics that provide a refreshing feeling on use (Patent Literatures 1 and 2). However, these crosslinked silicone activators lack the ability to decrease interfacial tension and are difficult to stabilize by themselves.

For water-in-oil emulsions containing the silicone oil, a technique for preparing water-in-oil emulsions using emulsifiers such as polyoxyalkylene-modified organopolysiloxane (Patent Literature 3) and a technique for using silicone-branched polyether-modified silicone with a further increased compatibility with silicone (Patent Literature 4) are known, providing better penetration into the skin and a refreshing feeling on use. However, it is difficult to produce emulsions with high water content using these linear silicone activators alone. If an emulsion a high amount of linear silicone activators for stabilization, it is difficult to produce a refreshing feeling on use, and although the obtained emulsion sits well on the skin, it lasts for a short period and has a light texture, resulting in a lack of richness. Further, problems such as whitening occur in cosmetics that contain a UV scattering agent.

Moreover, it is known that emulsions with a high internal aqueous phase and good stability over time can be obtained using a polyether-modified organic silicon resin (Patent Literature 5). However, the emulsion lacks interface stabilization and is difficult to stabilize by itself.

PRIOR LITERATURES

Patent Literatures

Patent Literature 1: Japanese Patent Application Laid-Open No. 2001-2521

Patent Literature 2: Japanese Patent Application Laid-Open No. 1993-140320

Patent Literature 3: Japanese Patent Application Laid-Open No. S61-293903/1986

Patent Literature 4: Japanese Patent Application Laid-Open No. 2002-179548

Patent Literature 5: Japanese Patent Application Laid-Open No. 2019-085388

DISCLOSURE OF THE INVENTION

Problems to be Solved by the Invention

The present invention has been made considering the above circumstances. A purpose of the present invention is to provide a crosslinked organic silicon resin that can be dissolved in an oil agent that is liquid at room temperature, the crosslinked organic silicon resin becoming liquid, gum, or solid at room temperature when the oil agent is volatilized; and a method for preparing the same. Another purpose is to provide a cosmetic having exceptional applicability and richness and an excellent feeling on use, the cosmetic forming an emulsified product having a high-water content, freshness, and excellent stability over time, and to provide a crosslinked organic silicon resin that is capable of imparting a sunscreen effect and is less likely to form white residue or cause whitening in cosmetics that contain a UV scattering agent.

Solutions to the Problems

The present inventors conducted research diligently to achieve the above purposes, and found that on account of specifying the amount of hydrosilyl groups in the hydrosilyl group-containing organic silicon resin, which is an ingredient of the crosslinked organic silicon resin, and specifying the amount of polyoxyalkylene having alkenyl groups at both ends or polyhydric alcohol-substituted hydrocarbons having at least two hydroxyl groups, which are crosslinking agents, the obtained crosslinked organic silicon resin dissolves in an oil agent that is liquid at room temperature and becomes liquid, gum, or solid at room temperature when the oil agent is volatilized.

The present inventors further found that on account of limiting the amount of organopolysiloxane, which is a modifying agent in the ingredients, and on account of limiting the chain length of polyoxyalkylene having alkenyl groups at both ends or polyhydric alcohol-substituted hydrocarbons having two or more hydroxyl groups, which are crosslinking agents in the ingredients, the obtained crosslinked organic silicon resin ranges from being liquid to gum at room temperature and that the above purposes are achievable, and resulting in the present invention.

That is, the present invention provides a crosslinked organic silicon resin represented by the following average composition formula (1) and the method for preparing the same.

$$(R^1_3SiO_{1/2})_{a1}(R^2_3SiO_{1/2})_{a2}(R^3_3SiO_{1/2})_{a3}(R^1_{3-p}(X_{1/2})_p SiO_{1/2})_{a4}(R^1_2SiO_{2/2})_b(R^1SiO_{3/2})_c(SiO_{4/2})_d \quad (1)$$

wherein $R^1$ is, independently of each other, unsubstituted or substituted, an alkyl group having 1 to 30 carbon atoms, an aryl group having 6 to 30 carbon atoms, or an aralkyl group having 7 to 30 carbon atoms, $R^2$ is, independently of each other, a polyoxyalkylene-containing group, a polyhydric alcohol-containing hydrocarbon group having two or more hydroxyl groups and/or alkoxy groups, or a group selected from the groups for $R^1$, one or more of $R^2$ in each $R^2_3SiO_{1/2}$ unit are a polyoxyalkylene-containing group or a polyhydric alcohol-containing hydrocarbon group having two or more hydroxyl groups and/or alkoxy groups, $R^3$ is, independently of each other, an organopolysiloxane-containing group or a group selected from the groups for $R^1$, each $R^3_3SiO_{1/2}$ unit has one or more organopolysiloxane-containing group, X is a divalent polyoxyalkylene-containing group represented by the following formula (2) or a divalent group represented by the following formula (3), some of $R^2$, $R^3$ and X are optionally a hydroxyl group, $$-Y^1-O-(C_2H_4O)_{e1}(C_3H_6O)_{e2}(C_4H_8O)_{e3}-Y^1- \quad (2)$$

wherein e1, e2, and e3 are numbers satisfying the equations $0 \le e1 \le 200$, $0 \le e2 < 200$, $0 \le e3 < 200$, and $0 < e1+e2+e3 \le 200$, and $Y^1$ is a hydrocarbon group having 3 to 20 carbon atoms, optionally having an ether bond or an ester bond or both, and $Y^1$ bonds to a silicon atom in the formula (1).

$$-Y^1-O-Q^1-Y^1- \quad (3)$$

wherein $Y^1$ is a hydrocarbon group having 3 to 20 carbon atoms, optionally having an ether bond or an ester bond or both, and $Y^1$ bonds to a silicon atom in the formula (1), and $Q^1$ is a polyhydric alcohol-containing hydrocarbon group having 3 to 20 carbon atoms and having two or more hydroxyl groups and/or alkoxy groups, a1, a2, a3, a4, b, c and d are numbers satisfying equations $0 < a1 \le 400$, $0 \le a2 \le 200$, $0 \le a3 \le 400$, $0 < a4 < 50$, $0 \le b \le 320$, $0 \le c \le 320$, $0 < d \le 1000$, and $0.5 \le (a1+a2+a3+a4)/(c+d) \le 1.5$, and p is a number satisfying $1 \le p \le 31$.

The present invention further provides a method for preparing a crosslinked organic silicon resin represented by the formula (1).

Preferably, by specifying the degree of crosslinking in the crosslinked organic silicon resin of the present invention, the crosslinked organic silicon resin can be made liquid. Thus, it is not necessary to dissolve the crosslinked organic silicon resin in an oil agent that is liquid at room temperature, and the crosslinked organic silicon resin is easy to use. The crosslinked organic silicon resin of the present invention has surface activity, and when included in a cosmetic as an emulsifier, it can yield a cosmetic with an exceptional texture and stability over time. The emulsion obtained by using the crosslinked organic silicon resin of the present invention as a water-in-oil emulsifier has a high-water content, large particle diameters, a refreshing and light texture, and exceptional stability over time, in comparison to the emulsion obtained by using a surfactant such as a linear polyether-modified organosiloxane. Preferably, by using a crosslinked organic silicon resin having a weight-average molecular weight of 40,000 to 1,000,000 as an emulsifier, an emulsion with an exceptional texture and emulsification stability can be provided even if the oil agent is a polar oil and is not particularly limited to silicone.

Effects of the Invention

The crosslinked organic silicon resin of the present invention has surface activity and can be included as an emulsifier in cosmetics. The crosslinked organic silicon resin is contained in cosmetics to provide an emulsion having exceptional applicability, richness, high water content, a refreshing feeling, and excellent stability over time, and provide a crosslinked organic silicon resin capable of imparting a sunscreen effect and is less likely to form white residue or cause whitening in cosmetics that contain a UV scattering agent, a method for preparing the same, and a cosmetic containing the crosslinked organic silicon resin.

DETAILED DESCRIPTION OF THE INVENTION

The following describes the present invention in detail.

The present invention is a crosslinked organic silicon resin represented by the average composition formula (1).

$$(R^1{}_3SiO_{1/2})_{a1}(R^2{}_3SiO_{1/2})_{a2}(R^3{}_3SiO_{1/2})_{a3}(R^1{}_{3-p}(X_{1/2})_p SiO_{1/2})_{a4}(R^1{}_2SiO_{2/2})_b(R^1SiO_{3/2})_c(SiO_{4/2})_d \quad (1)$$

[wherein $R^1$ is, independently of each other, unsubstituted or substituted, an alkyl group having 1 to 30 carbon atoms, an aryl group having 6 to 30 carbon atoms, or an aralkyl group having 7 to 30 carbon atoms, $R^2$ is, independently of each other, a polyoxyalkylene-containing group, a polyhydric alcohol-containing hydrocarbon group having two or more hydroxyl groups and/or alkoxy groups, or a group selected from groups for $R^1$, one or more $R^2$ in each $R^2{}_3SiO_{1/2}$ unit are a polyoxyalkylene-containing group or a polyhydric alcohol-containing hydrocarbon group having two or more hydroxyl groups and/or alkoxy groups, $R^3$ is, independently of each other, an organopolysiloxane-containing group or a group selected from groups for $R^1$, each $R^3{}_3SiO_{1/2}$ unit has one or more organopolysiloxane-containing groups, X is a divalent polyoxyalkylene-containing group represented by the following formula (2) or a divalent group represented by the following formula (3), and some of $R^2$, $R^3$ and X are optionally a hydroxyl group, $$-Y^1-O-(C_2H_4O)_{e1}(C_3H_6O)_{e2}(C_4H_8O)_{e3}-Y^1- \quad (2)$$

wherein e1, e2, and e3 are numbers satisfying the equations $0 \le e1 < 200$, $0 \le e2 < 200$, $0 \le e3 < 200$, and $0 < e1+e2+e3 \le 200$, and $Y^1$ is a hydrocarbon group having 3 to 20 carbon atoms, which may have an ether bond or an ester bond or both, and is bonded to a silicon atom in the formula (1).

$$-Y^1-O-Q^1-Y^1- \quad (3)$$

wherein $Y^1$ is a hydrocarbon group having 3 to 20 carbon atoms, which may have an ether bond or an ester bond or both, and is bonded to a silicon atom in the formula (1), and $Q^1$ is a polyhydric alcohol-containing hydrocarbon group having 3 to 20 carbon atoms and having two or more hydroxyl groups and/or alkoxy groups.

a1, a2, a3, a4, b, c and d are numbers satisfying equations $0 < a1 \le 400$, $0 \le a2 \le 200$, $0 \le a3 \le 400$, $0 < a4 \le 50$, $0 \le b \le 320$, $0 \le c \le 320$, $0 < d \le 1000$, and $0.5 \le (a1+a2+a3+a4)/(c+d) \le 1.5$, and p is a number satisfying the equation $1 \le p \le 3$].

In the formula (1), $R^1$ is, independently of each other, unsubstituted or substituted, an alkyl group having 1 to 30 carbon atoms, an aryl group having 6 to 30 carbon atoms, or an aralkyl group having 7 to 30 carbon atoms. $R^1$ is more preferably an alkyl group having 1 to 10 carbon atoms, an aryl group having 6 to 15 carbon atoms, or an aralkyl group having 7 to 16 carbon atoms. $R^1$ is more specifically a methyl group, an ethyl group, a propyl group, a butyl group, a pentyl group, a cyclopentyl group, a cyclohexyl group, a phenyl group, or a tolyl group. In particular, $R^1$ is preferably an alkyl group having 1 to 5 carbon atoms, a phenyl group, or a tolyl group.

In the formula (1), a1, a2, a3, a4, b, c and d are in the following ranges. a1 satisfies the equation $0<a1\leq400$, preferably the equation $1\leq a1\leq100$, or more preferably the equation $1\leq a1\leq50$. a2 satisfies the equation $0\leq a2\leq200$, preferably the equation $0\leq a2\leq100$, or more preferably the equation $0\leq a2\leq50$. a3 satisfies the equation $0\leq a3\leq400$, preferably the equation $1\leq a3\leq100$, or more preferably the equation $1\leq a3\leq50$. If a3 is larger than the upper limit, hydrophilicity becomes insufficient, resulting in weaker emulsification and a lack of stability. a4 satisfies the equation $0<a4\leq50$, preferably the equation $0<a4\leq30$, or more preferably the equation $0<a4\leq10$ or $0<a4\leq3.5$. If a4 is larger than the upper limit, the crosslinking degree and the molecular weight increase, resulting in a high possibility of gelation. b, c, and d satisfy the equations $0\leq b\leq320$, $0\leq c\leq320$, and $0<d\leq1{,}000$. d preferably satisfies the equation $1\leq d\leq300$, more preferably the equation $5\leq d\leq100$, or even more preferably the equation $10\leq d\leq55$. b preferably satisfies the equations $0\leq b\leq100$, $0\leq b\leq50$, and $0\leq b\leq10$, and c preferably satisfies the equations $0\leq c\leq100$, $0\leq c\leq50$, and $0\leq c\leq10$. a1, a2, a3, a4, c and d are numbers satisfying the equation $0.5\leq(a1+a2+a3+a4)/(c+d)\leq1.5$, preferably the equation $0.7\leq(a1+a2+a3+a4)/(c+d)\leq1.5$. If $(a1+a2+a3+a4)/(c+d)$ is smaller than the lower limit, the degree of crosslinking and the molecular weight increase, resulting in a gel. p is a number satisfying the equation $1\leq p\leq3$, preferably 1 or 2, or more preferably 1.

X is a divalent group represented by the following general formula (2) or (3).

$$-Y^1-O-(C_2H_4O)_{e1}(C_3H_6O)_{e2}(C_4H_8O)_{e3}-Y^1- \quad (2)$$

$$-Y^1-O-Q^1-Y^1- \quad (3)$$

Some of X may be optional hydroxyl groups, and X is a monovalent group in such a case.

In the formula (2), e1 satisfies the equation $0\leq e1<200$, preferably the equation $1\leq e1\leq100$, or more preferably the equations $2\leq e1\leq50$ and $3\leq e1\leq40$. If e1 is larger than the upper limit, hydrophilicity becomes too high, resulting in a lack of emulsification stability. e2 satisfies the equation $0\leq e2<200$, preferably the equations $0\leq e2\leq100$, $0\leq e2\leq50$, and $0\leq e2\leq30$. e2 is more preferably 0. When e2 is not 0, e2 is particularly preferable a number satisfying the equation $1\leq e2\leq10$. When e2 is larger than the upper limit, hydrophilicity becomes too high, resulting in a lack of emulsification stability. e3 satisfies the equation $0\leq e3<200$, preferably the equation $0\leq e3\leq100$, or more preferably the equations $0\leq e3\leq50$ and $0\leq e3\leq30$. e3 is more preferably 0. When e3 is not 0, e3 is particularly preferable a number satisfying the equation $1\leq e3\leq10$. If e3 is larger than the upper limit, hydrophilicity becomes too high, resulting in a lack of emulsification stability. The value of e1+e2+e3 satisfies the equation $0<e1+e2+e3<200$, preferably the equation $1\leq e1+e2+e3\leq100$, more preferably the equation $8\leq e1+e2+e3\leq50$, or even more preferably the equation $8<e1+e2+e3\leq40$. Alternatively, the value of e1+e2+e3 satisfies the equation $0<e1+e2+e3\leq40$. If the value of e1+e2+e3 is smaller than the lower limit, hydrophilicity becomes insufficient, resulting in weaker emulsification and a lack of stability. If the value of e1+e2+e3 is larger than the upper limit, hydrophilicity becomes too high, resulting in a lack of emulsification stability. In order to impart sufficient hydrophilicity to obtain a water-in-oil emulsion, the equation $e1/(e2+e3)\geq1$ is desirably satisfied, and in order to impart sufficient hydrophobicity to obtain an oil-in-water emulsion, the equation $e1/(e2+e3)\leq1$ is desirably satisfied. When the polyoxyalkylene moiety consists of two or more of an ethylene oxide unit, a propylene oxide unit, or a butylene oxide unit, it may be a block copolymer or a random copolymer of two or more of them.

In the formula (3), $Q^1$ is a group derived from polyhydric alcohols having two or more hydroxyl groups, such as polyglycerin, and is a polyhydric alcohol-containing hydrocarbon group having two or more hydroxyl groups and/or alkoxy groups and having 3 to 20 carbon atoms, preferably 3 to 12 carbon atoms. $Q^1$ preferably has at least one structure represented by $-CH_2CH(OR^4)CH_2O-$, wherein $R^4$ is an unsubstituted or substituted monovalent hydrocarbon group having 1 to 30 carbon atoms or a hydrogen atom.

More specifically, $Q^1$ is a combination of one or more selected from the group consisting of the following formulas (4), (5), (6), (7), (8), (9), and (10), and has at least the structure represented by the following formula (6). The oxygen atom (**) in each of the following formulas (4), (5), (6), (8), and (9) is bonded to the carbon atom (*) of one of the following formulas (4), (5), (6), (7), (8), (9), and (10). $Q^1$ has at least one of the following formulas (4), (5), (6), (8), and (9), and in each of the formulas, at least one oxygen atom (**) is bonded to $Y^1$, and at least one carbon atom (*) is bonded to the oxygen atom in the formula (3).

(4)

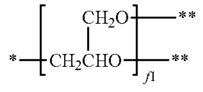

(5)

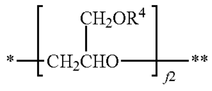

(6)

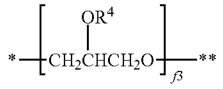

(7)

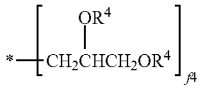

(8)

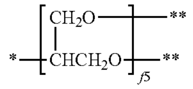

(9)

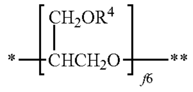

(10)

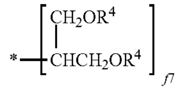

wherein $R^4$ is an unsubstituted or substituted monovalent hydrocarbon group having 1 to 30 carbon atoms or a hydrogen atom, and f1, f2, f3, f4, f5, f6, and f7 are integers satisfying the equations $0 \le f1 \le 20$, $0 \le f2 \le 20$, $0 < f3 \le 20$, $0 \le f4 < 20$, $0 \le f5 \le 20$, $0 \le f6 \le 20$, $0 \le f7 \le 20$, and the equation $1 \le f1+f2+f3+f4+f5+f6+f7 \le 20$.

In each unit, f1, f2, f3, f4, f5, f6, and f7 are integers satisfying the equations $0 \le f1 \le 20$, $0 \le f2 \le 20$, $0 < f3 \le 20$, $0 \le f4 \le 20$, $0 \le f5 \le 20$, $0 \le f6 \le 20$, and $0 \le f7 \le 20$. The average total number of bonds represented by F2 (f1+f2+f3+f4+f5+f6+f7) in the formulas (4), (5), (6), (7), (8), (9), and (10) satisfies the equation $1 \le F2 \le 20$, preferably the equation $1 \le F2 \le 10$, or more preferably the equation $1 \le F2 \le 5$. If F2 is larger than 20, hydrophilicity becomes too high, resulting in a lack of emulsification stability.

For example, the formula (3) is a divalent group which mainly has the following structure and may also have the structures of the formulas (4), (5), (7), (8), and (9) within the ranges described above.

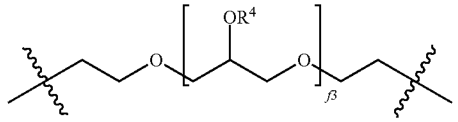

$(0 < f3 \le 20)$

For example, the formula (3) is a divalent group which mainly has the following structure and may also have the structures of the formulas (4), (7), (8), and (9) within the ranges described above.

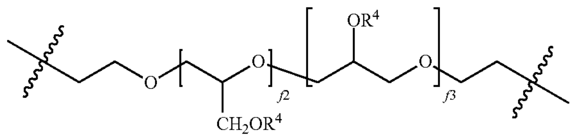

f2 and f3 satisfy the equations $0 \le f2 \le 20$ and $0 < f3 \le 20$, and the order of bonding of the repeating units is not limited to the above.

In the formula (1), $R^2$ is, independently of each other, a polyoxyalkylene-containing group, a polyhydric alcohol-containing hydrocarbon group having two or more hydroxyl groups and/or alkoxy groups, or a group selected from the groups for $R^1$, and one or more $R^2$ in each $R^2_3SiO_{1/2}$ unit are a polyoxyalkylene-containing group or a polyhydric alcohol-containing hydrocarbon group having two or more hydroxyl groups and/or alkoxy groups. $R^1$ is as defined above. Some of $R^2$ may be a hydroxyl group.

In $R^2$, the polyoxyalkylene-containing group is preferably represented by the following general formula (11).

$$—Y^1—O—(C_2H_4O)_{e4}(C_3H_6O)_{e5}(C_4H_8O)_{e6}R^4 \quad (11)$$

In the formula (11), $Y^1$ is a hydrocarbon group having 3 to 20 carbon atoms, which may have an ether bond or an ester bond or both, $R^4$ is an unsubstituted or substituted monovalent hydrocarbon group having 1 to 30 carbon atoms or a hydrogen atom, e4, e5, and e6 are a number satisfying the equations $0 \le e4 < 200$, $0 \le e5 < 200$, $0 \le e6 < 200$ and $0 < e4+e5+e6 \le 200$.

In the formula (11), e4 satisfies the equation $0 \le e4 < 200$, preferably the equation $1 \le e4 \le 100$ or $3 \le e4 \le 50$, more preferably the equation $4 \le e4 \le 30$, or even more preferably the equation $5 \le e4 \le 15$. If e4 is larger than the upper limit, hydrophilicity becomes too high, resulting in a lack of emulsification stability. e5 satisfies the equation $0 \le e5 < 200$, preferably $0 \le e5 \le 100$, more preferably $0 \le e5 \le 50$, or even more preferably $0 \le e5 \le 30$. e5 is still more preferably 0. When e5 is not 0, e5 is the number particularly preferable satisfying the equation $1 \le e5 \le 10$. If e5 is larger than the upper limit, hydrophilicity becomes too high, resulting in a lack of emulsification stability. e6 satisfies the equation $0 \le e6 < 200$, preferably $0 \le e6 \le 100$, more preferably $0 \le e6 \le 50$, or even more preferably $0 \le e6 \le 30$. e6 is still more preferably 0, and if it is not 0, e6 is the number particularly preferable satisfying the equation $1 \le e6 \le 10$. If e6 is larger than the upper limit, hydrophilicity becomes too high, resulting in a lack of emulsification stability. e4+e5+e6 satisfies the equation $0 < e4+e5+e6 < 200$, preferably the equation $1 \le e4+e5+e6 \le 100$, or more preferably the equation $5 \le e4+e5+e6 \le 50$. e4+e5+e6 is still more preferable such that it satisfies the equation $8 \le e4+e5+e6 \le 40$ or is even more preferable such that it satisfies the equation $8 \le e4+e5+e6 \le 20$. If e4+e5+e6 is smaller than the lower limit, hydrophilicity becomes insufficient, resulting in weaker emulsification and a lack of stability. If e4+e5+e6 is larger than the upper limit, hydrophilicity becomes too high, resulting in a lack of emulsification stability. In order to impart sufficient hydrophilicity to obtain a water-in-oil emulsion, the equation $e4/(e5+e6) \ge 1$ is desirably satisfied, and in order to impart sufficient hydrophobicity to obtain an oil-in-water emulsion, the equation $e4/(e5+e6) < 1$ is desirably satisfied. When the polyoxyalkylene moiety consists of two or more of an ethylene oxide unit, a propylene oxide unit, or a butylene oxide unit, it may be a block copolymer or a random copolymer of two or more of them.

In $R^2$, the polyhydric alcohol-containing hydrocarbon group having two or more hydroxyl groups and/or alkoxy groups is preferably represented by the following general formula (12).

$$—Y^1—O—Q^2 \quad (12)$$

In the formula (12), $Y^1$ is a hydrocarbon group having 3 to 20 carbon atoms, which may have an ether bond or an ester bond or both, and is bonded to a silicon atom in the formula (1). $Q^2$ is a polyhydric alcohol-containing hydrocarbon group having 3 to 20 carbon atoms, preferably 3 to 12 carbon atoms, and having two or more hydroxyl groups and/or alkoxy groups.

In the formula (12), $Q^2$ preferably has at least one structure represented by $—CH_2CH(OR^4)CH_2OR^4$, wherein $R^4$ is an unsubstituted or substituted monovalent hydrocarbon group having 1 to 30 carbon atoms or a hydrogen atom.

More specifically, $Q^2$ is a combination of one or more selected from the group consisting of the following formulas (13), (14), (15), (16), (17), (18), and (19), and has at least the structure represented by the following formula (16). The oxygen atom (**) in each of the following formulas (13), (14), (15), (17), and (18) is bonded to the carbon atom (*) of one of the following formulas (13), (14), (15), (16), (17), (18), and (19). $Q^2$ has at least one of the following formulas (16) and (19), and at least one carbon atom (*) in the formulas (16) and (19) is bonded to the oxygen atom in the formula (12).

(13)

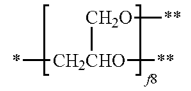

(14)

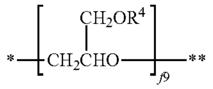

(15)

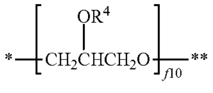

(16)

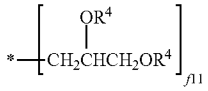

(17)

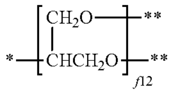

(18)

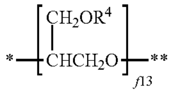

(19)

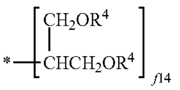

In the formulas (13) to (19), $R^4$ is an unsubstituted or substituted, monovalent hydrocarbon group having 1 to 30 carbon atoms or a hydrogen atom. f8, f9, f10, f11, f12, f13, and f14 are integers satisfying the equations $0 \le f8 \le 20$, $0 \le f9 \le 20$, $0 \le f10 \le 20$, $0 < f11 \le 20$, $0 \le f12 \le 20$, $0 \le f13 \le 20$, $0 \le f14 \le 20$, and $1 \le f8+f9+f10+f11+f12+f13+f14 \le 20$.

In each unit, f8, f9, f10, f11, f12, f13, and f14 are integers satisfying $0 \le f8 \le 20$, $0 \le f9 \le 20$, $0 \le f10 \le 20$, $0 < f11 \le 20$, $0 \le f12 \le 20$, $0 \le f13 \le 20$, and $0 \le f14 \le 20$, and the average total number of bonds represented by $F1(f8+f9+f10+f11+f12+f13+f14)$ in the formulas (13), (14), (15), (16), (17), (18), and (19) satisfies the equation $1 \le F1 \le 20$, preferably $1 \le F1 \le 10$, or more preferably $1 \le F1 \le 5$. If F1 is larger than 20, hydrophilicity becomes too high, resulting in a lack of emulsification stability.

For example, when $Q^2$ has units represented by the formulas (16) and (15), the formula (12) can be represented by the following structure.

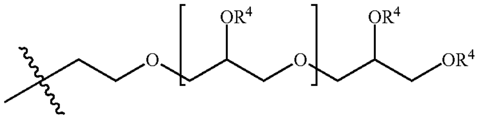

$(0 \leqq f10 \leqq 20)$

For example, when $Q^2$ has units represented by the formulas (16), (15), and (13), the formula (12) can be represented by the following structure.

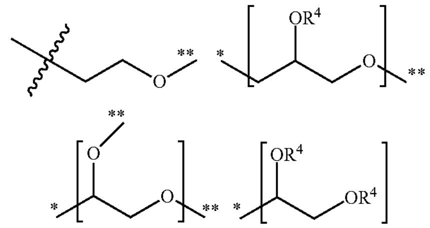

wherein f8 satisfies the equation $0 \le f8 \le 20$, f10 satisfies the equation $0 \le f10 \le 20$, f11 satisfies the equation $0 < f11 \le 20$, and the order of bonding of the repeating units is not limited to the above. The oxygen atom (**) is bonded to any of the carbon atoms (*).

In each formula, $R^4$ is, independently of each other, an unsubstituted or substituted monovalent hydrocarbon group having 1 to 30 carbon atoms or a hydrogen atom. Preferably, $R^4$ is a hydrogen atom, or an alkyl group having 1 to 10 carbon atoms or more preferably 1 to 5 carbon atoms. Examples of the alkyl group include a methyl group, an ethyl group, a propyl group, a butyl group, and a pentyl group. More preferably, $R^4$ is a hydrogen atom or a methyl group.

In each formula, $Y^1$ is a hydrocarbon group having 3 to 20 carbon atoms, which may have at least one of an ether bond or an ester bond. Examples of $Y^1$ include $-(CH_2)_2-$, $-(CH_2)_3-$, $-(CH_2)_4-$, $-CH_2CH(CH_3)\ CH_2-$, $-(CH_2)_8-$, $-(CH_2)_{11}-$, $-(CH_2)_3-O-(CH_2)_2-$, and $-(CH_2)_2-O-(CH_2)_3-$, and $Y^1$ is preferably $-(CH_2)_2-$, $-(CH_2)_3-$, or $-CH_2CH(CH_3)\ CH_2-$.

In $R^3$ in the formula (1), the organopolysiloxane-containing group is a group represented by the following general formula (20), (21), (22), or (23). In each $R^3{}_3SiO_{1/2}$ unit, one or more $R^3$ are a group represented by the following general formula (20), (21), (22), or (23). Some of $R^3$ may be a hydroxyl group.

$$-(CH_2)_2-C_nH_{2n}-(SiOR^1{}_2)_g-SiR^1{}_3 \tag{20}$$

$$-(CH_2)_2-C_nH_{2n}-SiR^1{}_{h1}-(OSiR^1{}_3)_{3-h1} \tag{21}$$

$$-(CH_2)_2-C_nH_{2n}-SiR^1{}_{h1}-(OSiR^1{}_{h2}(OSiR^1{}_3)_{3-h2})_{3-h1} \tag{22}$$

$$-(CH_2)_2-C_nH_{2n}-SiR^1{}_{h1}-(OSiR^1{}_{h2}(OSiR^1{}_{h3}(OSiR^1{}_3)_{3-h3})_{3-h2})_{3-h1} \tag{23}$$

In the formula, $R^1$ is as defined above, n and g are an integer satisfying the equations $0 \le n \le 5$ and $0 \le g \le 500$, and $h_1$ to $h_3$ are an integer of from 0 to 2.

n satisfies the equation $0 \le n \le 5$, preferably $0 \le n \le 2$, and g satisfies the equation $0 \le g \le 500$, preferably $1 \le g \le 100$, more preferably $1 \le g \le 50$. If g is larger than the upper limit, hydrophilicity is insufficient, resulting in a lack of stability. $h_1$ to $h_3$ are an integer each satisfying the equation $0 \le h_1 \le 2$, $0 \le h_2 \le 2$ and $0 \le h_3 \le 2$.

The structure represented by the formula (12) $-Y^1OQ^2$ is obtained by using a polyglycerin compound having a terminal alkenyl group as an ingredient and conducting an addition reaction with a hydrosilyl group in organopolysiloxane. The polyglycerin compound having a terminal alkenyl group can be obtained by conducting an epoxy ring-opening reaction with an epoxy compound such as monoallyl glycidyl ether, monooctenyl glycidyl ether, glycidol, or glycidyl methyl ether, and a compound having a hydroxyl group such as glycerin, glycerin monoallyl ether, or glycidol, in the presence of an alkaline catalyst.

The epoxy ring-opening reaction with a hydroxyl group is known, and the kind of alkaline catalyst is not particularly limited, but potassium hydroxide, sodium hydroxide, sodium bicarbonate, sodium carbonate, potassium bicarbonate, potassium carbonate, sodium methoxide, or the like can be used. The amount of the alkaline catalyst added is 0.2 mol % to 2 mol %, preferably 0.2 mol % to 1 mol %, relative to 100 mol % of the compound having a hydroxyl group. The product of the epoxy ring-opening reaction with the hydroxyl group various isomers depending on the composition of the ingredients and is thus generally a mixture. For example, in a reaction of 1 mol of glycerin monoallyl ether and 1 mol of glycidol, the following four structural isomers are theoretically produced.

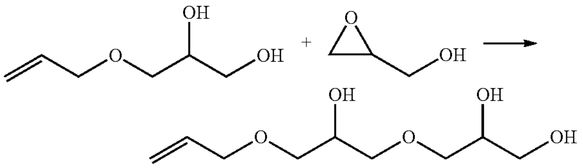

(A-1)

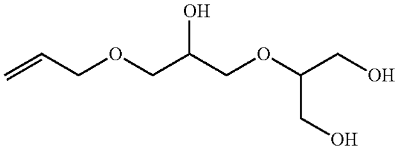

(A-2)

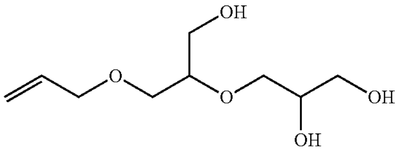

(A-3)

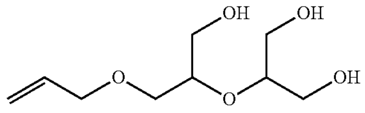

(A-4)

In the above reaction, the proportion of the compound having a structure represented by the formula (A-1) generally becomes high. When the compound is used as an ingredient, the structure represented by the formula (12) is a mixture of structures derived from compounds represented by (A-1) to (A-4) and an unreacted glycerin monoallyl ether-derived structure. For example, compound (A-1) above provides a structure having the formulas (15) and (16), compound (A-2) above provides a structure having the formulas (15) and (19), compound (A-3) above provides a structure having the formulas (14) and (16), compound (A-4) above provides a structure having the formulas (14) and (19), and the unreacted glycerin monoallyl ether provides a structure having the formula (15).

More preferably, alkenyl groups of the compounds represented by the formulas (A-1) to (A-4) are subjected to an addition reaction with a hydrosilyl group in organopolysiloxane, to provide an organopolysiloxane having polyhydric alcohol-containing hydrocarbon groups represented by the following formulas (A-1') to (A-4') as $R^2$ in the formula (1)

(A-1')

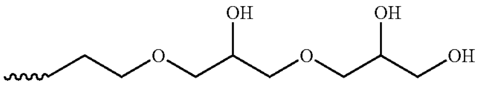

(A-2')

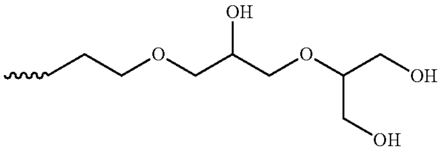

(A-3')

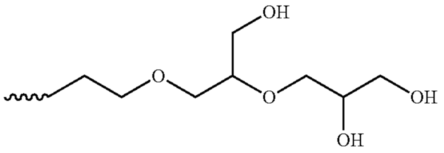

(A-4')

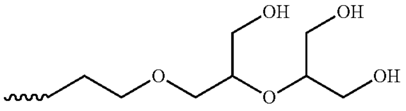

The structure represented by the formula (3): $-Y^1OQ^1Y^1-$ is obtained by using a polyglycerin compound having alkenyl groups at both ends as an ingredient and conducting an addition reaction with a hydrosilyl group in organopolysiloxane. The polyglycerin compound having an alkenyl group at both ends may be obtained by conducting an epoxy ring-opening reaction with an epoxy compound such as monoallyl glycidyl ether, monooctenyl glycidyl ether, glycidol, or glycidyl methyl ether, and a compound having a hydroxyl group such as glycerin, diglycerin, glycerin monoallyl ether, or glycidol, in the presence of an alkaline catalyst.

The epoxy ring-opening reaction with a hydroxyl group is known, and the kind of alkaline catalyst is not particularly limited, but potassium hydroxide, sodium hydroxide, sodium bicarbonate, sodium carbonate, potassium bicarbonate, potassium carbonate, sodium methoxide, or the like may be used. The amount of the alkaline catalyst added is 0.2 mol % to 2 mol %, preferably 0.2 mol % to 1 mol %, relative to 100 mol % of the compound having a hydroxyl group. The product of the epoxy ring-opening reaction with the hydroxyl group various isomers depending on the composition of the ingredients and is thus generally a mixture. For example, in a reaction of 2 mol of monoallyl glycidyl ether and 1 mol of glycerin, the following 14 structural isomers are theoretically produced.

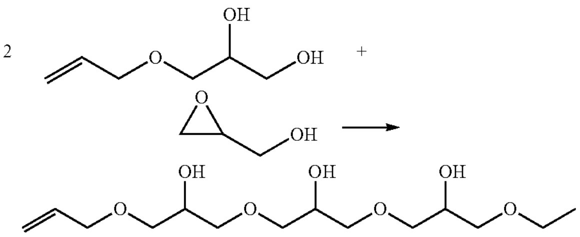

(B-1)

-continued

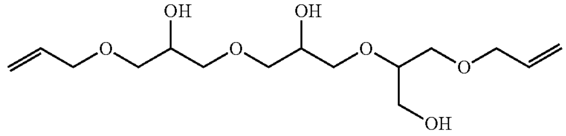

(B-2)

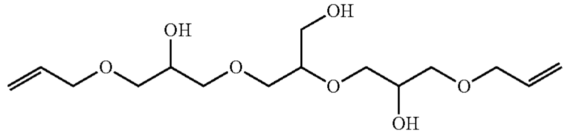

(B-3)

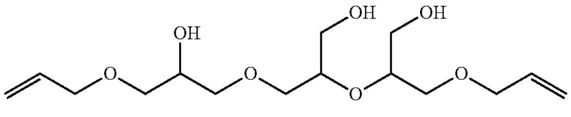

(B-4)

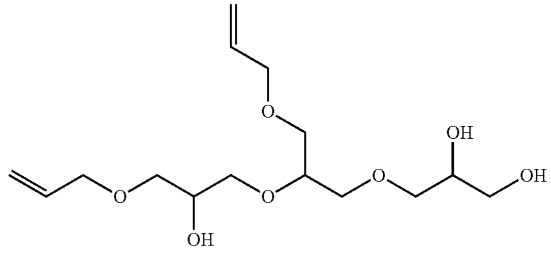

(B-5)

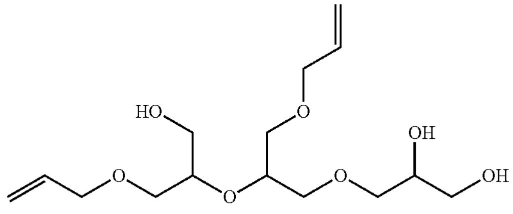

(B-6)

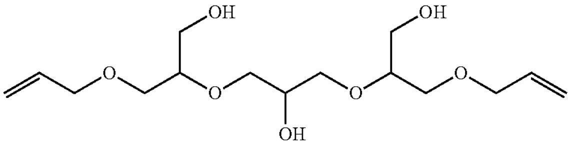

(B-7)

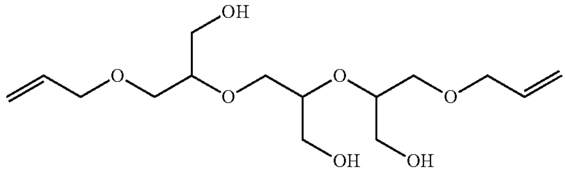

(B-8)

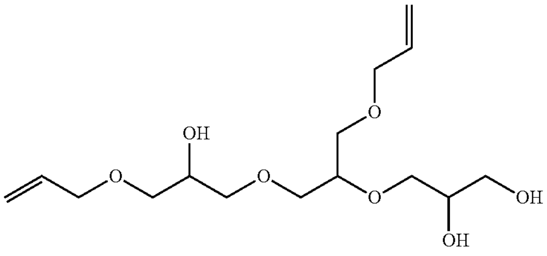

(B-9)

-continued

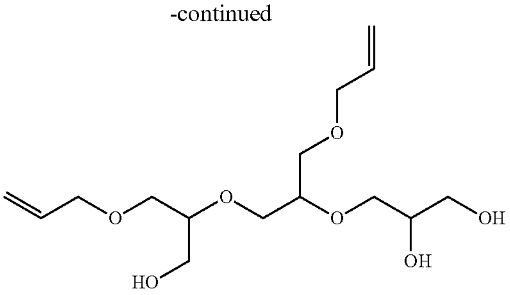

(B-10)

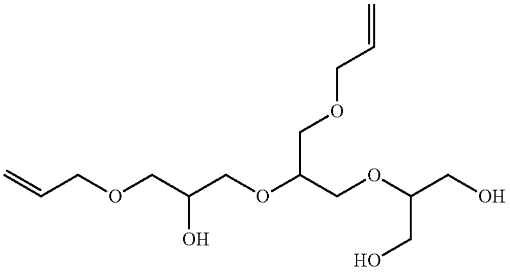

(B-11)

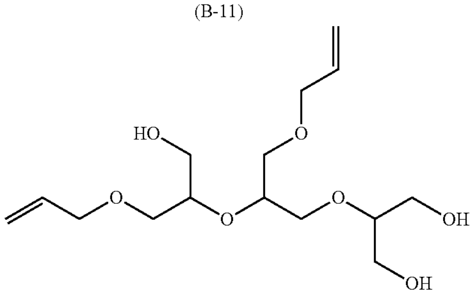

(B-12)

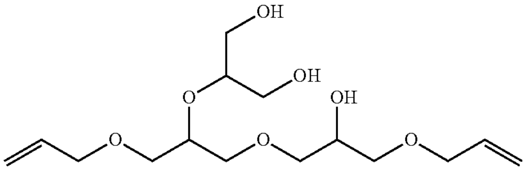

(B-13)

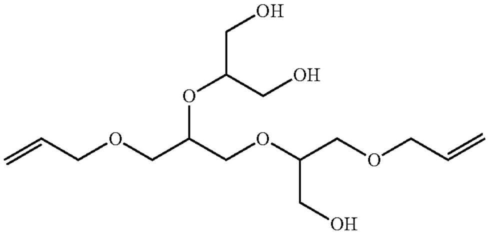

(B-14)

When the compound is used as an ingredient, the structure represented by the formula (3) in X of the formula (1) is a mixture of structures derived from the compounds represented by (B-1) to (B-14) and an unreacted glycerin-derived structure. For example, compound (B-1) above provides a structure having the formula (6), compound (B-2) above provides a structure having formulas (6) and (9), compound (B-3) above provides a structure having formulas (5) and (6), compound (B-4) above provides a structure having formulas (5), (6), and (9), compound (B-5) above provides a structure having formulas (6), (7), and (8), compound (B-6) above provides a structure having formulas (5), (7), and (8), compound (B-7) above provides a structure having formulas (5), (6), and (9), compound (B-8) above provides a structure having formulas (5) and (9), compound (B-9) above provides a structure having formulas (4), (6), and (7), compound (B-10) above provides a structure having formulas (4), (5), and (7), compound (B-11) above provides a structure having formulas (6), (8), and (10), compound (B-12) above provides a structure having formulas (5), (8), and (10), compound (B-13) above provides a structure having formulas (4), (6), and (10), and compound (B-14) above provides a structure having formulas (4), (9), and (10).

More preferably, alkenyl groups of the compounds represented by (B-1) to (B-14) above are subjected to an addition reaction with a hydrosilyl group in organopolysiloxane, to provide the structures having the following formulas (B-1') to (B-14') represented as X in the formula (1).

(B-1')

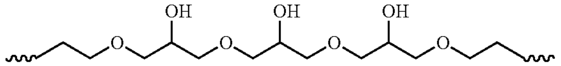

(B-2')

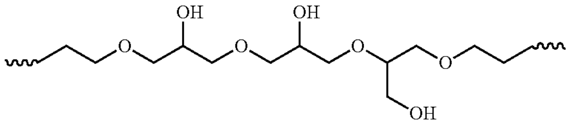

(B-3')

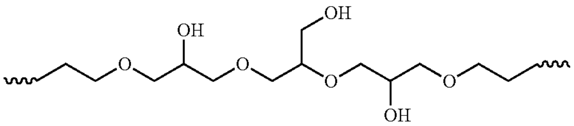

(B-4')

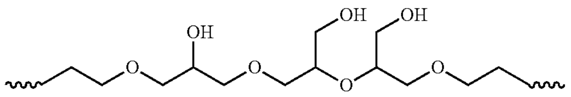

(B-5')

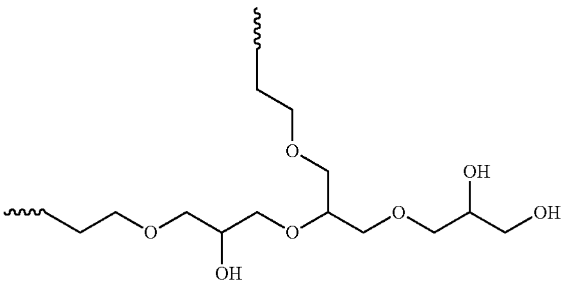

(B-6')

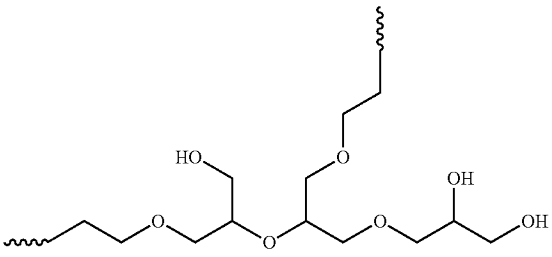

-continued (B-7')

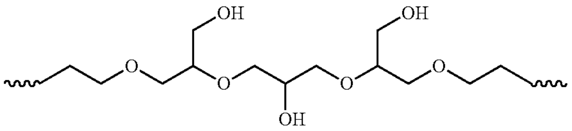

(B-8')

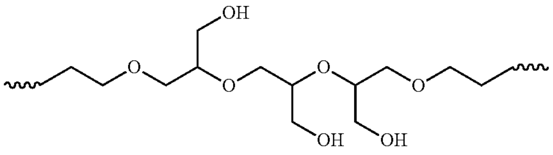

(B-9')

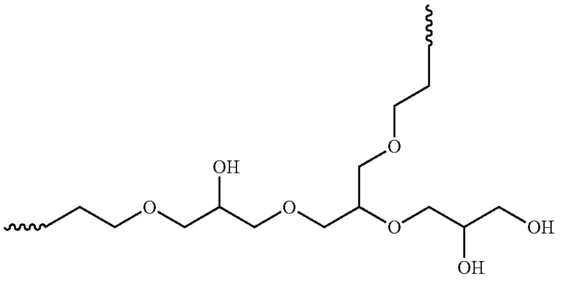

(B-10')

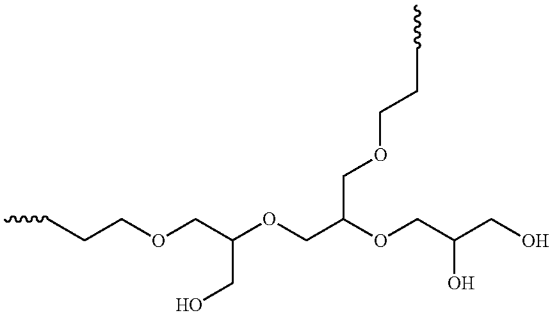

(B-11')

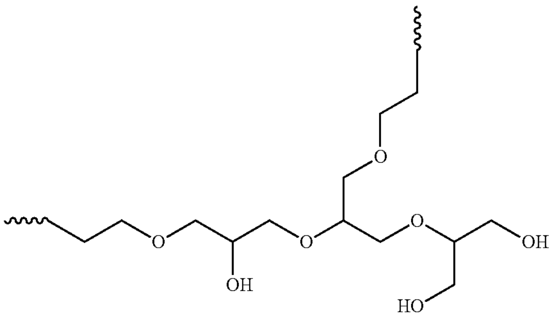

-continued (B-12')

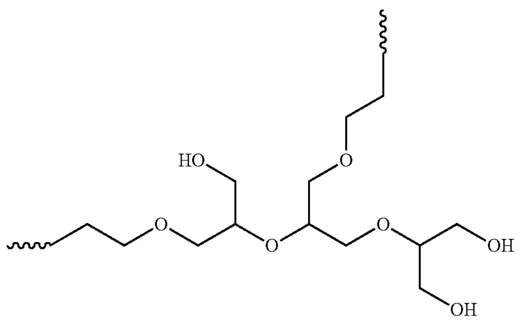

(B-13')

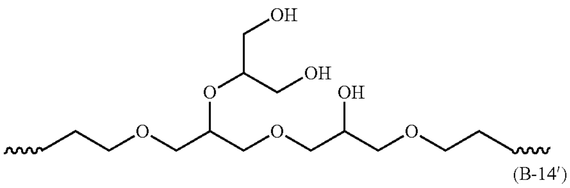

(B-14')

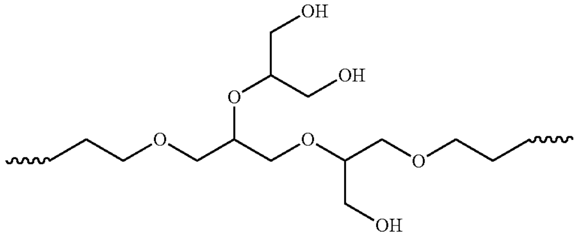

Furthermore, in terms of the reaction between a vinyl group and hydrogen polysiloxane, when compounds having the structures of the general formulas (20), (21), (22), and (23) are synthesized, n is preferably 0. In the general formula (20), if g is larger than 500, problems such as decreased reactivity with the main-chain hydrogen polysiloxane may occur, so n is preferably within the above range.

The crosslinked organic silicon resin of the present invention must have one or more of a group represented by the formula (2) or a group represented by the formula (3). The group represented by the formula (2) has a low glass transition point, which can impart flexibility to the organic silicon resin. Compared to the formula (2), the group represented by the formula (3) has a higher glass transition point due to having a hydrogen bonding functional group, which can impart rigidity to the organic silicon resin. Thus, it is possible to control physical properties of the crosslinked organic silicon resin by changing the ratio between the group represented by the formula (2) and the group represented by the formula (3).

The crosslinked organic silicon resin of the present invention preferably has a weight-average molecular weight in the range of 3,000 to 1,000,000, more preferably 4,000 to 500,000, even more preferably 3,000 to 500,000, still more preferably 3,000 to 300,000, or most preferably 10,000 to 100,000. The crosslinked organic silicon resin having a weight-average molecular weight in the range of 40,000 to 1,000,000 is not limited to silicone oil, and may be used as a water-in-oil emulsifier even when oil agents other than silicone oil are used in an oil phase, and the weight-average molecular weight is preferably in the range of 40,000 to 200,000 or is particularly preferable in the range of 45,000 to 100,000. The above ranges are more desirable in terms of efficiency and operability such as in filtration. In the present invention, the weight-average molecular weight may be determined as the polystyrene-equivalent weight-average molecular weight using gel permeation chromatography (GPC) conducted under the following conditions (hereinafter, the same applies).

[Measurement Conditions]

Eluent: Tetrahydrofuran (THF)

Flow rate: 0.6 mL/min

Detector: Differential refractive index (RI) detector; detector temperature of 40° C.

Column: TSK Guardcolumn SuperH-H TSKgel SuperHM-N (6.0 mm I.D.×15 cm×1)

TSKgel SuperH2500 (6.0 mm I.D.×15 cm×1) (manufactured by TOSOH CORPORATION)

Column temperature: 40° C.

Sample injection volume: 50 μL (concentration: 0.3 mass % THF solution)

The crosslinked organic silicon resin of the present invention having an HLB, calculated by Griffin's method, of 0.1 to 15 exhibits emulsifying properties and may be used as an emulsifier of the water-in-oil emulsion or the oil-in-water emulsion. In order to use the crosslinked organic silicon resin as a water-in-oil emulsifier, the crosslinked organic silicon resin of the present invention preferably has an HLB of 0.1 to 8.0, more preferably 0.1 to 6.0, or even more preferably 0.5 to 4.5. Griffin's method is defined as:

HLB value=20×(sum of molecular weights of hydrophilic moieties/total molecular weight). The HLB value is a numerical value that expresses the affinities of a surfactant to water and an oil agent.

The form of the crosslinked organic silicon resin of the present invention is liquid, gum, or solid at 25° C. When the physical form ranges from being solid to gum, it is required to be diluted with a solvent. When the form of the crosslinked organic silicon resin is liquid, it is not required to be diluted with a solvent and is easy to use. Generally, when the organic silicon resin is crosslinked, the molecular weight increases, resulting in the physical form becoming gum or solid. However, when the degree of modification of organopolysiloxane is increased, the glass transition point of the entire structure decreases and the physical form becomes liquid.

The crosslinked organic silicon resin of the average composition formula (1) wherein one or more of X are a group represented by the general formula (2), a4 in the average composition formula (1) satisfies the equation $0<a4\leq 10$, e1, e2, and e3 in the general formula (2) satisfy the equation $0<e1+e2+e3\leq 40$, the HLB calculated by Griffin's method is 0.1 to 6.0, and the physical form at 25° C. ranges from being liquid to gum to solid may be used as a water-in-oil emulsifier. Especially when the physical form ranges from being gum to solid, a coating film is formed when the solvent is volatilized and, thus, the crosslinked organic silicon resin may also be used as a coating film forming agent.

Preferably, the crosslinked organic silicon resin of the average composition formula (1) wherein one or more of X are a group represented by the general formula (2), a4 in the average composition formula (1) satisfies the equation $0<a4\leq 10$, e1, e2, and e3 in the general formula (2) satisfy the equation $8<e1+e2+e3\leq 40$, the HLB calculated by Griffin's method is 0.1 to 6.0, and the crosslinked organic silicon resin having the physical form at 25° C. of liquid or gum may be suitably used as a water-in-oil emulsifier. In addition, the crosslinked organic silicon resin has particularly excellent solubility in silicone oil, so a highly stable emulsion may be obtained even if silicone is used as an oil agent. If a4 is larger than 10, the molecular weight becomes high, which may not be preferable in terms of efficiency and operability such as in filtration. If e1+e2+e3 is larger than 40, hydrophilicity becomes too high, possibly resulting in a lack of emulsification stability. If e1+e2+e3 is smaller than 8, hydrophilicity becomes insufficient, possibly resulting in weaker emulsification and a lack of stability. If the physical form is gum, the crosslinked organic silicon resin has coating film-forming properties and thus may be used as a coating film forming agent and an emulsifier. If the form of the crosslinked organic silicon resin is liquid, the crosslinked organic silicon resin does not have coating film-forming properties and thus may be used only as an emulsifier, not as a coating film forming agent.

In particular, the crosslinked organic silicon resin wherein one or more of X are a group represented by the general formula (2), a3 and a4 in the average composition formula (1) satisfy the equations $1 \le a3 \le 100$ and $0 < a4 \le 3.5$, e in the general formula (2) satisfies the equation $8 < e1+e2+e3 \le 40$, the HLB calculated by Griffin's method is 0.1 to 6.0. The crosslinked organic silicon resin having the physical form at 25° C. of liquid may be used as a water-in-oil emulsifier. If a4 is larger than 3.5, the physical form is likely to range from being gum to solid. If a3 is smaller than 1, the degree of modification of organopolysiloxane is small, so the glass transition point does not decrease and the form of the crosslinked organic silicon resin is likely to range from being gum to solid. If a3 is larger than 100, hydrophilicity becomes insufficient, resulting in weaker emulsion and a lack of stability. If the properties of the crosslinked organic silicon resin are within the above ranges, the crosslinked organic silicon resin is liquid, so it does not need to be dissolved in a solvent, may be used as is, and is easy to use.

In particular, the crosslinked organic silicon resin of the average composition formula (1), wherein $R^1$ is an alkyl group which has 1 to 12 carbon atoms and does not have an aliphatic unsaturated bond, with a weight-average molecular weight of 40,000 to 1,000,000 is not limited to silicone oil, and may be used as a water-in-oil emulsifier even when oil agents other than silicone oil are used in an oil phase. If $R^1$ has more than 12 carbon atoms, solubility in silicone oil becomes poor, which is undesirable. If the weight-average molecular weight is below 40,000, stability over time becomes poor when an oil agent other than silicone oil is used in an oil phase, which is undesirable. If the weight-average molecular weight exceeds 1,000,000, the possibility of gelation increases, which is undesirable.

[Preparation Method]

The crosslinked organic silicon resin may be synthesized using various formulations known in the art. For example, the organic silicon resin may be crosslinked by conducting a reaction between a polyoxyalkylene-containing group having hydroxyl groups at both ends or a polyhydric alcohol-containing hydrocarbon group having two or more hydroxyl groups with the silanol group on the surface of the organic silicon resin. Since it is difficult to completely control the amount of the silanol group on the surface of the organic silicon resin, it is difficult to accurately control the crosslinking amount of the polyoxyalkylene-containing group or polyhydric alcohol-containing hydrocarbon group having two or more hydroxyl groups, which is a problem. Alternatively, the crosslinked organic silicon resin may be synthesized by an addition reaction between the organic silicon resin having an unsaturated group and the polyoxyalkylene-containing group having hydrosilyl groups at both ends or the polyhydric alcohol-containing hydrocarbon group having two or more hydroxyl groups. However, it is difficult to synthesize the polyhydric alcohol-containing hydrocarbon group or the polyoxyalkylene-containing group having introduced hydrosilyl groups in one-pot synthesis. Further, the types of other functional groups that may be introduced into the crosslinked organic silicon resin are limited, which is undesirable.

Thus, the crosslinked organic silicon resin is synthesized preferably by an addition reaction between the organic silicon resin having a hydrosilyl group and a polyoxyalkylene-containing group or polyhydric alcohol-containing hydrocarbon group, which has unsaturated groups at both ends.

The present invention further relates to a method for preparing the crosslinked organic silicon resin. The present method comprising a step of subjecting a hydrosilyl group-containing organic silicon resin represented by the average composition formula (26) and one or more terminal alkenyl group-containing compounds represented by the following general formula (24), (25), (27), (28), (29), (30), (31), or (32) to hydrosilylation to obtain the crosslinked organic silicon resin represented by the average composition formula (1), in which the terminal alkenyl group-containing compound includes at least one compound represented by the following formula (24).

$$(R^1{}_3SiO_{1/2})_{a1}(H_qR^1{}_{3-q}SiO_{1/2})_{a2+a3+a4}(R^1{}_2SiO_{2/2})_b(R^1SiO_{3/2})_c(SiO_{4/2})_d \quad (26)$$

wherein $R^1$, a1, a2, a3, a4, b, c, and d are as defined above, and q satisfies the equation $1 \le q \le 3$.

$$Y^2—O—(C_2H_4O)_{e1}(C_3H_6O)_{e2}(C_4H_8O)_{e3}—Y^2 \quad (24)$$

wherein $Y^2$ is a hydrocarbon group having 3 to 20 carbon atoms, which has a terminal alkenyl group and optionally an ether bond or an ester bond or both, and e1, e2, and e3 are defined above.

$$Y^2—O—Q^1—Y^2 \quad (25)$$

wherein $Y^2$ is a hydrocarbon group having 3 to 20 carbon atoms, which has a terminal alkenyl group and may have an ether bond or an ester bond or both, and $Q^1$ is as defined above.

$$Y^2—O—(C_2H_4O)_{e4}(C_3H_6O)_{e5}(C_4H_8O)_{e6}R^4 \quad (27)$$

wherein $Y^2$ is a hydrocarbon group having 3 to 20 carbon atoms, which has a terminal alkenyl group and may have an ether bond or an ester bond or both, and $R^4$, e4, e5, and e6 are as defined above.

$$Y^2—O—Q^2 \quad (28)$$

wherein $Y^2$ is as defined above, and $Q^2$ is as defined above.

$$CH_2{=}CH{-}C_nH_{2n}{-}(SiOR^1{}_2)_g{-}SiR^1{}_3 \tag{29}$$

$$CH_2{=}CH{-}C_nH_{2n}{-}SiR^1{}_{h1}{-}(OSiR^1{}_3)_{3\text{-}h1} \tag{30}$$

$$CH_2{=}CH{-}C_nH_{2n}{-}SiR^1{}_{h1}{-}(OSiR^1{}_{h2}(OSiR^1{}_3)_{3\text{-}h2})_{3\text{-}h1} \tag{31}$$

$$CH_2{=}CH{-}C_nH_{2n}{-}SiR^1{}_{h1}{-}(OSiR^1{}_{h2}(OSiR^1{}_{h3}(OSiR^1{}_3)_{3\text{-}h3})_{3\text{-}h2})_{3\text{-}h1} \tag{32}$$

wherein $R^1$, n, g, h1, h2, and h3 are as defined above.

$Y^2$ is a hydrocarbon group having 3 to 20 carbon atoms, which has a terminal alkenyl group and may have an ether bond or an ester bond or both. Examples of $Y^2$ include $CH_2{=}CH{-}$, $CH_2{=}CH{-}CH_2{-}$, $CH_2{=}CH{-}(CH_2)_2{-}$, $CH{=}C(CH_3)\ CH_2{-}$, $CH_2{=}CH{-}(CH_2)_6{-}$, $CH_2{=}CH{-}(CH_2)_9{-}$, $CH_2{=}CH{-}CH_2{-}O{-}(CH_2)_2{-}$, and $CH_2{=}CH{-}O{-}(CH_2)_3{-}$, and $CH_2{=}CH{-}$, $CH_2{=}CH{-}CH_2{-}$, and $CH_2{=}CH{-}(CH_2)_2{-}$ are preferable.

The hydrosilyl group-containing organic silicon resin represented by the average composition formula (26), as essential components, a Q unit ($SiO_{4/2}$) and an M unit (($R^1{}_3SiO_{1/2}$) and ($H_nR^1{}_{3\text{-}n}SiO_{1/2}$)), and, as optional components, a D unit ($R^1{}_2SiO_{2/2}$) and a T unit ($R^1SiO_{3/2}$). The hydrosilyl group-containing organic silicon resin may be solid or liquid at 25° C. and is preferably solid when imparting coating film-forming properties. Examples thereof include an MQ resin, an MTQ resin, an MDQ resin, and an MDTQ resin. The weight-average molecular weight is preferably in the range of 1,000 to 30,000 or more preferably in the range of 1,000 to 20,000 in terms of efficiency and operability such as in filtration.

The method for preparing a crosslinked organic silicon resin using the hydrosilylation reaction is described in detail below. In the hydrosilylation reaction of the hydrosilyl group-containing organic silicon resin represented by the average composition formula (26) and the terminal unsaturated group-containing compound represented by the general formula (24), (25), (27), (28), (29), (30), (31), or (32), the molar ratio of hydrosilyl group/terminal unsaturated group is preferably 0.5 to 2.0 or more preferably 0.8 to 1.2.

The hydrosilylation reaction is preferably performed in the presence of a platinum catalyst or rhodium catalyst. For example, chloroplatinic acid, alcohol-modified chloroplatinic acid, a chloroplatinic acid-vinylsiloxane complex, and the like are preferable. Since an excess amount of the catalyst used causes coloration of the reactant, the amount of platinum or rhodium is preferably 50 ppm or less or is particularly preferable at 20 ppm or less.

The addition reaction may be performed in the presence of an organic solvent if necessary. Examples of the organic solvent include: cyclic organopolysiloxanes such as octamethylcyclotetrasiloxane, decamethylcyclopentasiloxane, and dodecamethylcyclohexasiloxane; aromatic hydrocarbons such as toluene and xylene; ketone-based organic solvents such as acetone, methyl ethyl ketone, diethyl ketone, and methyl isobutyl ketone; aliphatic hydrocarbons such as hexane, heptane, octane, and cyclohexane; monovalent aliphatic alcohols such as methanol, ethanol, 1-propanol, 2-propanol, 1-butanol, 2-methyl-1-propanol, 2-butanol, 2-methyl-2-propanol, 1-pentanol, 2-methyl butanol, 2-pentanol, 1-hexanol, 2-methyl pentanol, 1-heptanol, 1-octanol, 1-nonanol, and 1-decanol; and divalent aliphatic alcohols such as ethylene glycol and 1,2-propylene glycol. In particular, ethanol, 1-propanol, and 2-propanol are preferable in terms of reactivity.

The amount of solvent used is preferably 1 mass % to 80 mass % or more, preferably 5 mass % to 50 mass %, relative to the entire reaction solution (system). When the amount is within the range, uniformity in the reaction system is maintained, and the reaction proceeds efficiently.

The conditions of the addition reaction are not particularly limited, but heating is preferably performed at a temperature of 50° C. to 150° C. or more preferably 80° C. to 120° C. for 1 hour to 10 hours under reflux.

After the addition reaction, the process of removing the rhodium catalyst or platinum catalyst with activated carbon may be included. The amount of the activated carbon used is preferably 0.001 mass % to 5.0 mass %, or is particularly preferable from 0.01 mass % to 1.0 mass %, relative to the entire system. When the amount is within the range, coloration of the reactant may be better suppressed.

After the addition reaction, unreacted hydrosilyl groups may be present in the crosslinked organic silicon resin. If the organic solvent used in the addition reaction is an aliphatic alcohol, alkoxy groups may remain because the alcohol exchange reaction and dehydrogenation reaction proceed.

After the addition reaction, the process of substituting the remaining hydrosilyl groups with hydroxysilyl groups may be included if necessary. In particular, when the crosslinked organic silicon resin is used in cosmetics, the hydrosilyl group is deactivated by dehydrogenation reactions over time, possibly resulting in the generation of hydrogen gas, which is problematic in terms of safety. Thus, the method preferably includes substituting hydrosilyl groups with hydroxysilyl groups.

The substitution of the hydrosilyl groups with hydroxysilyl groups may be conducted by adding a basic catalyst such as an alkali metal carbonate, an alkali metal bicarbonate, or an alkali metal hydroxide to hydrolyze unreacted hydrosilyl groups, followed by adding an acid catalyst in an amount equal to the molar equivalent of the basic catalyst for neutralization. Specific examples of the basic catalyst include the following: strong basic catalysts such as lithium hydroxide, sodium hydroxide, potassium hydroxide, calcium hydroxide, and barium hydroxide; and weak basic catalysts such as sodium carbonate, calcium carbonate, and sodium bicarbonate. In terms of promoting the dehydrogenation reaction, the use of a strong basic catalyst is particularly preferable, specifically sodium hydroxide. Specific examples of the acid catalyst include the following: inorganic acids such as hydrochloric acid, sulfuric acid, sulfurous acid, fuming sulfuric acid, and phosphoric acid; sulfonic acids such as p-toluenesulfonic acid, methanesulfonic acid, and trifluoromethanesulfonic acid; and carboxylic acids such as formic acid, acetic acid, propionic acid, trifluoroacetic acid, benzoic acid, citric acid, and oxalic acid. In general, it is preferable to use the acid or alkali in combination with water and to heat it to a temperature below the boiling point of water rather than using the acid or alkali by itself. In the substitution, the hydrosilyl groups (SiH groups) are substituted with hydroxysilyl groups (SiOH groups).

After the addition reaction, the method may further include performing deodorization to reduce any odors if necessary. In particular, when the crosslinked organic silicon resin is used in cosmetics, the product becomes odorized over time, so the method preferably includes deodorization. The general mechanism of odorization of polyether-modified silicone is described as follows. In the addition reaction between allyl etherified polyether and hydrogen polyorganosiloxane in the presence of a platinum catalyst, propenyl etherified polyether is generated by the internal transfer of the allyl group as a side reaction. Propenyl etherified polyether is not reactive in the addition reaction with hydrogen polyorganosiloxane, and thus remains as an impurity in the system. When water acts on the propenyl etherified polyether, it is considered that propenyl ether is hydrolyzed to generate propionaldehyde, which is the cause of the odor. It is also known that the hydrolysis reaction is accelerated in the presence of an acid catalyst. If polyether-modified silicone is used in water-based cosmetics, the liquid becomes acidic over time due to the oxidative degradation of the polyether, which accelerates the hydrolysis reaction mentioned above and causes the odor.

There are two typical examples of the deodorization process. In the first example, an acid catalyst is added to the solution after the addition reaction to completely hydrolyze all the propenyl ether remaining in the system and generated propionaldehyde is removed by strip purification (Japanese Patent No. 2137062).

Specific examples of the acid catalyst to be used in the first example include: inorganic acids such as hydrochloric acid, sulfuric acid, sulfurous acid, fuming sulfuric acid, and phosphoric acid; sulfonic acids such as p-toluenesulfonic acid, methanesulfonic acid, and trifluoromethanesulfonic acid; and carboxylic acids such as formic acid, acetic acid, propionic acid, trifluoroacetic acid, benzoic acid, oxalic acid, and citric acid. These acids are used in a combined system with water, but if the acid used needs to be removed, an acid with a low boiling point such as hydrochloric acid, formic acid, acetic acid, and trifluoroacetic acid is preferably used. In terms of treatment efficiency, a strong acid such as hydrochloric acid and trifluoroacetic acid is preferably used, but if cyclic organopolysiloxane is used as a solvent, ring opening may occur with a strong acid, so a weak acid such as citric acid and acetic acid is preferably used.

Treatment temperature is preferably 80° C. or less to prevent hydrophilic groups from oxidizing. The amount of acidic aqueous solution added is preferably 0.1 mass % to 100 mass % or more, preferably 5 mass % to 30 mass %, relative to the organic group-modified organic silicon resin.

In terms of productivity, a method in which an aqueous solution is added so that the solution after the reaction has a pH of 7 or less and strip purification is performed after heating and stirring is preferable. The strip purification may be performed at room temperature or under reduced pressure, but the temperature is preferably 120° C. or less, and in order to efficiently perform strip purification under this temperature condition, it is preferably performed under reduced pressure, or in the case of normal pressure, with ventilation using an inactive gas such as nitrogen or argon.

In the second example, hydrogen is added to the solution after the addition reaction to alkylate the unsaturated double bond (so-called hydrogenation reaction), thereby stably controlling the generation of propionaldehyde over time (U.S. Pat. No. 5,225,509 and Japanese Patent Application Laid-Open No. H7-330907).

The hydrogenation reaction may be performed using hydrogen or a metal hydride, and may also be a homogeneous or heterogeneous reaction. These may be performed alone or in combination. However, considering the advantage of having the catalyst used not remain in the product, a heterogenous catalytic hydrogenation reaction using a solid catalyst is most preferable.

Examples of the solid catalyst include simple substances and compounds of nickel, palladium, platinum, rhodium, cobalt, chromium, copper, and iron. In such a case, a catalyst support is unnecessary, but if used, activated carbon, silica, silica-alumina, alumina, zeolite, or the like is used. These catalysts may be used alone or in combination. The most preferable catalyst is Raney nickel, which is economically superior. Raney nickel is usually used in alkali, and thus, the pH of the reaction solution in particular needs to be carefully measured. In addition, the reaction system becomes slightly alkaline, and thus, a hydrolysis reaction with an acidic aqueous solution is particularly effective for deodorization.

In general, the hydrogenation reaction is performed preferably at 1 MPa to 100 MPa and 50° C. to 200° C. The hydrogenation reaction may be a batch reaction or a continuous reaction. In the case of a batch reaction, the reaction time depends on the amount of catalyst, the temperature, and the like, but is approximately 3 hours to 12 hours. The pressure of hydrogen may be adjusted to be constant as appropriate, but since the end point of the hydrogenation reaction is the point in time at which the pressure of hydrogen stops changing, it may be determined by carefully observing the pressure gauge.

The amount of aldehyde contained in the crosslinked organic silicon resin purified by such an acid treatment and hydrogenation reaction may be 70 ppm or less, 20 ppm or less, or 10 ppm or less.

Furthermore, the two deodorization processes described above may be used in combination. The formulation of the acid treatment may decompose and remove aldehyde compounds but cannot completely remove unsaturated double bonds. Thus, the resulting generation of aldehyde, which is a cause of the odor, cannot be completely suppressed. The formulation of the hydrogenation reaction can reduce the amount of aldehyde compounds generated as a result of eliminating the unsaturated double bonds that produce them, but aldehyde condensates, which are generated by the condensation of some aldehydes, remain in the system even with the formulation, and are difficult to remove via strip purification. Therefore, the solution after the addition reaction is subjected to the hydrogenation reaction to alkylate the remaining unsaturated double bonds, and an acid catalyst is added thereto to decompose the aldehyde condensates in the system, so that complete odorlessness can be achieved (WO 2002/05588).

[Method for Preparing Hydrosilyl Group-Containing Organic Silicon Resin as Ingredient]

The form of the hydrosilyl group-containing organic silicon resin represented by the average composition formula (26) may be solid or liquid at 25° C., but is preferably liquid in terms of compatibility with oil agents in cosmetics and feeling on use. The hydrosilyl group-containing organic silicon resin is preferably not diluted in terms of selectivity with oil agents. The use of solvents having a higher boiling point than the reflux temperature during hydrolysis is preferable.

Examples of the oil agents used for dilution include: silicone oils such as dimethylpolysiloxane (such as KF-96L-1cs, KF-96L-1.5cs, and KF-96L-2cs produced by Shin-Etsu Chemical Co., Ltd.), octamethyltetrasiloxane (D4), decamethylpentasiloxane (D5) (KF-995 produced by Shin-Etsu Chemical Co., Ltd.), dodecamethylhexasiloxane (D6), tristrimethylsiloxymethylsilane (TMF-1.5 produced by Shin-Etsu Chemical Co., Ltd.), caprylyl methicone, phenyl trimethicone, methylphenylpolysiloxane (KF-54 and KF-54HV produced by Shin-Etsu Chemical Co., Ltd.), diphenylsiloxy phenyl trimethicone (KF-56A produced by Shin-Etsu Chemical Co., Ltd.), methylhexylpolysiloxane, and linear or branched organopolysiloxane with a low to high viscosity such as a dimethylsiloxane-methylphenylsiloxane copolymer; aromatic hydrocarbons such as toluene and xylene; aliphatic ketones such as acetone, methyl ethyl ketone, diethyl ketone, and methyl isobutyl ketone; aliphatic hydrocarbons such as hexane, heptane, octane, cyclohexane, isooctane, isododecane, and isohexadecane; monovalent aliphatic alcohol ethylene glycols such as methanol, ethanol, 1-propanol, 2-propanol, 1-butanol, 2-methyl-1-propanol, 2-butanol, 2-methyl-2-propanol, 1-pentanol, 2-methyl butanol, 2-pentanol, 1-hexanol, 2-methyl pentanol, 1-heptanol, 1-octanol, 1-nonanol, and 1-decanol; and divalent aliphatic alcohols such as 1,2-propylene glycol. The oil agents are preferably polysiloxanes such as dimethylpolysiloxane, octamethyltetrasiloxane, decamethylpentasiloxane, dodecamethylhexasiloxane, tristrimethylsiloxymethylsilane, and phenyl trimethicone and branched aliphatic hydrocarbons such as isooctane, isododecane, and isohexadecane, in terms of safety and storage stability.

The hydrosilyl group-containing organic silicon resin represented by the average composition formula (26) may be produced by the known methods. For example, the preparation can be done by the method described in Japanese Patent Application Laid-Open No. 2017-75283.

More specifically, the hydrosilyl group-containing organic silicon resin may be obtained as follows. After hydrolysis in the presence of an acid catalyst, a mixture of one or two or more selected from the group consisting of the organic silicon compounds represented by the following general formulas (33) and (34), one or two or more selected from the group consisting of the hydrosilyl group-containing organic silicon compounds represented by the general formulas (35) and (36), and one or two or more selected from the group consisting of the hydrolyzable silane represented by the general formula (37), partially hydrolyzed condensates of the hydrolyzable silane, and metal salts of the hydrolyzable silane, is neutralized by adding an basic catalyst in an amount greater than the molar equivalent of the acid catalyst, and is then condensed and obtained in the presence of the basic catalyst.

$$R^1_3SiOSiR^1_3 \quad (33)$$

$$R^1_3SiX^1 \quad (34)$$

$$H_qR^1_{(3-q)}SiOSiR^1_{(3-q)}H_q \quad (35)$$

$$H_qR^1_{(3-q)}SiX^1 \quad (36)$$

$$SiX^1_4 \quad (37)$$

wherein $R^1$ is as defined above, $X^1$ is, independently of each other, a hydrolyzable functional group, and q satisfies the equation $1 \le q \le 3$.

In the general formulas (34), (36), and (37), $X^1$ is, independently of each other, a hydrolyzable functional group directly bonded to a silicon atom, and examples thereof include: halogen atoms such as a chlorine atom and a bromine atom; alkoxy groups such as a methoxy group, an ethoxy group, a propoxy group, and a butoxy group; an alkenoxy group; an acyloxy group; an amide group; and an oxime group. Among them, $X^1$ is, in particular, preferably a methoxy group, an ethoxy group, or a chlorine atom considering ease of availability and hydrolysis rate.

Examples of the organic silicon compound represented by the general formula (33) include 1,1,1,3,3,3-hexamethyldisiloxane, 1,1,1,3,3,3-hexaphenyldisiloxane, 1,1,3,3-tetramethyl-1,3-divinyldisiloxane, 1,1,1,3,3,3-hexaethyldisiloxane, 1,1,1,3,3,3-hexavinyldisiloxane, 1,1,1,3,3-pentavinylmethyldisiloxane, 1,1,1,3,3-n-octylpentamethyldisiloxane, 1,1,1,3,3-chloromethylpentamethyldisiloxane, 1,1,3,3-tetramethyl-1,3-diallyldisiloxane, and 1,3-dimethyl-1,1,3,3-tetravinyldisiloxane. 1,1,1,3,3,3-hexamethyldisiloxane, 1,1,1,3,3,3-hexaphenyldisiloxane, and the like are particularly preferable.

Examples of the organic silicon compound represented by the general formula (34) include trimethylchlorosilane, triethylchlorosilane, ethyldimethylchlorosilane, trivinylchlorosilane, dimethylvinylchlorosilane, triphenylchlorosilane, dimethylphenylchlorosilane, methyldiphenylchlorosilane, trimethylmethoxysilane, trimethylethoxysilane, triethylmethoxysilane, triethylethoxysilane, triphenylmethoxysilane, and triphenylethoxysilane. Trimethylchlorosilane, trimethylethoxysilane, and the like are particularly preferable.

Examples of the hydrosilyl group-containing organic silicon compound represented by the general formula (35) include 1,1,3,3-tetramethyldisiloxane and 1,1,1,3,3-pentamethyldisiloxane. 1,1,3,3-tetramethyldisiloxane is particularly preferable. In the general formulas (35) and (36), q satisfies the equation 1 q 3, but in the general formula (35), a hydrogen atom bonded to one silicon atom, indicated by q relating to $R^1$, may be identical to or different from the hydrogen atom bonded to the other silicon atom, indicated by q relating to the other $R^1$.

Examples of the hydrosilyl group-containing organic silicon compound represented by the general formula (36) include dimethylchlorosilane, diphenylchlorosilane, dimethylmethoxysilane, and dimethylethoxysilane. Dimethylchlorosilane and dimethylmethoxysilane are particularly preferable.

Examples of the hydrolyzable silane represented by the general formula (37) include tetrachlorosilane, tetramethoxysilane, and tetraethoxysilane. Examples of the partially hydrolyzed condensate of the hydrolyzable silane include tetramethoxysilane condensate and tetraethoxysilane condensate. Examples of the metal salt of the hydrolyzable silane include soluble glass, sodium silicate, and potassium silicate. Tetraethoxysilane and tetraethoxysilane condensate are particularly preferable.

In the preparation of the hydrosilyl group-containing organic silicon resin represented by the average composition formula (26), before hydrolysis of a mixture of one or two or more selected from the group consisting of the compounds represented by the general formulas (33), (34), (35), (36), and (37) in the presence of an acid catalyst, or after the hydrolysis but before the additional hydrolysis mentioned below, a mixture of one or two or more selected from the group consisting of the organic silicon compounds represented by the general formulas (38) and (39) may also be added.

$$R^1SiX^1_3 \quad (38)$$

$$R^1_2SiX^1_2 \quad (39)$$

wherein $R^1$ and $X^1$ are as defined above.

In the general formulas (38) and (39), $X^1$ is, independently of each other, a hydrolyzable functional group directly bonded to a silicon atom, and examples thereof include halogen atoms such as a chlorine atom and a bromine atom; alkoxy groups such as a methoxy group, an ethoxy group, a propoxy group, and a butoxy group; an alkenoxy group; an acyloxy group; an amide group; and an oxime group. Among them, $X^1$ is, in particular, preferably a methoxy group, an ethoxy group, or a chlorine atom, considering ease of availability and hydrolysis rate.

Examples of the silicon compound represented by the general formula (38) include methyltrimethoxysilane, methyltriethoxysilane, ethyltrimethoxysilane, pentyl triethoxysilane, phenyltriethoxysilane, benzyltriethoxysilane, chloropropyltriethoxysilane, bromopropyltriethoxysilane, cyclohexyltrimethoxysilane, trifluoropropyltrimethoxysilane, and methyltrichlorosilane. Methyltrimethoxysilane, methyltriethoxysilane, and methyltrichlorosilane are particularly preferable.

Examples of the silicon compound represented by the general formula (39) include dimethyldimethoxysilane, dimethyldiethoxysilane, diethyldimethoxysilane, dipentyldiethoxysilane, diphenyldiethoxysilane, dibenzyldiethoxysilane, dichloropropyldiethoxysilane, dibromopropyldiethoxysilane, dicyclohexyldimethoxysilane, difluoropropyldimethoxysilane, and dimethyldichlorosilane. Dimethyldimethoxysilane, dimethyldiethoxysilane, and dimethyldichlorosilane are particularly preferable.

A more detailed example of the method for preparing the hydrosilyl group-containing organic silicon resin represented by the average composition formula (26) is described below.

A solvent (especially an organic solvent) and a hydrolysis ingredient (i.e., a mixture of one or two or more selected from the group consisting of the organic silicon compounds represented by the general formulas (33) and (34), one or two or more selected from the group consisting of the hydrosilyl group-containing organic silicon compounds represented by the general formulas (35) and (36), and one or two or more selected from the group consisting of the hydrolyzable silane represented by the general formula (37), partially hydrolyzed condensates of the hydrolyzable silane, and metal salts of the hydrolyzable silane) are placed in a reaction vessel, an acid, which is a catalyst, is then added, and water is then added dropwise while stirring. In this case, an organic solvent may be added after the dropwise addition of water. Since hydrolysis is preferably performed under acidic conditions, the addition of the acid catalyst is essential.

The temperature in the dropwise addition of water is preferably 0° C. to 80° C. or is particularly preferable from 0° C. to 50° C., and temperatures in this range may suppress heat derived from the hydrolysis reaction between the hydrolysis ingredients in the system. The molar ratio of the amount of water to be added dropwise is in the range of 0.6 to 2, preferably 1.0 to 1.8, relative to the hydrolyzable functional group (alkoxy group and the like). Amounts in this range allow for the further suppression of the deactivation of the hydrosilyl groups.

The solvent to be used in the hydrolysis reaction is preferably an organic solvent in order to maintain uniformity in the reaction system during the hydrolysis reaction and suppress reductions in reaction rate due to increases in viscosity. The solvent desirably has a boiling point higher than the reflux temperature during hydrolysis.

Examples of the organic solvent include: cyclic organopolysiloxanes such as octamethylcyclotetrasiloxane, decamethylcyclopentasiloxane, and dodecamethylcyclohexasiloxane; aromatic hydrocarbons such as toluene and xylene; aliphatic ketones such as acetone, methyl ethyl ketone, diethyl ketone, and methyl isobutyl ketone; and aliphatic hydrocarbons such as hexane, heptane, octane, and cyclohexane.

An alcohol solvent having 1 to 10 carbon atoms, preferably 1 to 4 carbon atoms, may also be used in combination if necessary. Examples of the alcohol solvent include methanol, ethanol, 1-propanol, 2-propanol, 1-butanol, 2-methyl-1-propanol, 2-butanol, 2-methyl-2-propanol, 1-pentanol, 2-methyl butanol, 2-pentanol, 1-hexanol, 2-methyl pentanol, 1-heptanol, 1-octanol, 1-nonanol, 1-decanol, ethylene glycol, and 1,2-propylene glycol. The alcohol solvent causes an alcohol exchange reaction with a hydrolyzable group such as an alkoxy group, and thus, the use of a long-chain alcohol solvent leads to a rate-limiting hydrolysis reaction. Accordingly, the alcohol solvent is, in particular, preferably methanol, ethanol, 1-propanol, or 2-propanol.

The amount of the solvent used is preferably 1 mass % to 80 mass % or, is particularly preferable from 5 mass % to 50 mass %, relative to the entire reaction solution (system). When the amount is within the range, uniformity of the reaction system is maintained, and the reaction proceeds efficiently.

Examples of the acid catalyst include: inorganic acids such as hydrochloric acid, sulfuric acid, sulfurous acid, fuming sulfuric acid, and phosphoric acid; sulfonic acids such as p-toluenesulfonic acid, methanesulfonic acid, and trifluoromethanesulfonic acid; and carboxylic acids such as formic acid, acetic acid, propionic acid, trifluoroacetic acid, benzoic acid, citric acid, and oxalic acid. The amount of the acid catalyst used may be small and is preferably in the range of 0.001 mass % to 10 mass %, relative to the entire reaction solution (system).

After adding water dropwise as described above, the hydrolysis reaction is conducted by adding heat at temperatures of, for example, 50° C. to 150° C., or more preferably 80° C. to 120° C., for 2 hours to 8 hours. In such a case, the hydrolysis reaction is conducted at a temperature which is less than the boiling point of the hydrosilyl group-containing organic compound used, so the deactivation of the hydrosilyl groups may be further suppressed.

After the hydrolysis of the hydrolysis ingredients in the presence of an acid catalyst as described above, the product is cooled to a temperature of 10° C. to 100° C., preferably 10° C. to 60° C., more preferably 10° C. to 30° C., or even more preferably 25° C.

After the hydrolysis, the product is neutralized with a basic catalyst such as an alkali metal carbonate, an alkali metal bicarbonate, or an alkali metal hydroxide at 10° C. to 40° C. In such a case, the use of a strong basic catalyst and a weak basic catalyst in combination further facilitates the suppression of the deactivation of the hydrosilyl groups and accelerates the condensation reaction of the organic silicon resin. Examples of the strong basic catalyst include lithium hydroxide, sodium hydroxide, potassium hydroxide, calcium hydroxide, and barium hydroxide. Examples of the weak basic catalyst include sodium carbonate, calcium carbonate, and sodium bicarbonate. In particular, the combination of the strong basic catalyst and the weak basic catalyst is desirably a combination of sodium hydroxide and calcium carbonate due to their higher molecular weight. This combination may increase the molecular weight sufficiently and may yield a hydrosilyl group-containing organic silicon resin with a high molecular weight more reliably.

The amount of the basic catalyst used needs to be greater than the molar equivalent of the acid catalyst, and neutralizing with the basic catalyst in an amount greater than the molar equivalent of the acid catalyst gives priority to the condensation reaction of the organic silicon resin, resulting in an increase in molecular weight. Thus, a hydrosilyl group-containing organic silicon resin with a high molecular weight may be obtained. The amount of the basic catalyst used is preferably in the range of 1.1 to 3.0 molar equivalents of the acid catalyst. The pH in the system is preferably 7 to 12 or more preferably 7 to 9. When the amount of the basic catalyst added is within the range, the condensation reaction of the hydrosilyl group-containing organic silicon resin is prioritized, thereby yielding a resin having the target molecular weight.

After the neutralization, generated alcohols, solvents, and excess water may be removed by heating at 95° C. to 120° C. under normal pressure or reduced pressure. After confirming the removal of the generated alcohols, solvents, and excess water, the condensation reaction is conducted, for example, by heating at 120° C. to 150° C. for 2 hours to 5 hours. Thus, a hydrosilyl group-containing organic silicon resin is obtained.

In the method for preparing the hydrosilyl group-containing organic silicon resin, the molar ratio in terms of use of the total mass of the compounds of the general formulas (33), (34), (35), and (36) to the mass of the $SiO_{42}$ units in the compound of the general formula (37), the total number of moles of (33), (34), (35), and (36): the number of moles of (37), is preferably 0.3:1 to 2:1 or more preferably 0.6:1 to 1.3:1. The molar ratio in terms of use of the total mass of the compounds of the formulas (33) and (34) to the total mass of the compounds of the formulas (35) and (36), ((33)+(34)): ((35)+(36)), is preferably 0.3:1.0 to 2.0:1.0 or more preferably 0.6:1.0 to 1.3:1.0. When the ratios in terms of use are within the ranges, the amount of hydrosilyl groups contained in the hydrosilyl group-containing organic silicon resin may be more accurately changed quantitatively. As such, in the present invention, the amount of hydrosilyl groups contained in the organic silicon resin may be changed quantitatively by changing the added amount of the compounds represented by the general formulas (35) and (36).

In the method for preparing the hydrosilyl group-containing organic silicon resin, a reaction that deactivates some hydrosilyl groups may occur as shown in the following reaction formula.

$$SiO_{1/2}H_{p1}R_{3\text{-}p1} \quad \text{(M unit)} \quad + \quad \sim Si—OH$$

$$\longrightarrow \sim Si—O—SiO_{1/2}H_{p1\text{-}1}R_{3\text{-}p1} \quad \text{(D unit)} \quad (p \geq 1)$$

$$\longrightarrow \sim(Si—O)_2—SiO_{1/2}H_{p1\text{-}2}R_{3\text{-}p1} \quad \text{(T unit)} \quad (p \geq 2)$$

$$\longrightarrow \sim(Si—O)_3—SiO_{1/2}R_3 \quad \text{(Q unit)} \quad (p = 3)$$

wherein R is a monovalent hydrocarbon group having 1 to 10 carbon atoms, and p1 is an integer from 1 to 3.

In the method for preparing the hydrosilyl group-containing organic silicon resin, a mixture of one or two or more selected from the group consisting of the organic silicon compounds represented by the general formulas (26) and (27) and one or two or more selected from the group consisting of the hydrolyzable silane represented by the general formula (28), partially hydrolyzed condensates of the hydrolyzable silane, and metal salts of the hydrolyzable silane is hydrolyzed in the presence of an acid catalyst, and one or two or more selected from the group consisting of the hydrosilyl group-containing organic silicon compounds represented by the general formulas (28) and (29) are added to the product to conduct an additional hydrolysis, thereby allowing for the suppression of the deactivation of the hydrosilyl groups.

The hydrosilyl group-containing organic silicon compounds represented by the general formulas (28) and (29) are preferably added dropwise, more preferably added dropwise at a rate of 5 mL/min to 100 mL/min, or even more preferably at 10 mL/min to 50 mL/min.

The additional hydrolysis reaction is conducted by preferably heating at a temperature which is less than the boiling points of the hydrosilyl group-containing organic compounds to be applied to the reaction, for example, at 40° C. to 150° C. or more preferably at 40° C. to 120° C., for 2 hours to 8 hours. When the reaction is conducted within the temperature range, the deactivation of the hydrosilyl groups may be further suppressed. Further, deactivation of the hydrosilyl groups may be further suppressed by adjusting the amounts of ingredients added and the type of catalyst.

For the hydrosilyl group-containing organic silicon resin represented by the average composition formula (26), the amount of hydrosilyl groups contained in the organic silicon resin may be easily adjusted by changing the amount of the hydrosilyl group-containing organic silicon compounds added, and a large amount of hydrosilyl groups may be introduced. Further, the molecular weight distribution, the shape, and the like of the organic silicon resin may be adjusted by changing the amounts of hydrolysis ingredients to be included, the type of acid catalyst, the amount of acid catalyst added, the reaction temperature, reaction time, the amount of solvent added, and the methods for the addition, and the hydrosilyl group-containing organic silicon resin may be produced according to the intended use.

[Physical Properties of Crosslinked Organic Silicon Resin]

The crosslinked organic silicon resin of the present invention has a weight-average molecular weight in the range of preferably 3,000 to 1,000,000, more preferably 3,000 to 500,000, even more preferably 3,000 to 300,000, or most preferably 10,000 to 100,000. The above ranges are more desirable in terms of efficiency and operability such as in filtration.

The crosslinked organic silicon resin may be solid, gum, or liquid at 25° C. When coating film-forming properties are to be imparted, the crosslinked organic silicon resin preferably ranges from being solid to gum and is particularly preferable as a solid. Considering ease of use, the physical form is preferably liquid. In particular, the crosslinked organic silicon resin is preferably a crosslinked organic silicon resin in which, in the average composition formula (1), a3 is a number satisfying the equation $1 \leq a3 \leq 100$ and a4 is a number satisfying the equation $0 < a4 \leq 3.5$, and in the general formula (2), e1 and e2 are numbers satisfying the equation $8 < e1+e2 \leq 20$. The organic silicon resin is liquid at 25° C., preferably has a weight-average molecular weight in the range of 3,000 to 1,000,000, and is particularly preferable in the range of 3,000 to 500,000, in terms of efficiency and operability such as in filtration.

In the formula (1), the crosslinked organic silicon resin having one or more groups represented by the formula (2) or (3) that is solid or gum at 25° C. may be used more suitably as a coating film forming agent. If the organic silicon resin before being crosslinked forms a brittle yet firm coating film, the crosslinked organic silicon resin which is solid after being crosslinked forms a firm coating film without stickiness. In Japanese Patent Application No. 2018-131538, a firm coating film with excellent flexibility is formed by crosslinking the organic silicon resin with organopolysiloxane.

The crosslinked moiety (X) of the crosslinked organic silicon resin of the present invention is polyoxyethylene of the formula (2) or polyglycerin of the formula (3). The polyoxyethylene and the polyglycerin have higher glass transition points than organopolysiloxane and thus have low flexibilities and are less likely to form a flexible coating film.

In particular, when the organic silicon resin is crosslinked with polyglycerin of the formula (3), the crosslinked organic silicon resin has hydrogen bonds, thereby forming a rigid coating film. The crosslinked organic silicon resin which is gum after being crosslinked forms a flexible coating film. This is because the modification of a specific amount of organopolysiloxane lowers the melting point of the resin and imparts flexibility.

The crosslinked organic silicon resin of the present invention is preferably solid at 25° C. in order to exhibit coating film-forming properties. Whether or not a coating film will be formed may be determined based on whether or not a freestanding film is formed by adding drops of 1.5 grams of a solution obtained by diluting the organic silicon resin with isododecane or decamethylcyclopentasiloxane to 60 mass % on a resin plate made of polytetrafluoroethylene (PTFE) and then drying the product at 105° C. for 3 hours. If a coating film is not formed, oil will leak from cracks in the coating film, resulting in a significant decrease in oil resistance and a low adhesion to skin. Therefore, if such crosslinked organic silicon resin is included in a cosmetic, the cosmetic will have an unnatural finish.

The crosslinked organic silicon resin is contained in a cosmetic as a coating film forming agent to thereby provide a cosmetic which is not sticky when applied on skin, has an excellent feeling on use, has exceptional water resistance and oil resistance, and adheres well to skin. Therefore, a cosmetic with exceptional cosmetic retention (longevity) is provided.

When the crosslinked organic silicon resin is used as a water-in-oil emulsifier, the stabilizing power at the interface is higher than when a surfactant such as a conventional crosslinked silicone activator is used. Thus, when the emulsion thereof is applied to the skin, the emulsion is less likely to be broken, so the feeling on use of the oil phase is easier felt, resulting in a rich feeling on use. Emulsions having large particle diameters are generally known to more easily coalesce and be unstable. However, the emulsion obtained above may exist in a relatively stable manner. Further, when the emulsion obtained above is applied to the skin, a rich feeling is produced, but activator-specific stickiness is also reduced, resulting in a light texture. In particular, in the case of sunscreen cosmetics, the whitening phenomenon may be reduced, and in the case of makeup cosmetics, color unevenness may be reduced.

The crosslinked organic silicon resin of the present invention may be mixed with an oil agent and an activator as shown below in advance to form an intermediate composition so as to be more easily included in an oil phase ingredient. Further, the crosslinked organic silicon resin is used as an activator of an oily gelling agent or a dispersant of powder to form an intermediate composition thereof in advance.

<Cosmetics>

The crosslinked organic silicon resin (A) of the present invention may be used toward various applications, and is particularly applicable as an ingredient for all cosmetics used externally on skin and hair. In such a case, the amount of the crosslinked organic silicon resin (A) added is preferably in the range of 0.1 mass % to 20 mass % or more, preferably 0.1 mass % to 10 mass %, relative to the entire cosmetic. If the amount is less than 0.1 mass %, sufficient emulsification performance is not obtained, and if the amount is more than 20 mass %, the feeling on use may deteriorate.

[Other Components]

The cosmetic of the present invention may contain various components used in conventional cosmetics as other components. As the other components, for example, (B) an aqueous ingredient, (C) an oil agent, (D) a powder, (E) a surfactant, (F) a crosslinked organopolysiloxane, (G) a film-forming agent, and (I) other additives may be included. One of these may be used alone, or two or more of them may be used in combination as appropriate. These ingredients are selectively used as appropriate according to the type of cosmetic, and also, the added amount may be a known amount according to the type of cosmetic.

(B) Aqueous Ingredient

The aqueous ingredient is not particularly limited as long as it may be added to conventional cosmetics. Specific examples of the aqueous ingredient include: water; lower alcohol (i.e., alcohols with 5 carbon atoms or less) such as ethanol (INCI: Alcohol); sugar alcohols such as erythritol, maltitol, xylitol, and sorbitol (INCI); humectants including polyhydric alcohols such as butylene glycol (BG, INCI: Butylene Glycol), glycerin, propylene glycol (PG, INCI: Propylene Glycol), dipropylene glycol (DPG, INCI: Dipropylene Glycol), and pentylene glycol (INCI). One kind may be used alone, or two or more kinds may be used in combination as appropriate. When the aqueous ingredient is added, the amount is preferably 0.1 mass % to 90 mass % in the cosmetic.

(C) Oil Agent

An oil agent may be added to the cosmetic of the present invention. The oil agent may be volatile or non-volatile and may be solid, semisolid, or liquid at room temperature (25° C.). Examples of the oil agent include silicone oils, natural vegetable and animal fats and oils, semi-synthetic fats and oils, hydrocarbon oils, higher alcohols (i.e., alcohols with 6 carbon atoms or more), fatty acids, ester oils, fluorine-based oil agents, and ultraviolet absorbers. When the oil agent is added, the amount of the oil agent is not particularly limited but is preferably 1 mass % to 95 mass % or more, preferably 15 mass % to 40 mass %, relative to the entire cosmetic.

Silicone Oil

Examples of the silicone oils include dimethylpolysiloxane (such as KF-96L-1cs, KF-96L-1.5cs, and KF-96L-2cs produced by Shin-Etsu Chemical Co., Ltd.), cyclotetrasiloxane (INCI), cyclopentasiloxane (INCI) (KF-995 produced by Shin-Etsu Chemical Co., Ltd), cyclohexasiloxane (INCI), methyl trimethicone (INCI) (TMF-1.5 produced by Shin-Etsu Chemical Co., Ltd), caprylyl methicone (INCI), phenyl trimethicone (INCI), diphenyl dimethicone (INCI) (KF-54 and KF-54HV produced by Shin-Etsu Chemical Co., Ltd), diphenylsiloxy phenyl trimethicone (KF-56A produced by Shin-Etsu Chemical Co., Ltd.), methylhexylpolysiloxane, methyl hydrogen polysiloxane, linear or branched organopolysiloxane with low to high viscosity such as a dimethylsiloxane-methylphenylsiloxane copolymer, amino-modified organopolysiloxane, pyrrolidone-modified organopolysiloxane, pyrrolidone-carboxylic-acid-modified organopolysiloxane, silicone rubbers such as gum-like dimethicone (INCI) with a high degree of polymerization, gum-like amino-modified organopolysiloxane, and a gum-like dimethylsiloxane-methylphenylsiloxane copolymer, solutions of silicone gum or rubber in cyclic organopolysiloxane, amino acid-modified silicones, fluorine-modified silicones, silicone resins, and solutions of silicone resin.

Solid Oily Ingredient

In the present invention, when solidification of the cosmetic is desired, oily ingredients that are solid at 25° C., are preferably added. Oily ingredients that are solid at 25° C.

have melting points of preferably 40° C. or higher or more preferably 60° C. to 110° C. Examples of the oily ingredients include waxes, hydrocarbons, esters, alcohols with 6 carbon atoms or more, and fatty acids with 6 carbon atoms or more. The oily ingredients are not particularly limited as long as they are ingredients that may be added to conventional cosmetics. Specific examples of the oily ingredients include: vegetable waxes such as carnauba wax (INCI: Copernicia Cerifera (Carnauba) Wax), sugarcane wax, candelilla wax (INCI: Euphorbia Cerifera (Candelilla) Wax), purified candelilla wax, rice wax, Japan wax, jojoba wax, kapok wax, rice bran wax, myrica cerifera fruit wax, shea butter, cocoa butter, *Rhus succedanea* fruit wax (INCI: *Rhus Succedanea* Fruit Wax), montan wax (INCI: Montan Wax), and hydrogenated castor oil isostearate; animal waxes such as beeswax, beef tallow, beef bone tallow, lard (INCI: Lard), horse fat (INCI: Horse Fat), mutton tallow, lanolin (INCI: Lanolin), Chinese wax, shellac wax, and whale wax; semi-synthetic waxes such as lanolin ester, lanolin fatty acid ester, and beeswax ester; hardened oils such as hardened castor oil and hardened coconut oil; hydrocarbon waxes such as solid paraffin, polyethylene, ceresin, ozokerite, and microcrystalline wax; wax esters such as synthetic beeswax; amino acid stearyl alcohols such as dioctyldodecyl lauroyl glutamate, dioctyldodecyl lauroyl glutamate, and dioctyldodecyl lauroyl glutamate; alcohols with 6 carbon atoms or more such as behenyl alcohol and cetanol; fatty acids such as stearic acid and behenic acid; and silicone waxes such as acrylic silicone resins of acryl-silicone graft or block copolymers (such as acryl-silicone graft copolymer: KP-561P and KP-562P produced by Shin-Etsu Chemical Co., Ltd.), or derivatives thereof. One kind or two or more kinds selected from these are preferred.

Natural Vegetable and Animal Fats and Oils, as Well as Semi-Synthetic Fats and Oils Examples of the natural vegetable and animal fats and oils, as well as semi-synthetic fats and oils, include: natural vegetable oils such as avocado oil (labeling name) (INCI: *Persea gratissima* (Avocado) Oil), linseed oil (labeling name) (INCI: *Linum usitatissimum* (Linseed) Seed Oil), almond oil (labeling name) (INCI: *Prunus* mygdalus *dulcis* (Sweet Almond) Oil), perilla oil, olive oil (labeling name) (INCI: *Olea europaea* (Olive) Fruit Oil), *Torreya californica* oil (labeling name) (INCI: *Torreya californica* (California Nutmeg) Oil), citronella oil (labeling name) (INCI: *Cymbopogon nardus* (Citronella) Oil), apricot kernel oil (labeling name) (INCI: Kyounin Yu), wheat germ oil (labeling name) (INCI: *Triticum vulgare* (Wheat) Germ Oil), sesame oil (labeling name) (INCI: *Sesamum indicum* (Sesame) Seed Oil), wheat germ oil (labeling name) (INCI: *Triticum vulgare* (Wheat) Germ Oil), rice germ oil (labeling name) (INCI: *Oryza sativa* (Rice) Germ Oil), rice bran oil (labeling name) (INCI: *Oryza sativa* (Rice) Bran Oil), *Camellia kissi* seed oil (labeling name) (INCI: *Camellia kissi* Seed Oil), safflower oil (labeling name) (INCI: *Carthamus tinctorius* (Safflower) Seed Oil), Chinese *paulownia* oil, cinnamon oil, squalane, squalene, soybean oil, tea seed oil, *camellia* oil (labeling name) (INCI: *Camellia japonica* Seed Oil), evening primrose oil (labeling name) (INCI: *Oenothera biennis* (Evening Primrose) Oil), corn oil (INCI: *Zea mays* (Corn) Oil), rapeseed oil (labeling name) (INCI: RAPE SHUSHI YU), Japanese *paulownia* oil, corn germ oil (labeling name) (INCI: *Zea mays* (Corn) Germ Oil), wheat germ oil (labeling name) (INCI: *Triticum vulgare* (Wheat) Germ Oil), persic oil (labeling name) (INCI), palm oil (labeling name) (INCI: *Elaeis guineensis* (Palm) Oil), palm kernel oil (labeling name) (INCI: *Elaeis guineensis* (Palm) Kernel Oil), castor oil (labeling name) (INCI: *Ricinus communis* (Castor) Seed Oil), sunflower oil (labeling name) (INCI: *Helianthus annuus* (Sunflower) Seed Oil), grape seed oil (labeling name) (INCI: *Vitis vinifera* (Grape) Seed Oil), jojoba oil (labeling name) (INCI: *Simmondsia chinensis* (Jojoba) Seed Oil), *Macadamia* nut oil (labeling name) (INCI: *Macadamia ternifolia* Seed Oil), meadowfoam oil (labeling name) (INCI: *Limnanthes alba* (Meadowfoam) Seed Oil), cottonseed oil (labeling name) (INCI: *Gossypium herbaceum* (Cotton) Seed Oil), Japan wax kernel oil, coconut oil (labeling name) (INCI: *Cocos nucifera* (Coconut) Oil), and peanut oil (INCI: *Arachis hypogaea* (Peanut) Oil); natural animal oils such as shark liver oil (labeling name) (INCI: Shark Liver Oil), cod liver oil (labeling name) (INCI: Cod Liver Oil), fish liver oil (labeling name) (INCI: Fish Liver Oil), turtle oil (labeling name) (INCI: Turtle Oil), mink oil (labeling name) (INCI: Mink Oil), and egg yolk oil (labeling name) (INCI: Egg Oil); and semi-synthetic fats and oils such as hydrogenated coconut oil (labeling name) (INCI: Hydrogenated Coconut Oil), hardened castor oil (labeling name), castor oil fatty acid methyl ester, and liquid lanolin (INCI: Lanolin Oil).

Liquid Oily Ingredient

Examples of the liquid oily ingredients include hydrocarbon oils, higher fatty acids (i.e., fatty acids with 6 carbon atoms or more), higher alcohols (i.e., alcohols with 6 carbon atoms or more), esters, silicone oils, and fluorine-based oil agents.

Hydrocarbon Oil

Examples of the hydrocarbon oils include linear or branched hydrocarbon oils, and the hydrocarbon oils may be volatile hydrocarbon oils or non-volatile hydrocarbon oils. Specific examples of the hydrocarbon oils include olefin oligomers, isododecane (INCI), dodecane (INCI), isohexadecane (INCI), undecane (INCI), squalane (INCI), squalene (INCI), mineral oil (INCI), polyisobutylene (labeling name), hydrogenated polyisobutene (labeling name) (INCI: Hydrogenated Polyisobutene), and (C13-15) alkane (INCI).

Higher Fatty Acid

Examples of the higher fatty acid include oleic acid (labeling name) (INCI: Oleic Acid), linoleic acid (labeling name) (INCI: Linoleic Acid), linolenic acid (labeling name) (INCI: Linolenic Acid), arachidonic acid (labeling name) (INCI: Arachidonic Acid), eicosapentaenoic acid (EPA) (labeling name) (INCI: Eicosapentaenoic Acid), docosahexaenoic acid (DHA) (labeling name) (INCI: Docosahexaenoic Acid), isostearic acid (labeling name) (INCI: Isostearic Acid), and hydroxystearic acid (labeling name) (INCI: Hydroxystearic Acid).

Higher Alcohols

The higher alcohols are preferably alcohols having 6 carbon atoms or more. Specific examples of the alcohols with 6 carbon atoms or more include oleyl alcohol, isostearyl alcohol, 2-decyltetradecinol, cholesterol, phytosterol, polyoxyethylene cholesterol ether, monostearyl glyceryl ether (batyl alcohol), and monooleyl glyceryl ether (selachyl alcohol).

Ester

Esters are liquid oils in a condensed form of fatty acid having 1 to 20 carbon atoms and alcohol having 1 to 20 carbon atoms, and examples of the esters include monoesters and polyesters such as diesters and triesters. Specific examples of the esters include diisobutyl adipate (labeling name) (INCI: Diisobutyl Adipate), dihexyldecyl adipate (labeling name), diheptylundecyl adipate (labeling name) (INCI: Diheptylundecyl Adipate), monoisostearic acid such as isostearyl isostearate (labeling name) (INCI:

Isostearyl Isostearate), n-alkyl glycol, isocetyl isostearate (labeling name) (INCI: Isocetyl Isostearate), trimethylolpropane triisostearate (labeling name) (INCI: Trimethylolpropane Triisostearate), glycol diethylhexanoate (labeling name) (INCI: Glycol Diethylhexanoate), cetyl ethylhexanoate (labeling name) (INCI: Cetyl Ethylhexanoate), triethylhexanoin (labeling name) (INCI: Triethylhexanoin), trimethylolpropane triethylhexanoate (labeling name) (INCI: Trimethylolpropane Triethylhexanoate), pentaerythrityl tetraethylhexanoate (labeling name) (INCI: Pentaerythrityl Tetraethylhexanoate), cetyl octanoate (labeling name) (INCI: Cetyl Ethylhexanoate), octyldodecyl esters such as octyldodecyl oxystearoyl stearate (labeling name) (INCI: Octyldodecyl Stearoyl Stearate), oleyl oleate (labeling name) (INCI: Oleyl Oleate), octyldodecyl oleate (labeling name) (INCI: Octyldodecyl Oleate), decyl oleate (labeling name) (INCI: Decyl Oleate), neopentyl glycol dioctanoate (labeling name) (INCI: Neopentyl Glycol Diethylhexanoate), neopentyl glycol dicaprate (labeling name) (INCI: Neopentyl Glycol Dicaprate), triethyl citrate (labeling name) (INCI: Triethyl Citrate), diethylhexyl succinate (labeling name) (INCI: Diethylhexyl Succinate), amyl acetate (labeling name) (INCI: Amyl Acetate), ethyl acetate (labeling name) (INCI: Ethyl Acetate), butyl acetate (labeling name) (INCI: Butyl Acetate), isocetyl stearate (labeling name) (INCI: Isocetyl Stearate), butyl stearate (labeling name) (INCI: Butyl Stearate), diisopropyl sebacate (labeling name) (INCI: Diisopropyl Sebacate), diethylhexyl sebacate (labeling name) (INCI: Diethylhexyl Sebacate), cetyl lactate (labeling name) (INCI: Cetyl Lactate), myristyl lactate ((labeling name) (INCI: Myristyl Lactate), isononyl isononanoate (labeling name) (INCI: Isononyl Isononanoate), isotridecyl isononanoate (labeling name) (INCI: Isotridecyl Isononanoate), palmitate esters such as isopropyl palmitate (labeling name) (INCI: Isopropyl Palmitate), ethylhexyl palmitate (labeling name) (INCI: Ethylhexyl Palmitate), hexyldecyl palmitate (labeling name) (INCI: Isocetyl Palmitate, Hexyldecyl Palmitate), cholesteryl hydroxystearate (labeling name) (INCI: Cholesteryl Hydroxystearate), isopropyl myristate (labeling name) (INCI: Isopropyl Myristate), octyldodecyl myristate (labeling name) (INCI: Octyldodecyl Myristate), myristyl myristate (labeling name) (INCI: Myristyl Myristate), ethylhexyl laurate (labeling name) (INCI: Ethylhexyl Laurate), hexyl laurate (labeling name) (INCI: Hexyl Laurate), dioctyldodecyl lauroyl glutamate (labeling name) (INCI: Dioctyldodecyl Lauroyl Glutamate), isopropyl lauroyl sarcosinate (labeling name) (INCI: Isopropyl Lauroyl Sarcosinate), diisostearyl malate (labeling name) (INCI: Diisostearyl Malate), and glyceride oils such as glyceryl acetate (labeling name) (INCI: Glyceryl Acetate) and glyceryl stearate (labeling name) (INCI: Glyceryl Stearate).

Fluorine-Based Oil Agent

Examples of the fluorine-based oil agents include perfluoropolyethers such as polyperfluoromethylisopropyl ether (labeling name) (INCI: Polyperfluoromethylisopropyl Ether) and perfluorocarbons such as perfluorodecalin (labeling name) (INCI: Perfluorodecalin) and perfluorohexane (labeling name) (INCI: Perfluorohexane).

Ultraviolet Absorber

Examples of the ultraviolet absorbers include homosalate (INCI), octocrylene (INCI), t-butyl methoxydibenzoylmethane (labeling name) (INCI: Butyl Methoxydibenzoylmethane), ethylhexyl salicylate (labeling name) (INCI: Ethylhexyl Salicylate), diethylamino hydroxybenzoyl hexyl benzoate (labeling name) (INCI: Diethylamino Hydroxybenzoyl Hexyl Benzoate), oxybenzone-6 (labeling name) (INCI: Benzophenone-6), oxybenzone-9 (labeling name) (INCI: Benzophenone-9), oxybenzone-1 (labeling name) (INCI: Benzophenone-1), polysilicone-15 (INCI), octyl dimethoxybenzylidene dioxoimidazolidine propionate (labeling name) (INCI: Ethylhexyl Dimethoxybenzylidene Dioxoimidazolidine Propionate), oxybenzone-2 (labeling name) (INCI: Benzophenone-2), terephthalylidene dicamphor sulfonic acid (labeling name) (INCI: Terephthalylidene Dicamphor Sulfonic Acid), ethylhexyl triazone (INCI), isopentyl trimethoxycinnamate trisiloxane (labeling name) (INCI: Isopentyl Trimethoxycinnamate Trisiloxane), drometrizole trisiloxane (INCI), ethylhexyl dimethyl PABA (labeling name) (INCI: Ethylhexyl Dimethyl PABA), isopropyl paramethoxycinnamate (labeling name) (INCI: Isopropyl Methoxycinnamate), ethylhexyl methoxycinnamate (labeling name) (INCI: Ethylhexyl Methoxycinnamate), bis-ethylhexyloxyphenol methoxyphenyl triazine (labeling name) (INCI: Bis-Ethylhexyloxyphenol Methoxyphenyl Triazine), oxybenzone-3 (labeling name) (INCI: Benzophenone-3), oxybenzone-4 (labeling name) (INCI: Benzophenone-4), oxybenzone-5 (labeling name) (INCI: Benzophenone-5), phenylbenzimidazole sulfonic acid (labeling name) (INCI: Phenylbenzimidazole Sulfonic Acid), methylene bis-benzotriazolyl tetramethylbutylphenol (labeling name) (INCI: Methylene Bis-Benzotriazolyl Tetramethylbutylphenol), glyceryl ethylhexanoate dimethoxycinnamate (labeling name) (INCI: Glyceryl Ethylhexanoate Dimethoxycinnamate), glyceryl PABA (labeling name) (INCI: Glyceryl PABA), diisopropyl methyl cinnamate (labeling name) (INCI: Diisopropyl Methyl Cinnamate), cinoxate (INCI), and ethylhexyl dimethoxybenzylidene dioxoimidazolidine propionate (labeling name) (INCI: Ethylhexyl Dimethoxybenzylidene Dioxoimidazolidine Propionate). The UVA absorber (e.g., diethylamino hydroxybenzoyl hexyl benzoate (labeling name) (INCI: Diethylamino Hydroxybenzoyl Hexyl Benzoate)) and the UVB absorber (e.g., ethylhexyl methoxycinnamate (labeling name) (INCI: Ethylhexyl Methoxycinnamate)) may be used in combination, and they may be combined arbitrarily.

For the oil agent (C), an ingredient which is highly compatible with the component (A) of the present invention is preferably selected in order to easily dissolve the component (A) of the present invention in cosmetics, and an oil agent which is poorly compatible with the component (A) may also be included in limited formulations or in combination with other compatibilizers.

(D) Powders

The powders are not particularly limited as long as they are ingredients that may be added to conventional cosmetics, and examples thereof include pigments and spherical silicone powders. When the powders are added, the amount of the powders is not particularly limited but is preferably 0.1 mass % to 90 mass % or more, preferably 1 mass % to 35 mass %, relative to the entire cosmetic.

Coloring Pigment

Examples of the coloring pigment include red iron oxide, yellow iron oxide, white titanium oxide, black iron oxide, bengala, ultramarine, Prussian blue, manganese violet, cobalt violet, chromium hydroxide, chromium oxide, cobalt oxide, cobalt titanate, iron oxide-doped titanium oxide, iron titanate, burnt titanium/titanium oxide, lithium/cobalt titanate, cobalt titanate, titanium nitride, iron hydroxide, inorganic brown pigments such as $\gamma$-iron oxide, inorganic yellow pigments such as yellow ochre, and colored pigments such as tar-based dyes in lake form and natural dyes in lake form, and any of them may be used.

The pigment according to the present invention may be spherical, approximately spherical, rod-shaped, spindle-shaped, petal-shaped, strip-shaped, amorphous, or any other shape, and there is no limitation on the geometry of the pigment as long as the pigment may impart color to cosmetics. In terms of concealing performance, pigments having particle diameters, i.e., volume average particle diameters, in the range of 150 nm to 600 nm are preferable. The volume average particle diameters may be measured by TEM. If the volume average particle diameter is less than 150 nm, the concealing performance is low, so the coloring efficiency of cosmetics may be low. If the volume average particle diameter is larger than 600 nm, the feeling on use may deteriorate.

The pigment according to the present invention may be partially or entirely surface-treated with inorganic compounds such as alumina, aluminum hydroxide, silica, and water-containing silica.

The hydrophobization treatment of the coloring pigment which has been subjected to the hydrophobization treatment according to the present invention means a surface treatment of a coloring pigment with a hydrophobization treating agent. The surface hydrophobization treating agent for the coloring pigment according to the present invention is not particularly limited as long as it may impart hydrophobicity, and examples thereof include treating agents such as silicone treating agents, waxes, paraffins, organic fluorine compounds including perfluoroalkyl and phosphate salts, surfactants, amino acids including N-acylglutamic acid, and metal soaps including aluminum stearate and magnesium myristate.

More preferred examples thereof are silicone treating agents that include silanes or silylating agents such as caprylsilane (AES-3083 produced by Shin-Etsu Chemical Co., Ltd.) or trimethoxysilyl dimethicone; silicone oils such as dimethyl silicone (the KF-96A series produced by Shin-Etsu Chemical Co., Ltd.), methylhydrogen type polysiloxanes (KF-99P and KF-9901 produced by Shin-Etsu Chemical Co., Ltd.), and silicone-branched silicone treating agents (KF-9908 and KF-9909 produced by Shin-Etsu Chemical Co., Ltd.); and silicone compounds such as acrylsilicone (KP-574 and KP-541 produced by Shin-Etsu Chemical Co., Ltd.). In particular, silicone powder treating agents described in Japanese Patent No. 3912961 are suitably used, and among them, triethoxysilylethyl polydimethylsiloxyethyl hexyl dimethicone (KF-9909 produced by Shin-Etsu Chemical Co., Ltd.), which is dimethylpolysiloxane having a triethoxysilyl group, a polydimethylsiloxyethyl group, and a hexyl group in the side chain, is effectively used because it exhibits high affinity with a dispersion medium in which a highly hydrophobic coloring pigment according to the present invention is dispersed even if the dispersion medium has a mixed composition of silicones and hydrocarbons.

The surface hydrophobization treating agents may be used alone or in a combination of two or more of them.

In the present invention, the preparation method in which the coloring pigment is surface-treated using the hydrophobization treating agent is not particularly limited, and can be a known method. The surface treatment method may be broadly classified into dry and wet methods. In the dry method, the coloring pigment used in the present invention and the hydrophobization treating agent are mixed and caused to come into contact with each other by using any agitator, grinder, mixer, or disperser, such as a Henschel Mixer, a ball mill, a jet mill, a kneader, a planetary mixer, a sand mill, an Atritor, a ribbon blender, a disper mixer, or a homo-mixer. In this method, the treatment may be performed while heating or applying mechanochemical-like mechanical forces or the energy of superheated steam. Further, the treatment may be performed by separately heating or applying mechanochemical-like mechanical forces or the energy of superheated steam after the coloring pigment and the hydrophobization treating agent are sufficiently mixed and caused to be in contact with each other. When the hydrophobization treating agent is mixed in and caused to be in contact with the coloring pigment, in order to improve dispersion efficiency of the hydrophobization treating agent, the hydrophobization treating agent is dissolved or dispersed in an arbitrary amount of water, solvent, or supercritical fluid in advance, and the resulting solution may be sprayed on the coloring pigment. In the wet method, the treatment may be performed by dispersing the coloring pigment and the hydrophobization treating agent in water, solvent, or supercritical fluid, mixing and causing them to be in contact with each other, evaporating the solvent, and then separately heating or applying mechanochemical-like mechanical forces or the energy of superheated steam.

Specific examples of the coloring pigment that underwent a surface hydrophobization treatment include the KTP-09 series, particularly KTP-09W, KTP-09R, KTP-09Y, KTP-09B, and the like (produced by Shin-Etsu Chemical Co., Ltd.).

Inorganic Powder

Examples of the inorganic powders include microparticles of zirconium oxide, zinc oxide, cerium oxide, magnesium oxide, barium sulfate, calcium sulfate, magnesium sulfate, calcium carbonate, magnesium carbonate, talc, cleaved talc, mica, kaolin, sericite, muscovite, synthetic mica, phlogopite, trilithionite, biotite, lepidolite, silicic acid, silicon dioxide, fumed silica, hydrous silicon dioxide, aluminum silicate, magnesium silicate, aluminum magnesium silicate, calcium silicate, barium silicate, strontium silicate, tungstic acid metal salts, hydroxyapatite, vermiculite, hydrargilite, bentonite, montmorillonite, hectorite, zeolite, ceramic, dicalcium phosphate, alumina, aluminum hydroxide, boron nitride, boron nitride, and glass. Further, examples of inorganic colored pearl pigments include pearl pigments such as titanium oxide-coated mica, bismuth oxychloride, titanium oxide-coated bismuth oxychloride, titanium oxide-coated talc, fish scales, and titanium oxide-coated colored mica. Examples of microparticulate metal oxides include one or at least two kinds selected from microparticulate titanium oxide (INCI), microparticulate iron-containing titanium oxide, microparticulate zinc oxide (INCI), microparticulate cerium oxide (INCI), and composites thereof. These metal oxides may be composite powders with other powders. The average primary particle diameter is preferably 200 nm or less or more preferably 120 nm or less. If the particle diameter is larger than the aforesaid upper limit, the defensive function against UV rays decreases, causing a white residue. The average primary particle diameter may be determined using transmission electron microscope photographs.

The above-described microparticulate metal oxides are not particularly limited even if they are unprocessed or processed with a known surface treatment used for the cosmetic. Further, the microparticulate metal oxides may be dispersing elements that are preliminarily dispersed in volatile oil agents or ester oils. Specific examples of the dispersing elements include the SPD series, particularly SPD-T5, SPD-T5L, SPD-T6, SPD-T7, SPD-Z5, SPD-Z5L, and the like (produced by Shin-Etsu Chemical Co., Ltd.).

Metal Powder

Examples of metal powders include metal microparticles made of aluminum, copper, stainless steel, silver, and the like.

Organic Powder

Examples of the organic powders include powders made of silicone, polyamide, polyacrylic acid-acrylate esters, polyester, polyethylene, polypropylene, polystyrene, styrene-acrylic acid copolymers, divinylbenzene-styrene copolymers, polyurethane, vinyl resins, urea formaldehyde resins, melamine resins, benzoguanamine, polymethyl benzoguanamine, tetrafluoroethylene, polymethyl methacrylates (such as polymethyl methacrylate), cellulose, silk, nylon, phenolic resins, epoxy resins, polycarbonate, and the like. Specific examples of those made of silicone include silicone resin particles (as specific examples, KMP-590, KMP-591, KMP-592, and the like produced by Shin-Etsu Chemical Co., Ltd.) and silicone resin-coated silicone rubber powders (as specific examples, KSP-100, KSP-101, KSP-102, KSP-105, KSP-300, KSP-411, KSP-441, and the like produced by Shin-Etsu Chemical Co., Ltd.), and they may preliminarily be dispersed in water or in oil. Metal soaps and the like are also included, and specific examples include powders of zinc stearate, aluminum stearate, calcium stearate, magnesium stearate, zinc myristate, magnesium myristate, zinc cetyl phosphate, calcium cetyl phosphate, zinc sodium cetyl phosphate, and the like. Organic pigments and the like are also included, and specific examples include synthetic pigments (tar pigments) such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207, and natural dyes such as carminic acid, laccaic acid, carthamin, brazilin, and crocin.

Inorganic/Organic Composite Powder

Examples of inorganic/organic composite powders include composite powders in the form of inorganic powders with surfaces coated with organic powders by a publicly known and used method.

As the powders described above, those with treated particle surfaces may be used. Further, the surface treating agent preferably imparts hydrophobicity in respect to the water resistance of cosmetics. The treating agent that imparts hydrophobicity is not particularly limited, and examples of the treating agent include silicone treating agents, waxes, paraffins, organofluorine compounds such as perfluoroalkyl group-modified phosphates, surfactants, amino acids such as N-acylglutamic acid, and metal soaps such as aluminum stearate and magnesium myristate. More preferred are silicone treating agents. Examples include silanes or silylating agents such as triethoxycaprylylsilane (INCI) (AES-3083 produced by Shin-Etsu Chemical Co., Ltd.) or trimethoxysilyl dimethicone (INCI), silicone oils such as dimethylsilicones (the KF-96A series produced by Shin-Etsu Chemical Co., Ltd.), methylhydrogen type polysiloxanes (KF-99P, KF-9901, and the like produced by Shin-Etsu Chemical Co., Ltd.) such as hydrogen dimethicone (INCI), silicone branched silicone treating agents (KF-9908, KF-9909, and the like produced by Shin-Etsu Chemical Co., Ltd.), and acrylic silicones (KP-574 and KP-541 produced by Shin-Etsu Chemical Co., Ltd.). The surface hydrophobization treating agents may be used alone or in a combination of two or more of them.

(E) Surfactant

Examples of the surfactant include nonionic, anionic, cationic, and ampholytic surfactants, and any of the surfactants which are used in conventional cosmetics may be used to the extent that the surfactants do not impair the effects of the present invention. Among these surfactants, preferred are partially crosslinked polyether-modified silicones, partially crosslinked polyglycerol-modified silicones, linear or branched polyoxyethylene-modified organopolysiloxanes, linear or branched polyoxyethylene polyoxypropylene-modified organopolysiloxanes, linear or branched polyoxyethylene/alkyl co-modified organopolysiloxanes, linear or branched polyoxyethylene polyoxypropylene/alkyl co-modified organopolysiloxanes, linear or branched polyglycerol-modified organopolysiloxanes, linear or branched polyglycerol/alkyl co-modified organopolysiloxanes, and linear or branched pyrrolidone-modified organopolysiloxanes. In these surfactants, the content of hydrophilic polyoxyethylene groups, polyoxyethylene polyoxypropylene groups, or polyglycerol residues is preferably 10 mass % to 70 mass % of the molecule. When a partially crosslinked polyether-modified silicone or partially crosslinked polyglycerol-modified silicone is used, in the compositions comprising the crosslinked organopolysiloxane and an oil agent which is liquid at room temperature, it is preferred that the crosslinked organopolysiloxane swells in respect to the liquid oil by containing an amount of its own weight or more of the liquid oil agent. As the liquid oil agent, liquid silicones, hydrocarbon oils, ester oils, natural vegetable and animal oils, semi-synthetic oils, and fluorine-based oils, each of which is an optional ingredient in an oil agent, may be used. Examples of the liquid oil agent include low viscosity silicones having a kinematic viscosity at 25° C. of 0.65 $mm^2/s$ to 100 $mm^2/s$, hydrocarbon oils such as liquid paraffin, squalane, isododecane, and isohexadecane, glyceride oils such as triethylhexanoin, ester oils such as isotridecyl isononanoate, and natural vegetable and animal oils such as jojoba oil. Specific examples of the crosslinked organopolysiloxane include KSG-210, KSG-240, KSG-310, KSG-320, KSG-330, KSG-340, KSG-320Z, KSG-350Z, KSG-710, KSG-810, KSG-820, KSG-830, KSG-840, KSG-820Z, and KSG-850Z produced by Shin-Etsu Chemical Co., Ltd. Specific examples of the non-crosslinked organopolysiloxane include KF-6011, KF-6013, KF-6043, KF-6017, KF-6028, KF-6038, KF-6048, KF-6100, KF-6104, KF-6105, and KF-6106 produced by Shin-Etsu Chemical Co., Ltd. In any case, the amount of the surfactant is preferably 0.1 mass % to 20 mass %, relative to an entire cosmetic. The crosslinked organopolysiloxane, the non-crosslinked organopolysiloxane, or one or more of both may be selected appropriately, to the extent that the surfactants do not impair the effects of the present invention.

(F) Crosslinked Organopolysiloxane

The crosslinked organopolysiloxane is not particularly limited as long as it is used in conventional cosmetic products. One kind may be used alone, or two or more kinds may be used in combination as appropriate. Unlike the silicone powders described in the above (D), the crosslinked organopolysiloxane does not have a spherical shape. Further, unlike the surfactant (E), the crosslinked organopolysiloxane is a compound that does not have a polyether or polyglycerol structure in the molecular structure. The crosslinked organopolysiloxane is an elastomer that has a structural viscosity by swelling with the oil agent (B). Specific examples of the crosslinked organopolysiloxane include dimethicone/vinyl dimethicone crosspolymers, dimethicone/phenyl vinyl dimethicone crosspolymers, vinyl dimethicone/lauryl dimethicone crosspolymers, and lauryl polydimethylsiloxyethyl dimethicone/bis-vinyldimethicone crosspolymers, which are defined by cosmetic product labeling names. These are commercially available as swollen materials comprising a liquid oil at room temperature, and specific examples include KSG-15, KSG-1510, KSG-16, KSG-1610, KSG-18A, KSG-19, KSG-41A, KSG-42A, KSG-43, KSG-44, KSG-042Z, KSG-045Z, and KSG-048Z produced by Shin-Etsu Chemical Co., Ltd. When this ingredient is comprised, the amount is preferably 0.01 mass % to 30 mass % in a cosmetic as a solid.

(G) Film-Forming Agent

The film-forming agent is not particularly limited as long as it is an ingredient that may be added to conventional cosmetics. Specifically, examples of the film-forming agent include latexes such as polyvinyl alcohol, polyvinyl pyrrolidone, polyvinyl acetate, and alkyl polyacrylate, cellulose derivatives such as dextrin, alkyl cellulose, and nitrocellulose, siliconized polysaccharide compounds such as trimethylsiloxysilylcarbamoyl pullulan, acrylic-silicone-based graft copolymers such as alkyl acrylate/dimethicone copolymers, silicone resins such as trimethylsiloxysilicate, silicone-based resins such as silicone-modified polynorbornene and fluorine-modified silicone resins, fluororesins, aromatic hydrocarbon resins, polymer emulsion resins, terpene-based resins, polybutene, polyisoprene, alkyd resins, polyvinylpyrrolidone-modified polymers, rosin-modified resins, and polyurethane.

Among these, silicone-based film-forming agents are particularly preferred, and among them, although not limited, trimethylsiloxysilylcarbamoyl pullulan (dissolved in solvents available as TSPL-30-D5 and TSPL-30-ID produced by Shin-Etsu Chemical Co., Ltd. as commercially available products), alkyl acrylate/dimethicone copolymers (dissolved in solvents available as KP-543, KP-545, KP-549, KP-550, KP-545L, and the like produced by Shin-Etsu Chemical Co., Ltd. as commercially available products), trimethylsiloxysilicate (dissolved in solvents available as KF-7312J, X-21-5250, and the like produced by Shin-Etsu Chemical Co., Ltd. as commercially available products), silicone-modified polynorbornene (dissolved in solvents available as NBN-30-ID and the like produced by Shin-Etsu Chemical Co., Ltd. as commercially available products), and organosiloxane graft polyvinyl alcohol-based polymers may be used. As the film-forming agent, one or at least two kinds may be used. When this ingredient is added, the amount is preferably 0.1 mass % to 20 mass % in a cosmetic.

(I) Other Additives

Examples of the other additives include an oil-soluble gelling agent, water-soluble thickener, antiperspirant, preservative and antimicrobial, perfume, salt, antioxidant, pH adjuster, chelator, cooling agent, anti-inflammatory agent, skincare ingredient (such as a skin-brightening agent, cell activator, rough skin improver, blood circulation promoter, skin astringent, or antiseborrheic agent), vitamin, amino acid, water-soluble polymer compound, fiber, and inclusion compound.

Oil-Soluble Gelling Agent

Examples of the oil-soluble gelling agent include: metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitic acid ester, dextrin stearic acid ester, and dextrin 2-ethylhexanoic acid/palmitic acid ester; sucrose fatty acid esters such as sucrose palmitic acid ester and sucrose stearic acid ester; fructo-oligosaccharide fatty acid esters such as fructo-oligosaccharide stearic acid ester and fructo-oligosaccharide 2-ethylhexanoic acid ester; benzylidene derivatives of sorbitol such as monobenzylidene sorbitol and dibenzylidene sorbitol; and organic-modified clay minerals of disteardimonium hectorite, stearalkonium hectorite, and hectorite.

Water-Soluble Thickener

Examples of the water-soluble thickener include plant polymers such as gum arabic, tragacanth, galactan, carob gum, guar gum, gum karaya, carrageenan, pectin, agar, quince seed (marmelo), starch (such as rice, corn, potato, or wheat), algae colloid, trant gum, and locust bean gum; microbial polymers such as xanthan gum, dextran, succinoglucan, and pullulan; animal polymers such as collagen, casein, albumin, and gelatin; starch polymers such as carboxymethyl starch and methyl hydroxypropyl starch; cellulose polymers such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, cationized cellulose, and cellulose powder; alginic acid polymers such as sodium alginate and propylene glycol alginate ester; vinyl polymers such as polyvinyl methyl ether and carboxy vinyl polymer; polyoxyethylene polymers; polyoxyethylene polyoxypropylene copolymer polymers; acryl polymers such as sodium polyacrylate, polyethyl acrylate, polyacrylamide, and acryloyldimethyl taurate salt copolymer; other synthetic water-soluble polymers such as polyethyleneimine and cationic polymer; and inorganic water-soluble polymers such as bentonite, aluminum magnesium silicate, montmorillonite, beidellite, nontronite, saponite, hectorite, and anhydrous silicic acid.

Among them, one or more water-soluble thickeners selected from plant polymers, microbial polymers, animal polymers, starch polymers, cellulose polymers, alginic acid polymers, polyoxyethylene polyoxypropylene copolymer polymers, acryl polymers, and inorganic water-soluble polymers are preferably used.

Antiperspirant

Examples of the antiperspirant include aluminum hydroxyhalides such as chlorohydroxy aluminum; aluminum halides such as aluminum chloride; aluminum allantoinate, tannic acid, persimmon tannin, aluminum/potassium sulfate, zinc oxide, zinc para-phenolsulfonate, burnt alum, aluminum/zirconium tetrachlorohydrate, and aluminum/zirconium trichlorohydrex glycine. In particular, as ingredients that are highly effective, an aluminum hydroxyhalide, an aluminum halide, a complex or mixture thereof with zirconyl oxyhalide and zirconyl hydroxyhalide (for example, aluminum/zirconium tetrachlorohydrate and aluminum/zirconium trichlorohydrex glycine), and the like are preferable.

Preservative and Antimicrobial

Examples of the preservative and antimicrobial include para-oxybenzoate alkyl ester, benzoic acid, sodium benzoate, sorbic acid, potassium sorbate, phenoxy ethanol, imidazolidinyl urea, salicylic acid, isopropylmethylphenol, carbolic acid, p-chloro-m-cresol, hexachlorophene, benzalkonium chloride, chlorhexidine chloride, trichlorocarbanilide, iodopropynyl butylcarbamate, polylysine, photosensitizers, silver, and plant extracts.

Perfume

Examples of the perfume include natural perfumes and synthetic perfumes. Examples of the natural perfumes include plant perfumes separated from flowers, leaves, wood, pericarp, and the like, and animal perfumes such as musk and civet. Examples of the synthetic perfumes include hydrocarbons such as monoterpene; alcohols such as aliphatic alcohol and aromatic alcohol; aldehydes such as terpene aldehyde and aromatic aldehyde; ketones such as alicyclic ketone; esters such as terpene-based ester; lactones; phenols; oxides; nitrogen-containing compounds; and acetals.

Salt

Examples of the salt include inorganic salts, organic acid salts, amine salts, and amino acid salts. Examples of the inorganic salts include a sodium salt, potassium salt, magnesium salt, calcium salt, aluminum salt, zirconium salt, zinc salt, and the like of inorganic acids such as hydrochloric acid, sulfuric acid, carbonic acid, and nitric acid. Examples of the organic acid salts include salts of organic acids such as acetic acid, dehydroacetic acid, citric acid, malic acid, succinic acid, ascorbic acid, and stearic acid. Examples of the amine salts and the amino acid salts include salts of amines such as triethanolamine and salts of amino acids such as glutamic acid. In addition, as others, a salt of hyaluronic acid, chondroitin sulfate, or the like, and further an acid-alkali neutralizing salt or the like to be used in preparation formulation may also be used.

Antioxidant

Examples of the antioxidant include, but are not particularly limited to, carotenoid, ascorbic acid and a salt thereof, ascorbyl stearate, tocophenol, tocophenol acetate, tocopherol, p-t-butylphenol, butylhydroxyanisole, dibutyl hydroxytoluene, phytic acid, ferulic acid, thiotaurine, hypotaurine, sulfite, erythorbic acid and a salt thereof, chlorogenic acid, epicatechin, epigallocatechin, epigallocatechin gallate, apigenin, kaempferol, myricetin, and quercetin.

pH Adjuster

Examples of the pH adjuster include lactic acid, citric acid, glycolic acid, succinic acid, tartaric acid, dl-malic acid, potassium carbonate, sodium bicarbonate, and ammonium bicarbonate.

Chelator

Examples of the chelator include alanine, sodium edetate, sodium polyphosphate, sodium metaphosphate, and phosphoric acid.

Cooling Agent

Examples of the cooling agent include L-menthol, camphor, and menthyl lactate.

Anti-Inflammatory Agent

Examples of the anti-inflammatory agent include allantoin, glycyrrhizinic acid and a salt thereof, glycyrrhetinic acid and stearyl glycyrrhetinate, tranexamic acid, and azulene.

Skincare Ingredient

Examples of the skincare ingredient include skin-brightening agents such as arbutin, hydroquinone, tranexamic acid, ascorbic acid derivatives, glutathione, and strawberry geranium extract; cell activators such as royal jelly, photosensitizer, cholesterol derivatives, and calf blood extract; rough skin improvers; blood circulation promoters such as vanillylamide nonylate, benzyl nicotinate, β-butoxyethyl nicotinate, capsaicin, zingerone, tincture of cantharides, ichthammol, caffeine, tannic acid, α-borneol, tocopherol nicotinate, inositol hexanicotinate, cyclandelate, cinnarizine, tolazoline, acetylcholine, verapamil, cepharanthine, and γ-oryzanol; skin astringents; and antiseborrheic agents such as sulfur and thianthrol.

Vitamins

Examples of the vitamin include vitamin A such as vitamin A oil, retinol, retinyl acetate, and retinyl palmitate; vitamin B including vitamin $B_2$ such as riboflavin, riboflavin butyrate, and flavin adenine nucleotide, vitamin $B_6$ such as pyridoxine hydrochloride, pyridoxine dioctanoate, and pyridoxine tripalmitate, vitamin $B_{12}$ and a derivative thereof, and vitamin $B_{15}$ and a derivative thereof; vitamin C such as L-ascorbic acid, L-ascorbic acid dipalmitate, sodium L-ascorbic acid-2-sulfate, and dipotassium L-ascorbic acid diphosphate; vitamin D such as ergocalciferol and cholecalciferol; vitamin E such as α-tocopherol, β-tocopherol, γ-tocopherol, dl-α-tocopherol acetate, dl-α-tocopherol nicotinate, and dl-α-tocopherol succinate; nicotinic acids such as nicotinic acid, benzyl nicotinate, and amide nicotinate; pantothenic acids such as vitamin H, vitamin P, calcium pantothenate, D-pantothenyl alcohol, pantothenyl ethyl ether, and acetyl pantothenyl ethyl ether; and biotin.

Amino Acid

Examples of the amino acid include glycine, valine, leucine, isoleucine, serine, threonine, phenylalanine, arginine, lysine, aspartic acid, glutamic acid, cystine, cysteine, methionine, and tryptophan.

Nucleic Acid

Examples of a nucleic acid include deoxyribonucleic acid and the like.

Hormone

Examples of a hormone include estradiol, ethenyl estradiol, and the like.

Inclusion Compound

Examples of the inclusion compound include cyclodextrin and the like.

The cosmetics described may be either an emulsion or non-aqueous composition. When it is desired to impart a fresh feeling on use, the emulsion is selected. The emulsion may be an oil-in-water (O/W) type emulsion, water-in-oil (W/O) type emulsion, oil-in-water-in-oil (O/W/O) type emulsion, or water-in-oil-in-water (W/O/W) type emulsion. When it is desired to yield an oily feeling or water resistance, a non-aqueous composition or powder composition may be selected. In both cases, satisfactory cosmetics may be obtained. Note that in the present invention, the non-aqueous compositions means a composition in which water is not purposely added. Among these, the non-aqueous composition with which an especially high oil resistance may be expected is preferable.

The crosslinked organic silicon resin of the present invention may be included in cosmetics using various methods. For example, the crosslinked organic silicon resin may be mixed in an oil phase, aqueous phase, or both to be used as an emulsifier, feeling on use adjuster, thickener, compatibilizer, or insolubilizer, or may be used as a dispersant for powder.

The cosmetic of the present invention is not particularly limited and may be used in a variety of products including beauty essences, milky lotions, creams, hair care products, foundations, makeup bases, sunscreens, concealers, blush, lipsticks, lip glosses, lip balms, mascaras, eye shadows, eye liners, body makeups, deodorants, and cosmetics for nails. In particular, makeup cosmetics such as milky lotions, creams, hair care products, and foundations and cosmetics having sunscreen effects are preferable among them. The cosmetic of the present invention may be in any of a variety of forms such as a liquid, cream, solid, paste, gel, mousse, soufflé-like form, clay, powder, and stick.

EXAMPLES

The following describes the present invention in more detail by means of Preparation Examples, Examples, Comparative Examples, but the present invention is not limited by the following Preparation Examples and Examples. "%" in composition is mass % unless otherwise specified. Examples of the crosslinked organic silicon resin are Preparation Examples, and examples of the cosmetics are Examples and Comparative Examples. In the following description, the hydrosilyl group-containing organic silicon resin, which is an ingredient, is one obtained by synthesis based on the preparation method described in Japanese Patent Application Laid-Open No. 2017-75283.

Preparation Example 1

Method for Preparing Crosslinked Organic Silicon Resin

To a reactor, 1,000 g of 50% solution of powdery hydrosilyl group-containing organic silicon resin represented by the following average composition formula (E1) (weight-average molecular weight: 3,310, the amount of hydrosilyl group: 2.03 mmol/g) in decamethylcyclopentasiloxane, 83.5 g of polyoxyalkylene having allyl groups at both ends, represented by the following formula (E2), 795.8 g of 2-propanol, and 1.1 g of 0.5% solution of chloroplatinic acid in ethanol were added, and the reaction was conducted by heating at 80° C. for three hours. After confirming the reaction, 508.1 g of organopolysiloxane having a vinyl group at one end, represented by the following formula (E3) was added, and the resultant was heated at 80° C. for three hours. Thereafter, 79.6 g of 2% aqueous citric acid solution was added, and the resultant was heated at 80° C. for three hours to hydrolyze an allylether group of unreacted polyoxyalkylene, and the resultant was neutralized with 48.2 g of 5% sodium bicarbonate water. A reaction product was heated under reduced pressure to distill off the solvent, and was then filtrated. Thus, a solution of the crosslinked organic silicon resin represented by the following formula (E4) in decamethylcyclopentasiloxane was obtained.

Average Composition Formula (E1):

$$(Me_3SiO_{1/2})_{18.3}(HMe_2SiO_{1/2})_{7.8}(SiO_2)_{21.8}$$

formula (E2)

$$CH_2{=}CH{-}CH_2{-}O{-}(C_2H_4O)_{10}{-}CH_2{-}CH{=}CH_2$$

formula (E3)

$$CH_2{=}CH{-}(SiO(CH_3)_2)_8{-}Si(CH_3)_3$$

Average Composition Formula (E4):

$$(Me_3SiO_{1/2})_{18.3}(X_{1/2}Me_2SiO_{1/2})_{2.6}(R^3Me_2SiO_{1/2})_{12.8}(SiO_{4/2})_{43.5}$$

$$X{=}{-}CH_2{-}CH{-}CH_2{-}O{-}(C_2H_4O)_{10}{-}CH_2{-}CH{-}CH_2{-}$$

$$R^3{=}{-}CH_2{-}CH_2{-}(SiO(CH_3)_2)_8{-}Si(CH_3)_3$$

wherein Me represents a methyl group, hereinafter the same. In the formula (E4), some of X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was a colorless transparent liquid (weight-average molecular weight: 47,600).

The HLB of the product was 1.8.

Preparation Example 2

Method for Preparing Crosslinked Organic Silicon Resin

To a reactor, 700 g of 50% solution of powdery hydrosilyl group-containing organic silicon resin represented by the average composition formula (E5) (weight-average molecular weight: 3,200, the amount of hydrosilyl group: 1.97 mmol/g) in decamethylcyclopentasiloxane, 60.6 g of polyoxyalkylene having allyl groups at both ends, represented by the following formula (E6), 547.3 g of 2-propanol, and 0.7 g of 0.5% solution of chloroplatinic acid in ethanol were added, and the reaction was conducted by heating at 80° C. for three hours. After confirming the reaction, 334.1 g of organopolysiloxane having a vinyl group at one end, represented by the following formula (E7) was added, and the resultant was heated at 80° C. for three hours. Thereafter, 54.7 g of 2% aqueous citric acid solution was added, and the resultant was heated at 80° C. for three hours to hydrolyze an allylether group of unreacted polyoxyalkylene, and the resultant was neutralized with 33.1 g of 5% sodium bicarbonate water. A reaction product was heated under reduced pressure to distill off the solvent, and was then filtrated. Thus, a solution of the crosslinked organic silicon resin represented by the following formula (E8) in decamethylcyclopentasiloxane was obtained.

Average Composition Formula (E5):

$$(Me_3SiO_{1/2})_{17.7}(HMe_2SiO_{1/2})_{7.6}(SiO_2)_{21.0}$$

formula (E6)

$$CH_2{=}CH{-}CH_2{-}O{-}(C_2H_4O)_{10}{-}CH_2{-}CH{=}CH_2$$

formula (E7)

$$CH_2{=}CH{-}(SiO(CH_3)_2)_8{-}Si(CH_3)_3$$

Average Composition Formula (E8):

$$(Me_3SiO_{1/2})_{17.17}(X_{1/2}Me_2SiO_{1/2})_{2.7}(R_3Me_2SiO_{1/2})_{4.9}(SiO_{4/2})_{21.0}$$

$$X={-}CH_2{-}CH{-}CH_2{-}O{-}(C_2H_4O)_{10}{-}CH_2{-}CH{-}CH_2{-}$$

$$R^3={-}CH_2{-}CH_2{-}(SiO(CH_3)_2)_8{-}Si(CH_3)_3$$

wherein Me represents a methyl group, hereinafter the same. In the formula (E8), some of X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was a colorless transparent liquid (weight-average molecular weight: 63,500).

The HLB of the product was 1.9.

Preparation Example 3

Method for Preparing Crosslinked Organic Silicon Resin

To a reactor, 1,500 g of 50% solution of powdery hydrosilyl group-containing organic silicon resin represented by the average composition formula (E9) (weight-average molecular weight: 3,160, the amount of hydrosilyl group: 1.99 mmol/g) in decamethylcyclopentasiloxane, 626.9 g of organopolysiloxane having a vinyl group at one end, represented by the following formula (E10), 1,144.2 g of 2-propanol, and 1.5 g of 0.5% solution of chloroplatinic acid in ethanol were added, and the reaction was conducted by heating at 80° C. for three hours. After confirming the reaction, 161.6 g of polyoxyalkylene having an allyl group at one end, represented by the following formula (E11) was added, and the resultant was heated at 80° C. for three hours. Thereafter, 114.4 g of 2% aqueous citric acid solution was added, and the resultant was heated at 80° C. for three hours to hydrolyze an allylether group of unreacted polyoxyalkylene, and the resultant was neutralized with 69.3 g of 5% sodium bicarbonate water. A reaction product was heated under reduced pressure to distill off the solvent, and was then filtrated. Thus, a solution of the crosslinked organic silicon resin represented by the following formula (E12) in decamethylcyclopentasiloxane was obtained.

Average Composition Formula (E9):

$$(Me_3SiO_{1/2})_{17.9}(HMe_2SiO_{1/2})_{5.7}(SiO_2)_{22.1}$$

$$CH_2{=}CH{-}(SiO(CH_3)_2)_8{-}Si(CH_3)_3 \quad \text{formula (E10)}$$

$$CH_2{=}CH{-}CH_2{-}O{-}(C_2H_4O)_{10}{-}CH_2{-}CH{=}CH_2 \quad \text{formula (E11)}$$

Average Composition Formula (E12):

$$(Me_3SiO_{1/2})_{17.9}(X_{1/2}Me_2SiO_{1/2})_{2.5}(R^3Me_2SiO_{1/2})_{3.2}(SiO_{4/2})_{22.1}$$

$$X{=}{-}CH_2{-}CH{-}CH_2{-}O{-}(C_2H_4O)_{10}{-}CH_2{-}CH{-}CH_2{-}$$

$$R^3{=}{-}CH_2{-}CH_2{-}(SiO(CH_3)_2)_8{-}Si(CH_3)_3$$

wherein Me represents a methyl group, hereinafter the same. In the formula (E12), some X may be a hydroxyl group.

A solution of the obtained crosslinked organic silicon resin in decamethylcyclopentasiloxane was heated at 120° C. to 130° C. under reduced pressure to remove decamethylcyclopentasiloxane. The resultant product was a colorless transparent liquid (weight-average molecular weight: 66,500).

The HLB of the product was 2.2.

Preparation Example 4

Method for Preparing Crosslinked Organic Silicon Resin

To a reactor, 400 g of 50% solution of powdery hydrosilyl group-containing organic silicon resin represented by the average composition formula (E13) (weight-average molecular weight: 5,420, the amount of hydrosilyl group: 1.95 mmol/g) in decamethylcyclopentasiloxane, 24.0 g of polyoxyalkylene having allyl groups at both ends, represented by the following formula (E14), 321.5 g of 2-propanol, and 0.4 g of 0.5% solution of chloroplatinic acid in ethanol were added, and the reaction was conducted by heating at 80° C. for three hours. After confirming the reaction, 219.0 g of organopolysiloxane having a vinyl group at one end, represented by the following formula (E15) was added, and the resultant was heated at 80° C. for three hours. Thereafter, 32.2 g of 2% aqueous citric acid solution was added, and the resultant was heated at 80° C. for three hours to hydrolyze an allylether group of unreacted polyoxyalkylene, and the resultant was neutralized with 19.5 g of 5% sodium bicarbonate water. A reaction product was heated under reduced pressure to distill off the solvent, and was then filtrated. Thus, a solution of the crosslinked organic silicon resin represented by the following formula (E16) in decamethylcyclopentasiloxane was obtained.

Average Composition Formula (E13):

$$(Me_3SiO_{1/2})_{27.7}(HMe_2SiO_{1/2})_{11.9}(SiO_2)_{39.6}$$

-continued $$CH_2{=}CH{-}CH_2{-}O{-}(C_2H_4O)_{10}{-}CH_2{-}CH{=}CH_2 \quad \text{formula (E14)}$$

$$CH_2{=}CH{-}(SiO(CH_3)_2)_8{-}Si(CH_3)_3 \quad \text{formula (E15)}$$

Average Composition Formula (E16):

$$(Me_3SiO_{1/2})_{27.7}(X_{1/2}Me_2SiO_{1/2})_{3.0}(R^3Me_2SiO_{1/2})_{8.9}(SiO_{4/2})_{39.6}$$

$$X{=}{-}CH_2{-}CH{-}CH_2{-}O{-}(C_2H_4O)_{10}{-}CH_2{-}CH{-}CH_2{-}$$

$$R^3{=}{-}CH_2{-}CH_2{-}(SiO(CH_3)_2)_8{-}Si(CH_3)_3$$

wherein Me represents a methyl group, hereinafter the same. In the formula (E16), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was a colorless transparent liquid (weight-average molecular weight: 48,100).

The HLB of the product was 1.3.

Preparation Example 5

Method for Preparing Crosslinked Organic Silicon Resin

To a reactor, 1,300 g of 50% solution of powdery hydrosilyl group-containing organic silicon resin represented by the average composition formula (E17) (weight-average molecular weight: 5,420, the amount of hydrosilyl group: 1.95 mmol/g) in decamethylcyclopentasiloxane, 93.7 g of polyoxyalkylene having allyl groups at both ends, represented by the following formula (E18), 1,029.0 g of 2-propanol, and 1.4 g of 0.5% solution of chloroplatinic acid in ethanol were added, and the reaction was conducted by heating at 80° C. for three hours. After confirming the reaction, 664.2 g of organopolysiloxane having a vinyl group at one end, represented by the following formula (E19) was added, and the resultant was heated at 80° C. for three hours. Thereafter, 102.9 g of 2% aqueous citric acid solution was added, and the resultant was heated at 80° C. for three hours to hydrolyze an allylether group of unreacted polyoxyalkylene, and the resultant was neutralized with 62.3 g of 5% sodium bicarbonate water. A reaction product was heated under reduced pressure to distill off the solvent, and was then filtrated. Thus, a solution of the crosslinked organic silicon resin represented by the following formula (E20) in decamethylcyclopentasiloxane was obtained.

$$(Me_3SiO_{1/2})_{27.7}(HMe_2SiO_{1/2})_{11.9}(SiO_2)_{39.6} \quad \text{Average composition formula (E17):}$$

$$CH_2{=}CH{-}CH_2{-}O{-}(C_2H_4O)_{10}{-}CH_2{-}CH{=}CH_2 \quad \text{formula (E18):}$$

$$CH_2{=}CH{-}(SiO(CH_3)_2)_8{-}Si(CH_3)_3 \quad \text{formula (E19):}$$

Average Composition Formula (E20):

$$(Me_3SiO_{1/2})_{27.7}(X_{1/2}Me_2SiO_{1/2})_{3.6}(R^3Me_2SiO_{1/2})_{8.3}(SiO_{4/2})_{39.6}$$

$$X{=}{-}CH_2{-}CH{-}CH_2{-}O{-}(C_2H_4O)_{10}{-}CH_2{-}CH{-}CH_2{-}$$

$$R^3{=}{-}CH_2{-}CH_2{-}(SiO(CH_3)_2)_8{-}Si(CH_3)_3$$

wherein Me represents a methyl group, hereinafter the same. In the formula (E20), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was gum (weight-average molecular weight: 105,000).

The HLB of the product was 1.6.

Preparation Example 6

Method for Preparing Crosslinked Organic Silicon Resin

To a reactor, 400 g of 50% solution of powdery hydrosilyl group-containing organic silicon resin represented by the average composition formula (E21) (weight-average molecular weight: 5,630, the amount of hydrosilyl group: 2.06 mmol/g) in decamethylcyclopentasiloxane, 50.3 g of polyoxyalkylene having allyl groups at both ends, represented by the following formula (E22), 330.1 g of 2-propanol, and 0.5 g of 0.5% solution of chloroplatinic acid in ethanol were added, and the reaction was conducted by heating at 80° C. for three hours. After confirming the reaction, 209.8 g of organopolysiloxane having a vinyl group at one end, represented by the following formula (E23) was added, and the resultant was heated at 80° C. for three hours. Thereafter, 33.0 g of 2% aqueous citric acid solution was added, and the resultant was heated at 80° C. for three hours to hydrolyze an allylether group of unreacted polyoxyalkylene, and the resultant was neutralized with 20.0 g of 5% sodium bicarbonate water. A reaction product was heated under reduced pressure to distill off the solvent, and was then filtrated. Thus, a solution of the crosslinked organic silicon resin represented by the following formula (E24) in decamethylcyclopentasiloxane was obtained.

$$(Me_3SiO_{1/2})_{28.8}(HMe_2SiO_{1/2})_{12.3}(SiO_2)_{41.2}$$

formula (E22)

$$CH_2{=}CH{-}CH_2{-}O{-}(C_2H_4O)_{10}{-}CH_2{-}CH{=}CH_2$$

formula (E23)

$$CH_2{=}CH{-}(SiO(CH_3)_2)_8{-}Si(CH_3)_3$$

Average composition formula (E24)

$$(Me_3SiO_{1/2})_{28.8}(X_{1/2}Me_2SiO_{1/2})_{3.9}(R^3Me_2SiO_{1/2})_{8.2}(SiO_{4/2})_{41.2}$$

$$X = {-}CH_2{-}CH{-}CH_2{-}O{-}(C_2H_4O)_{15}{-}CH_2{-}CH{-}CH_2{-}$$

$$R^3 = {-}CH_2{-}CH_2{-}(SiO(CH_3)_2)_8{-}Si(CH_3)_3$$

wherein Me represents a methyl group, hereinafter the same. In the formula (E24), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was gum (weight-average molecular weight: 82,600).

The HLB of the product was 2.2.

Preparation Example 7

Method for Preparing Crosslinked Organic Silicon Resin

To a reactor, 200 g of 50% solution of liquid hydrosilyl group-containing organic silicon resin represented by the average composition formula (E25) (weight-average molecular weight: 3,080, the amount of hydrosilyl group: 1.95 mmol/g) in decamethylcyclopentasiloxane, 73.8 g of organopolysiloxane having a vinyl group at one end, represented by the following formula (E26), 148.8 g of 2-propanol, and 0.2 g of 0.5% solution of chloroplatinic acid in ethanol were added, and the reaction was conducted by heating at 80° C. for three hours. After confirming the reaction, 23.8 g of polyoxyalkylene having an allyl group at one end, represented by the following formula (E27) was added, and the resultant was heated at 80° C. for three hours. Thereafter, 14.9 g of 2% aqueous citric acid solution was added, and the resultant was heated at 80° C. for three hours to hydrolyze an allylether group of unreacted polyoxyalkylene, and the resultant was neutralized with 9.0 g of 5% sodium bicarbonate water. A reaction product was heated under reduced pressure to distill off the solvent, and was then filtrated. Thus, a solution of the crosslinked organic silicon resin represented by the following formula (E28) in decamethylcyclopentasiloxane was obtained.

Average composition formula (E25)

$$(Me_3SiO_{1/2})_{13.1}(HMe_2SiO_{1/2})_{5.6}(MeSio_{3/2})_{15.3}(SiO_2)_{10.2}$$

formula (E26)

$$CH_2{=}CH{-}(SiO(CH_3)_2)_8{-}Si(CH_3)_3$$

formula (E27)

$$CH_2{=}CH{-}CH_2{-}O{-}(C_2H_4O)_{10}{-}CH_2{-}CH{=}CH_2$$

Average composition formula (E28)

$$(Me_3SiO_{1/2})_{13.1}(X_{1/2}Me_2SiO_{1/2})_{2.2}(R^3Me_2SiO_{1/2})_{3.4}(MeSiO_{3/2})_{15.3}(SiO_2)_{10.2}$$

$$X{=}{-}CH_2{-}CH{-}CH_2{-}O{-}(C_2H_4O)_{10}{-}CH_2{-}CH{-}CH_2{-}$$

$$R^3{=}{-}CH_2{-}CH_2{-}(SiO(CH_3)_2)_8{-}Si(CH_3)_3$$

wherein Me represents a methyl group, hereinafter the same. In the formula (E25), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was a colorless transparent liquid (weight-average molecular weight: 33,500).

The HLB of the product was 1.9.

Preparation Example 8

Method for Preparing Crosslinked Organic Silicon Resin

To a reactor, 700 g of 50% solution of powdery hydrosilyl group-containing organic silicon resin represented by the average composition formula (E29) (weight-average molecular weight: 3,200, the amount of hydrosilyl group: 1.97 mmol/g) in decamethylcyclopentasiloxane, 39.2 g of polyglycerin having allyl groups at both ends, represented by the following formula (E30), 536.7 g of 2-propanol, and 0.7 g of 0.5% solution of chloroplatinic acid in ethanol were added, and the reaction was conducted by heating at 80° C. for three hours. After confirming the reaction, 334.1 g of organopolysiloxane having a vinyl group at one end, represented by the following formula (E31) was added, and the resultant was heated at 80° C. for three hours. Thereafter, 53.7 g of 2% aqueous citric acid solution was added, and the resultant was heated at 80° C. for three hours to hydrolyze an allylether group of unreacted polyoxyalkylene, and the resultant was neutralized with 32.5 g of 5% sodium bicarbonate water. A reaction product was heated under reduced pressure to distill off the solvent, and was then filtrated. Thus, a solution of the crosslinked organic silicon resin represented by the following formula (E32) in decamethylcyclopentasiloxane was obtained.

Average composition formula (E29)

$$(Me_3SiO_{1/2})_{17.7}(HMe_2SiO_{1/2})_{7.6}(SiO_2)_{21.0}$$

formula (E30)

$$CH_2{=}CH{-}CH_2{-}O{-}Q^1{-}CH_2{-}CH{=}CH_2$$

The formula (E30) is mainly a compound where $Q^1$ is $(CH_2CH(OH)CH_2O)_3$ derived from glycerin. Further, the formula (E30) is a mixture including isomers having one or more structure where $Q^1$ is represented by the afore-mentioned formula (4) to (10) and $R^4$ is a hydrogen atom.

Average composition formula (E32)

$$(Me_3SiO_{1/2})_{17.7}(X_{1/2}Me_2SiO_{1/2})_{2.7}(R^3Me_2SiO_{1/2})_{4.9}(SiO_{4/2})_{21.0}$$

$$X = {-}CH_2{-}CH{-}CH_2{-}O{-}Q^1{-}CH_2{-}CH{-}CH_2{-}$$

wherein X has a main structure where $Q^1$ is $(CH_2CH(OH)CH_2O)_3$. Further, X has a structure having one or more structures where $Q^1$ is represented by the formula (4) to (10) and $R^4$ is a hydrogen atom.

$$R^3 = {-}CH_2{-}CH_2{-}(SiO(CH_3)_2)_8{-}Si(CH_3)_3$$

wherein Me represents a methyl group, hereinafter the same. In the formula (E32), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was a colorless transparent liquid (weight-average molecular weight: 58,000).

The HLB of the product was 1.2.

Preparation Example 9

Method for Preparing Crosslinked Organic Silicon Resin

To a reactor, 300 g of 50% solution of powdery hydrosilyl group-containing organic silicon resin represented by the average composition formula (E33) (weight-average molecular weight: 2,560, the amount of hydrosilyl group: 1.63 mmol/g) in decamethylcyclopentasiloxane, 64.5 g of organopolysiloxane having a vinyl group at one end, represented by the following formula (E34), 201.7 g of 2-propanol, and 0.3 g of 0.5% solution of chloroplatinic acid in ethanol were added, and the reaction was conducted by heating at 80° C. for three hours. After confirming the reaction, 39.0 g of polyoxyalkylene having an allyl group at one end, represented by the following formula (E35) was added, and the resultant was heated at 80° C. for three hours. Thereafter, 20.2 g of 2% aqueous citric acid solution was added, and the resultant was heated at 80° C. for three hours to hydrolyze an allylether group of unreacted polyoxyalkylene, and the resultant was neutralized with 12.2 g of 5% sodium bicarbonate water. A reaction product was heated under reduced pressure to distill off the solvent, and was then filtrated. Thus, a solution of the crosslinked organic silicon resin represented by the following formula (E36) in decamethylcyclopentasiloxane was obtained.

Average composition formula (E33)

$$(Me_3SiO_{1/2})_{16.2}(HMe_2SiO_{1/2})_{3.4}(SiO_2)_{17.0}$$

formula (E34)

$$CH_2{=}CH{-}(SiO(CH_3)_2)_8{-}Si(CH_3)_3$$

formula (E35)

$$CH_2{=}CH{-}CH_2{-}O{-}(C_2H_4O)_{10}{-}CH_2{-}CH{=}CH_2$$

Average composition formula (E36)

$$(Me_3SiO_{1/2})_{16.2}(X_{1/2}Me_2SiO_{1/2})_{2.2}(R^3Me_2SiO_{1/2})_{1.2}(SiO_2)_{17.0}$$

$$X = {-}CH_2{-}CH{-}CH_2{-}O{-}(C_2H_4O)_{10}{-}CH_2{-}CH{-}CH_2{-}$$

$$R^3 = {-}CH_2{-}CH_2{-}(SiO(CH_3)_2)_8{-}Si(CH_3)_3$$

wherein Me represents a methyl group, hereinafter the same. In the formula (E36), some X may be a hydroxyl group.

A solution of the obtained crosslinked organic silicon resin in decamethylcyclopentasiloxane was heated at 120° C. to 130° C. under reduced pressure to remove decamethylcyclopentasiloxane. The resultant product was a colorless transparent liquid (weight-average molecular weight: 80,200).

The HLB of the product was 2.9.

Preparation Example 10

Method for Preparing Crosslinked Organic Silicon Resin

To a reactor, 400 g of 50% solution of powdery hydrosilyl group-containing organic silicon resin represented by the average composition formula (E37) (weight-average molecular weight: 2,220, the amount of hydrosilyl group: 1.70 mmol/g) in decamethylcyclopentasiloxane, 124.2 g of organopolysiloxane having a vinyl group at one end, represented by the following formula (E38), 288.4 g of 2-propanol, and 0.4 g of 0.5% solution of chloroplatinic acid in ethanol were added, and the reaction was conducted by heating at 80° C. for three hours. After confirming the reaction, 31.2 g of polyoxyalkylene having allyl groups at both ends, represented by the following formula (E39) and 21.4 g of polyoxyalkylene having an allyl group at one end, represented by the following formula (E40) were added, and the resultant was heated at 80° C. for three hours. Thereafter, 28.8 g of 2% aqueous citric acid solution was added, and the resultant was heated at 80° C. for three hours to hydrolyze an allylether group of unreacted polyoxyalkylene, and the resultant was neutralized with 17.5 g of 5% sodium bicarbonate water. A reaction product was heated under reduced pressure to distill off the solvent, and was then filtrated. Thus, a solution of the crosslinked organic silicon resin represented by the following formula (E41) in decamethylcyclopentasiloxane was obtained.

Average composition formula (E37)

$$(Me_3SiO_{1/2})_{12.3}(HMe_2SiO_{1/2})_{4.3}(SiO_2)_{15.6}$$

formula (E38)

$$CH_2{=}CH{-}(SiO(CH_3)_2)_8{-}Si(CH_3)_3$$

formula (E39)

$$CH_2{=}CH{-}CH_2{-}O{-}(C_2H_4O)_{10}{-}CH_2{-}CH{=}CH_2$$

formula (E40)

$$CH_2{=}CH{-}CH_2{-}O{-}(C_2H_4O)_9{-}H$$

Average composition formula (E41)

$$(Me_3SiO_{1/2})_{12.3}(X_{1/2}Me_2SiO_{1/2})_{1.6}(R^2Me_2SiO_{1/2})_{0.6}(R^3Me_2SiO_{1/2})_{2.1}(SiO_2)_{15.6}$$

$$X = {-}CH_2{-}CH{-}CH_2{-}O{-}(C_2H_4O)_{10}{-}CH_2{-}CH{-}CH_2{-}$$

$$R^2 = {-}CH_2{-}CH{-}CH_2{-}O{-}(C_2H_4O)_9{-}H$$

$$R^3 = {-}CH_2{-}CH_2{-}(SiO(CH_3)_2)8{-}Si(CH_3)_3$$

wherein Me represents a methyl group, hereinafter the same. In the formula (E41), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was a colorless transparent liquid (weight-average molecular weight: 68,000).

The HLB of the product was 3.1.

Preparation Example 11

Method for Preparing 50% Solution of Crosslinked Organic Silicon Resin in Decamethylcyclopentasiloxane To a reactor, 600 g of 50% solution of powdery hydrosilyl group-containing organic silicon resin represented by the average composition formula (E42) (weight-average molecular weight: 3,020, the amount of hydrosilyl group: 0.554 mmol/g) in decamethylcyclopentasiloxane, 16.6 g of polyoxyalkylene having allyl groups at both ends, represented by the following formula (E43), 308.3 g of 2-propanol, and 0.3 g of 0.5% solution of chloroplatinic acid in ethanol were added, and the reaction was conducted by heating at 80° C. for three hours. After confirming the reaction, 30.8 g of 2% aqueous citric acid solution was added, and the resultant was heated at 80° C. for three hours to hydrolyze an allylether group of unreacted polyoxyalkylene, and the resultant was neutralized with 18.7 g of 5% sodium bicarbonate water. A reaction product was heated under reduced pressure to distill off the solvent, and was then filtrated. Thus, a solution of the crosslinked organic silicon resin represented by the following formula (E44) in decamethylcyclopentasiloxane was obtained.

Average composition formula (E42)

$$(Me_3SiO_{1/2})_{17.8}(HMe_2SiO_{1/2})_{1.6}(SiO_2)_{24.6}$$

formula (E43)

$$CH_2{=}CH{-}CH_2{-}O{-}(C_2H_4O)_4{-}CH_2{-}CH{=}CH_2$$

Average composition formula (E44)

$$(Me_3SiO_{1/2})_{17.8}(X_{1/2}Me_2SiO_{1/2})_{1.6}(SiO_2)_{24.6}$$

$$X = {-}CH_2{-}CH{-}CH_2{-}O{-}(C_2H_4O)_4{-}CH_2{-}CH{-}CH_2{-}$$

wherein Me represents a methyl group, hereinafter the same. In the formula (E44), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was solid (weight-average molecular weight: 54,500).

The HLB of the product was 0.8.

The solid crosslinked organic silicon resin was dissolved in decamethylcyclopentasiloxane so that the content of the solid crosslinked organic silicon resin reaches 50 mass %.

Preparation Example 12

Method for Preparing Crosslinked Organic Silicon Resin

To a reactor, 200 g of 50% solution of powdery hydrosilyl group-containing organic silicon resin represented by the average composition formula (E45) (weight-average molecular weight: 6,130, the amount of hydrosilyl group: 2.24 mmol/g) in decamethylcyclopentasiloxane, 5.5 g of polyoxyalkylene having allyl groups at both ends, represented by the following formula (E46), 390.7 g of 2-propanol, and 0.7 g of 0.5% solution of chloroplatinic acid in ethanol were added, and the reaction was conducted by heating at 80° C. for three hours. After confirming the reaction, 575.8 g of organopolysiloxane having a vinyl group at one end, represented by the following formula (E47) was added, and the resultant was heated at 80° C. for three hours. Thereafter, 39.1 g of 2% aqueous citric acid solution was added, and the resultant was heated at 80° C. for three hours to hydrolyze an allylether group of unreacted polyoxyalkylene, and the resultant was neutralized with 23.6 g of 5% sodium bicarbonate water. A reaction product was heated under reduced pressure to distill off the solvent, and was then filtrated. Thus, a solution of the crosslinked organic silicon resin represented by the following formula (E48) in decamethylcyclopentasiloxane was obtained.

Average composition formula (E45)

$$(Me_3SiO_{1/2})_{25.2}(HMe_2SiO_{1/2})_{14.0}(SiO_2)_{52.4}$$

formula (E46)

$$CH_2{=}CH{-}CH_2{-}O{-}(C_2H_4O)_{10}{-}CH_2{-}CH{=}CH_2$$

formula (E47)

$$CH_2{=}CH{-}(SiO)(CH_3)_2)_{40}{-}Si(CH_3)_3$$

Average composition formula (E48)

$$(Me_3SiO_{1/2})_{25.2}(X_{1/2}Me_2SiO_{1/2})_{1.4}(R^3Me_2SiO_{1/2})_{12.6}(SiO_{4/2})_{52.4}$$

$$X = {-}CH_2{-}CH{-}CH_2{-}O{-}(C_2H_4O)_{15}{-}CH_2{-}CH{-}CH_2{-}$$

$$R^3 = {-}CH_2{-}CH_2{-}(SiO(CH_3)_2)_{40}{-}Si(CH_3)_3$$

wherein Me represents a methyl group, hereinafter the same. In the formula (E48), some X may be a hydroxyl group.

A solution of the obtained crosslinked organic silicon resin in decamethylcyclopentasiloxane was heated to 120° C. to 130° C. under reduced pressure to remove decamethylcyclopentasiloxane. The resultant product was liquid (weight-average molecular weight: 65,000).

The HLB of the product was 0.9.

Preparation Example 13

Method for Preparing Crosslinked Organic Silicon Resin

To a reactor, 400 g of 50% solution of powdery hydrosilyl group-containing organic silicon resin represented by the average composition formula (E49) (weight-average molecular weight: 6,130, the amount of hydrosilyl group: 2.24 mmol/g) in decamethylcyclopentasiloxane, 12.6 g of polyoxyalkylene having allyl groups at both ends, represented by the following formula (E50), 178.7 g of polyoxyalkylene having an allyl group at one end, represented by the following formula (E51), 206.3 g of 2-propanol, and 0.4 g of 0.5% solution of chloroplatinic acid in ethanol were added, and the reaction was conducted by heating at 80° C. for three hours. Thereafter, 20.6 g of 2% aqueous citric acid solution was added, and the resultant was heated at 80° C. for three hours to hydrolyze an allylether group of unreacted polyoxyalkylene, and the resultant was neutralized with 12.5 g of 5% sodium bicarbonate water. A reaction product was heated to 120° C. to 130° C. under reduced pressure to distill off the solvent (decamethylcyclopentasiloxane), thereby obtaining a crosslinked organic silicon resin represented by the following formula (E52).

Average composition formula (E49)

$$(Me_3SiO_{1/2})_{25.2}(HMe_2SiO_{1/2})_{14.0}(SiO_2)_{52.4}$$

formula (E50)

$$CH_2{=}CH{-}CH_2{-}O{-}(C_2H_4O)_{10}{-}CH_2{-}CH{=}CH_2$$

formula (E51)

$$CH_2{=}CH{-}CH_2{-}O{-}(C_2H_4O)_9{-}H$$

Average composition formula (E52)

$$(Me_3SiO_{1/2})_{25.2}(X_{1/2}Me_2SiO_{1/2})_{1.6}(R^2Me_2SiO_{1/2})_{12.4}(SiO_{4/2})_{52.4}$$

$$X = {-}CH_2{-}CH{-}CH_2{-}O{-}(C_2H_4O)_{15}{-}CH_2{-}CH{-}CH_2{-}$$

$$R^2 = {-}CH_2{-}CH{-}CH_2{-}O{-}(C_2H_4O)_9{-}H$$

wherein Me represents a methyl group, hereinafter the same. In the formula (E52), some X may be a hydroxyl group.

The obtained product was gum (weight-average molecular weight: 45,000).

The HLB of the product was 9.9.

Comparative Example 1

Method for Preparing Modified Crosslinked Organic Silicon Resin

To a reactor, 200 g of 50% solution of powdery hydrosilyl group-containing organic silicon resin represented by the average composition formula (E53) (weight-average molecular weight: 5,420, the amount of hydrosilyl group: 1.95 mmol/g) in decamethylcyclopentasiloxane, 131.4 g of organopolysiloxane having a vinyl group at one end, represented by the following formula (E54), 165.7 g of 2-propanol, and 0.2 g of 0.5% solution of chloroplatinic acid in ethanol were added, and the reaction was conducted by heating at 80° C. for three hours. After confirming the reaction, 9.0 g of polyoxyalkylene having an allyl group at one end, represented by the following formula (E55) was added, and the resultant was heated at 80° C. for three hours. Thereafter, 16.6 g of 2% aqueous citric acid solution was added, and the resultant was heated at 80° C. for three hours to hydrolyze an allylether group of unreacted polyoxyalkylene, and the resultant was neutralized with 10.0 g of 5% sodium bicarbonate water. A reaction product was heated under reduced pressure to distill off the solvent, and was then filtrated. Thus, a solution of the modified (uncrosslinked) organic silicon resin represented by the following formula (E56) in decamethylcyclopentasiloxane was obtained.

$$(Me_3SiO_{1/2})_{27.7}(HMe_2SiO_{1/2})_{11.9}(SiO_2)_{39.6}$$

formula (E54)

$$CH_2{=}CH{-}(SiO(CH_3)_2)_8{-}Si(CH_3)_3$$

formula (E55)

$$CH_2{=}CH{-}CH_2{-}O{-}(C_2H_4O)_9{-}H$$

$$(Me_3SiO_{1/2})_{27.7}(R^2Me_2SiO_{1/2})_{2.4}(R^3Me_2SiO_{1/2})_{9.5}(SiO_{4/2})_{39.6}$$

$$R^2 = {-}CH_2{-}CH{-}CH_2{-}O{-}(C_2H_4O)_9{-}H$$

$$R^3 = {-}CH_2{-}CH_2{-}(SiO(CH_3)_2)_8{-}Si(CH_3)_3$$

wherein Me represents a methyl group, hereinafter the same.

A solution of the obtained modified organic silicon resin in decamethylcyclopentasiloxane was heated to 120° C. to 130° C. under reduced pressure to remove decamethylcyclopentasiloxane. The resultant product was liquid (weight-average molecular weight: 12,000).

The HLB of the product was 1.9.

Preparation Example 14

Method for Preparing 50% Solution of Crosslinked Organic Silicon Resin (Preparation Example 5) in Dimethicone (6cs)

The crosslinked organic silicon resin having a form of gum obtained on Preparation Example 5 and dimethicone (6cs) were added to a nitrogen-substituted separable flask to uniformly dissolve the crosslinked organic silicon resin by a glass stirrer at 80° C., thereby preparing 50% solution.

Preparation Example 15

Method for Preparing 50% Solution of Crosslinked Organic Silicon Resin (Preparation Example 6) in Dimethicone (6cs)

The crosslinked organic silicon resin having a form of gum obtained on Preparation Example 6 and dimethicone (6cs) were added to a nitrogen-substituted separable flask to uniformly dissolve the crosslinked organic silicon resin by a glass stirrer at 80° C., thereby preparing 50% solution.

The crosslinked organic silicon resins obtained in the preparation examples can be dissolved in various oil agents used in cosmetics, such as silicones including D5, methyl trimethicone, and dimethicones (1.5cs, 2cs), ester oils including triethylhexanoin and isotridecyl isononanoate, and hydrocarbon oils including isododecane and squalane, other than dimethicone (6cs). The viscosity of these solutions can vary depending on the compositions and molecular weights of the polymers.

Examples 1 to 4 and Comparative Examples 2 to 4

Each cream in composition shown in Table 1 below was prepared.

TABLE 1

| | Component | Example 1 | Example 2 | Example 3 | Example 4 | Comparative Example 2 | Comparative Example 3 | Comparative Example 4 |
|---|---|---|---|---|---|---|---|---|
| 1 | Composition of Preparation Example 1 | 2 | | | | | | |
| | Composition of Preparation Example 2 | | 2 | | | | | |
| | Composition of Preparation Example 4 | | | 2 | | | | |
| | Composition of Preparation Example 14 | | | | 4 | | | |
| | KSG-210 (Note 1) | | | | | 2 | 8 | |
| | Composition of Comparative Example 1 | | | | | | | 2 |
| 2 | Dimethyl polysiloxane (6cs) | 11 | 11 | 11 | 9 | 11 | 5 | 11 |
| 3 | BG | 8 | 8 | 8 | 8 | 8 | 8 | 8 |
| 4 | Sodium chloride | 0.5 | 0.5 | 0.5 | 0.5 | 0.5 | 0.5 | 0.5 |
| 5 | Water | 78.5 | 78.5 | 78.5 | 78.5 | 78.5 | 78.5 | 78.5 |
| | Total | 100 | 100 | 100 | 100 | 100 | 100 | 100 |

(Note 1) Mixture of 25% (dimethicone/(PEG-10/15)) crosspolymer (Japanese labeling name) (INCI: Dimethicone/PEG-10/15 crosspolymer) and 75% dimethicone (Japanese labeling name) (INCI: Dimethicone)

(Preparation Method)

Components 1 and 2 were mixed so as to be uniform. Components 3 to 5, which had been uniformly mixed, were gently added thereto, and they were stirred. Thus, an emulsion was obtained. The emulsion was filled in a predetermined vessel to obtain a cream. The cream thus obtained was evaluated as follows.

[Usability Evaluation]

The obtained cosmetics were evaluated by 10 specialized panelists based on the criteria shown in Table 2 below regarding spreading property (good spreading property) and richness (thick-film feeling of use). The results were determined according to the determination criteria based on the average of the 10 evaluation results.

TABLE 2

| Criteria | Spreading property | Richness |
|---|---|---|
| 5 points | Excellent | Excellent |
| 4 points | Very Good | Very Good |
| 3 points | Good | Good |
| 2 points | Average | Average |
| 1 point | Poor | Poor |

Based on the average score of the obtained evaluation results, the results based on the following are shown in Table 3.

Excellent: Average score of 4.0 points or more

Good: Average score of 3.0 points or more and less than 4.0 points

Fair: Average score of 2.0 points or more and less than 3.0 points

Poor: Average score of less than 2.0 points

Stability Over Time

The initial viscosity of each emulsion obtained was compared with the viscosity after storage for one month in a thermostatic chamber at 50° C., and the change in viscosity from the initial viscosity was evaluated. Table 3 shows the results.

Excellent: ±0% or more to less than 5%

Good: ±5% or more to less than 10%

Fair: ±10% or more to less than 15%

Poor: ±20% or more

TABLE 3

| | Example 1 | Example 2 | Example 3 | Example 4 | Comparative Example 2 | Comparative Example 3 | Comparative Example 4 |
|---|---|---|---|---|---|---|---|
| Spreading property | Excellent | Excellent | Excellent | Good | Excellent | Poor | Good |
| Richness | Excellent | Excellent | Good | Excellent | Poor | Excellent | Poor |
| Stability over time | Excellent | Excellent | Good | Good | Fair | Fair | Fair |

As shown in Table 3, cosmetics of the present invention were significantly superior to those of Comparative Examples 3 to 5 in terms of spreading property, richness, and stability over time.

Example 5 and Comparative Examples 5 and 6

Each sunscreen milk with the composition shown in Table 4 below was prepared.

TABLE 4

| | Component | Example 5 | Comparative Example 5 | Comparative Example 6 |
|---|---|---|---|---|
| 1 | Composition of Preparation Example2 | 2 | | |
| | KSG-210 (Note 1) | | 2 | |

TABLE 4-continued

| | Component | Example 5 | Comparative Example 5 | Comparative Example 6 |
|---|---|---|---|---|
| 2 | KSG-15 (Note 2) | 2 | 2 | 2 |
| 3 | KF-6028 (Note 3) | | | 2 |
| 4 | Cyclopentasiloxane | 5 | 5 | 5 |
| 5 | Isotridecyl isononanoate | 4 | 4 | 4 |
| 6 | KF-96A-6cs (Note 4) | 4 | 4 | 4 |
| 7 | SPD-T5 (Note 5) | 25 | 25 | 25 |
| 8 | SPD-Z5 (Note 6) | 35 | 35 | 35 |
| 9 | DPG | 5 | 5 | 5 |
| 10 | Sodium citrate | 0.2 | 0.2 | 0.2 |
| 11 | Sodium chloride | 1 | 1 | 1 |
| 12 | Water | 16.8 | 16.8 | 16.8 |
| | Total | 100 | 100 | 100 |

(Note 1)
Mixture of 25% dimethicone/(PEG-10/15) crosspolymer (labeling name) (INCI: Dimethicone/PEG-10/15 crosspolymer) and 75% dimethicone (labeling name) (INCI: DIMETHICONE), produced by Shin-Etsu Chemical Co., Ltd.
(Note 2)
Mixture of 7% (dimethicone/vinyl dimethicone) crosspolymer (labeling name) (INCI: Dimethicone/Vinyl Dimethicone Crosspolymer) and 93% cyclopentasiloxane (labeling name) (INCI: Cyclopentasiloxane), produced by Shin-Etsu Chemical Co., Ltd.
(Note 3)
PEG-9 polydimethylsiloxyethyl dimethicone (labeling name) (INCI: PEG-9 Polydimethylsiloxyethyl Dimethicone) produced by Shin-Etsu Chemical Co., Ltd.
(Note 4)
Dimethicone (labeling name) (INCI: DIMETHICONE) produced by Shin-Etsu Chemical Co., Ltd.
(Note 5)
40% dispersion of titanium dioxide (labeling name) (INCI: Titanium Dioxide) produced by Shin-Etsu Chemical Co., Ltd.
(Note 6)
60% dispersion of zinc oxide (labeling name) (INCI: Zinc Oxide) produced by Shin-Etsu Chemical Co., Ltd.

(Preparation Method)

Components 1 to 6 were mixed so as to be uniform. Components 9 to 12, which had been uniformly mixed, were gently added thereto, and they were stirred. Thus, an emulsion was obtained. Thereafter, components 7 and 8 were added to the emulsion and mixed. The mixture was placed in a vessel. Thus, a sunscreen milk was obtained. The obtained sunscreen milk was evaluated as follows.

[Usability Evaluation]

The obtained cosmetics were evaluated by 10 specialized panelists based on the following criteria regarding spreading property (good spreading property), richness (thick-film feeling of use), white cast (whitening resistance when the sunscreen cosmetics is applied), and whitening (whitening resistance when the sunscreen cosmetic is wet after applying and drying the sunscreen cosmetic). The results were determined according to the determination criteria based on the average of the 10 evaluation results. The evaluations for spreading property and richness were performed by the same methods as described above.

White Cast

When the same amount was applied, 5 points were given for very high transparency, 4 points for high transparency, 3 points for a slightly white finish, 2 points for white finish, and 1 point for very white finish.

Excellent: Average score of 4.0 points or more
Good: Average score of 3.0 points or more and less than 4.0 points
Fair: Average score of 2.0 points or more and less than 3.0 points
Poor: Average score of less than 2.0 points Whitening The sunscreen cosmetic was applied to 1 mm thick quartz glass plate with a bar coater (KOTEC: KOSP—CN-05M), dried at 50° C. for 2 hours, and then immersed in purified water for 10 minutes, and thereafter, the water content was removed and measured. The transmittance at 410 nm measured by a spectrophotometer (U-3310) manufactured by Hitachi High-Tech Science as a measurement machine was evaluated.

Excellent: 90% or more
Good: 85% or more and less than 90%
Fair: 80% or more and less than 85%
Poor: less than 80%

TABLE 5

| | Example 5 | Comparative Example 5 | Comparative Example 6 |
|---|---|---|---|
| Spreading property | Excellent | Excellent | Good |
| Richness | Excellent | Poor | Excellent |
| White Cast | Excellent | Fair | Excellent |
| Whitening | Excellent | Excellent | Poor |

As shown in Table 5, cosmetics of the present invention were significantly superior to those of Comparative Examples 5 and 6 in terms of spreading property, richness, white cast, and whitening.

Example 6 and Comparative Examples 7 and 8

Each sunscreen cream in composition shown in Table 6 below was prepared.

TABLE 6

| | Component | Example 6 | Comparative Example 7 | Comparative Example 8 |
|---|---|---|---|---|
| 1 | KSG-210 (Note1) | 3.5 | 3.5 | 3.5 |
| 2 | KSG-18A (Note2) | 3 | 3 | 3 |
| 3 | Composition of Preparation Example3 | 0.5 | | |
| 4 | KF-6038 (Note3) | | 0.5 | |
| 5 | Cyclopentasiloxane | 6.5 | 6.5 | 7 |
| 6 | KF-56A (Note4) | 5 | 5 | 5 |
| 7 | Ethylhexyl methoxysilicate | 7.5 | 7.5 | 7.5 |
| 8 | BG | 5.5 | 5.5 | 5.5 |
| 9 | Sodium citrate | 0.2 | 0.2 | 0.2 |
| 10 | Sodium chloride | 0.5 | 0.5 | 0.5 |
| 11 | Water | 67.8 | 67.8 | 67.8 |
| | Total | 100 | 100 | 100 |

(Note1)
Mixture of 25% dimethicone/(PEG-10/15) crosspolymer (labeling name) (INCI: Dimethicone/PEG-10/15 crosspolymer) and 75% dimethicone (labeling name) (INCI: DIMETHICONE), produced by Shin-Etsu Chemical Co., Ltd.
(Note2)
Mixture of 15% (dimethicone/phenyl vinyl dimethicone) crosspolymer (labeling name) (INCI: Dimethicone/Phenyl Vinyl Dimethicone Crosspolymer) and 85% diphenylsiloxy phenyl trimethicone (labeling name) (INCI: Diphenylsiloxy Phenyl Trimethicone), produced by Shin-Etsu Chemical Co., Ltd.
(Note3)
Lauryl PEG-9 polydimethylsiloxyethyl dimethicone (labeling name) (INCI: Lauryl PEG-9 Polydimethylsiloxyethyl Dimethicone) produced by Shin-Etsu Chemical Co., Ltd.
(Note4)
Diphenylsiloxy phenyl trimethicone (labeling name) (INCI: Diphenylsiloxy Phenyl Trimethicone) produced by Shin-Etsu Chemical Co., Ltd.

(Preparation Method)

Components 1 to 7 were mixed so as to be uniform. Components 8 to 11, which had been uniformly mixed, were gently added thereto, and they were stirred. Thus, an emulsion was obtained. The emulsion was filled in a predetermined vessel to obtain a sunscreen.

[Usability Evaluation]

The obtained cosmetics were evaluated by 10 specialized panelists based on the following criteria regarding freshness and stability over time. The results were determined according to the determination criteria based on the average of the 10 evaluation results. The evaluation for stability was performed by the same method as described above.

Freshness

After phase inversion immediately after application of the same amount, 5 points were given when fresh feeling of use of the inner phase was obtained, 3 points were given when it was barely obtained, and 1 point was given when it was not obtained at all.

Excellent: Average score of 4.0 points or more

Good: Average score of 3.0 points or more and less than 4.0 points

Fair: Average score of 2.0 points or more and less than 3.0 points

Poor: Average score of less than 2.0 points

TABLE 7

| | Example | Comparative Example | |
|---|---|---|---|
| | 6 | 7 | 8 |
| Freshness | Excellent | Poor | Excellent |
| Stability over time | Excellent | Excellent | Poor |

As shown in Table 7, the cosmetics of the present invention were significantly superior to those of Comparative Examples 7 and 8 in terms of both freshness and stability over time.

Examples of the cosmetics are shown below. The cosmetics were evaluated below based on the criteria described above.

Example 7

W/O Cream

<Preparation of Cosmetic>

A: Components 1 to 4 were uniformly mixed.

B: Components 5 to 11 were uniformly mixed.

C: The mixture of B was added to the mixture of A, and they were emulsified to obtain a W/O cream.

| | Components | Mass % |
|---|---|---|
| 1. | KSG-310 (Note 1) | 3 |
| 2. | KSG-44 (Note 2) | 1 |
| 3. | Composition of Preparation Example 5 | 0.2 |
| 4. | Squalane | 10.8 |
| 5. | BG | 6 |
| 6. | Ethanol | 5 |
| 7. | Glycerin | 2 |
| 8. | Sodium Citrate | 0.2 |
| 9. | Sodium Chloride | 0.5 |
| 10. | Phenoxy Ethanol | 0.2 |
| 11. | Water | Balance |
| Total | | 100 |

(Note 1)
Mixture of 30% (PEG-15/lauryl dimethicone) crosspolymer (labeling name) (INCI: PEG-15/Lauryl Dimethicone Crosspolymer) and 70% mineral oil (labeling name) (INCI: Mineral Oil), produced by Shin-Etsu Chemical Co., Ltd.
(Note 2)
Mixture of 30% (vinyl dimethicone/lauryl dimethicone) crosspolymer (labeling name) (INCI: Vinyl Dimethicone/Lauryl Dimethicone Crosspolymer) and 70% squalane (labeling name) (INCI: Squalane), produced by Shin-Etsu Chemical Co., Ltd.

The obtained W/O cream was excellent in spreading property and richness and had fresh feeling and good stability over time.

Example 8

W/O Cream

<Preparation of Cosmetic>

A: Components 1 to 4 were uniformly mixed.

B: Components 5 to 14 were uniformly mixed.

C: The mixture of B was added to the mixture of A, and they were emulsified to obtain a W/O cream.

| | Components | Mass % |
|---|---|---|
| 1. | Composition of Preparation Example 8 | 4 |
| 2. | KSG-18A (Note 1) | 1 |
| 3. | KF-6104 (Note 2) | 3 |
| 4. | KF-96A-6cs | 13 |
| 5. | BG | 8 |
| 6. | Ethanol | 5 |
| 7. | Sorbitol | 2 |
| 8. | Sodium Citrate | 0.2 |
| 9. | Sodium Chloride | 0.5 |
| 10. | Methylparaben | 0.1 |
| 11. | 2K glycyrrhizinate | 0.2 |
| 12. | Arbutin | 3 |
| 13. | Sodium metabisulfite | 0.02 |
| 14. | Water | Balance |
| Total | | 100 |

(Note 1)
Mixture of 15% (dimethicone/phenyl vinyl dimethicone) crosspolymer (labeling name) (INCI: Dimethicone/Phenyl Vinyl Dimethicone Crosspolymer) and 85% diphenylsiloxy phenyl trimethicone (labeling name) (INCI: Diphenylsiloxy Phenyl Trimethicone), produced by Shin-Etsu Chemical Co., Ltd.
(Note 2)
Polyglyceryl-3 polydimethylsiloxyethyl dimethicone (labeling name) (INCI: Polyglyceryl-3 Polydimethylsiloxyethyl Dimethicone) produced by Shin-Etsu Chemical Co., Ltd.

The obtained W/O cream was excellent in spreading property and richness and had fresh feeling and good stability over time.

Example 9

W/O Cream

<Preparation of Cosmetic>

A: Components 1 to 6 were uniformly mixed.

B: Components 7 to 13 were uniformly mixed.

C: The mixture of B was added to the mixture of A, and they were emulsified to obtain a W/O cream.

| | Components | Mass % |
|---|---|---|
| 1. | KSG-840 (Note 1) | 3 |
| 2. | KSG-44 (Note 2) | 3 |
| 3. | Composition of Preparation Example 8 | 0.5 |
| 4. | Squalane | 6 |
| 5. | Jojoba seed oil | 14 |
| 6. | KSP-100 (Note 3) | 1 |
| 7. | BG | 5 |
| 8. | Glycerin | 3 |
| 9. | Sodium hyaluronate (1% aqueous solution) | 1.5 |
| 10. | Sodium Citrate | 0.2 |
| 11. | Sodium Chloride | 0.5 |
| 12. | Ethylhexylglycerin | 0.1 |
| 13. | Water | Balance |
| Total | | 100 |

(Note 1)
Mixture of 30% (lauryl dimethicone/polyglycerin-3) crosspolymer (labeling name) (INCI: Lauryl Dimethicone/Polyglycerin-3 Crosspolymer) and 70% squalane (labeling name) (INCI: Squalane), produced by Shin-Etsu Chemical Co., Ltd.
(Note 2)
Mixture of 30% (vinyl dimethicone/lauryl dimethicone) crosspolymer (labeling name) (INCI: Vinyl Dimethicone/Lauryl Dimethicone Crosspolymer) and 70% squalane (labeling name) (INCI: Squalane), produced by Shin-Etsu Chemical Co., Ltd.
(Note 3)
(Vinyl dimethicone/methicone silsesquioxane) crosspolymer (labeling name) (INCI: Vinyl Dimethicone/Methicone Silsesquioxane Crosspolymer) produced by Shin-Etsu Chemical Co., Ltd.

The obtained W/O cream was excellent in spreading property and richness and had fresh feeling and good stability over time.

Example 10

Concealer

<Preparation of Cosmetic>

Components 1 to 9 were mixed to obtain a concealer.

| | Components | Mass % |
|---|---|---|
| 1. | KSP-101 (Note 1) | 18 |
| 2. | KSP-300 (Note 2) | 4 |
| 3. | KSG-19 (Note 3) | 6 |
| 4. | Composition of Preparation Example 16 | 0.5 |
| 5. | KF-56A | 7 |
| 6. | KF-96A-6cs | Balance |
| 7. | KF-96L-2cs | 18 |
| 8. | Silicone-treated microparticulate zinc oxide | 5 |
| 9. | Titanium oxide | 0.3 |
| | Total | 100 |

(Note 1)

(Vinyl dimethicone/methicone silsesquioxane) crosspolymer (labeling name) (INCI: Vinyl Dimethicone/Methicone Silsesquioxane Crosspolymer) produced by Shin-Etsu Chemical Co., Ltd.

(Note 2)

(Diphenyl dimethicone/vinyl diphenyl dimethicone/silsesquioxane) crosspolymer (labeling name) (INCI: Diphenyl Dimethicone/Vinyl Diphenyl Dimethicone/Silsesquioxane Crosspolymer) produced by Shin-Etsu Chemical Co., Ltd.

(Note 3)

Mixture of 15% (dimethicone/vinyl dimethicone) crosspolymer (labeling name) (INCI: Dimethicone/Vinyl Dimethicone Crosspolymer) and 85% dimethicone (labeling name) (INCI: Dimethicone), produced by Shin-Etsu Chemical Co., Ltd.

The obtained concealer was excellent in spreading property and richness and had fresh feeling and good stability over time.

Example 11

O/W Cream

<Preparation of Cosmetic>

A: Components 1 to 4 were uniformly mixed.

B: Components 5 to 13 were uniformly mixed.

C: The mixture of B was added to the mixture of A, and they were emulsified to obtain an O/W cream.

| | Components | Mass % |
|---|---|---|
| 1. | KSG-048Z (Note 1) | 5 |
| 2. | KSG-19 (Note 2) | 10 |
| 3. | Composition of Preparation Example 13 | 0.5 |
| 4. | KF-96A-6cs | 10 |
| 5. | Polysorbate 60 | 1 |
| 6. | BG | 5 |
| 7. | Pentylene glycol | 2 |
| 8. | Xylitol | 2 |
| 9. | SIMULGEL NS (Note 3) | 1 |
| 10. | Carboxyvinyl polymer | 0.2 |
| 11. | Sodium hydroxide | Appropriate amount |
| 12. | Phenoxy ethanol | 0.3 |
| 13. | Water | Balance |
| | Total | 100 |

-continued (Note 1)

Mixture of 20% (lauryl polydimethylsiloxyethyl dimethicone/bis-vinyldimethicone) crosspolymer (labeling name) (INCI: Lauryl Polydimethylsiloxyethyl Dimethicone/Bis-Vinyldimethicone Crosspolymer) and 80% dimethicone (labeling name) (INCI: Dimethicone), produced by Shin-Etsu Chemical Co., Ltd.

(Note 2)

Mixture of 15% (dimethicone/vinyl dimethicone) crosspolymer (labeling name) (INCI: Dimethicone/Vinyl Dimethicone Crosspolymer) and 85% dimethicone (labeling name) (INCI: Dimethicone), produced by Shin-Etsu Chemical Co., Ltd.

(Note 3)

(Hydroxyethyl acrylate/Na acryloyldimethyl taurine) copolymer composition produced by SEPPIC)

The obtained O/W cream was excellent in spreading property and richness and had fresh feeling and good stability over time.

Example 12

O/W Sunscreen Cream

<Preparation of Cosmetic>

A: Components 1 to 8 were heated to 80° C. and uniformly mixed.

B: Components 9 to 14 were heated to 80° C. and uniformly mixed.

C: The mixture of B was added to the mixture of A, and Component 15 was uniformly mixed thereto to obtain a sunscreen.

| | Components | Mass % |
|---|---|---|
| 1. | Xanthan gum | 0.2 |
| 2. | BG | 8 |
| 3. | Caprylhydroxamic acid | 0.1 |
| 4. | SEPIGEL 305 (Note 1) | 2 |
| 5. | Polyoxyethylene (60) cured castor oil | 1 |
| 6. | KF-6043 (Note 2) | 0.5 |
| 7. | Allantoin | 0.2 |
| 8. | Purified water | Balance |
| 9. | Composition of Preparation Example 12 | 0.3 |
| 10. | KF-56A | 3 |
| 11. | KSG-016F (Note 3) | 1.5 |
| 12. | Cetanol | 2 |
| 13. | Ethylhexyl methoxycinnamate | 5 |
| 14. | Alkylsilane-treated microparticulate zinc oxide | 2 |
| 15. | Ethanol | 10 |
| | Total | 100 |

(Note 1)

(Polyacrylamide composition) produced by SEPPIC (Note 2)

PEG-10 dimethicone (labeling name) (INCI: PEG-10 Dimethicone) produced by Shin-Etsu Chemical Co., Ltd.

(Note 3)

Mixture of 25% (dimethicone/vinyl dimethicone) crosspolymer (labeling name) (INCI: Dimethicone/Vinyl Dimethicone Crosspolymer) and 75% dimethicone (labeling name) (INCI: Dimethicone), produced by Shin-Etsu Chemical Co., Ltd.

The obtained O/W sunscreen cream was excellent in spreading property and richness and had fresh feeling and good stability over time.

Example 13

W/O Sunscreen Cream

<Preparation of Cosmetic>

A: Components 1 to 11 were uniformly mixed.

B: Components 14 to 18 were uniformly mixed.

C: The mixture of B was added to the mixture of A, and they were emulsified. Components 12 and 13 were uniformly mixed thereto to obtain a W/O cream.

| | Components | Mass % |
|---|---|---|
| 1. | Composition of Preparation Example 1 | 2 |
| 2. | KSG-18A (Note 1) | 2 |
| 3. | KF-6048 (Note 2) | 1.5 |
| 4. | Dicaprylyl carbonate | 8 |
| 5. | Isononyl isononanoate | 3 |
| 6. | Disteardimonium hectorite | 0.8 |
| 7. | Stearyl glycyrrhetinate | 0.2 |
| 8. | Ethylhexyl methoxycinnamate | 7 |
| 9. | Diethylamino hydroxybenzoyl hexyl benzoate | 2 |
| 10. | Cetyl ethylhexanoate | 5 |
| 11. | KSP-300 (Note 3) | 2 |
| 12. | SPD-T7 (Note 4) | 12 |
| 13. | SPD-Z5 (Note 5) | 12 |
| 14. | Pentylene glycol | 2 |
| 15. | Ethanol | 6 |
| 16. | Sodium Citrate | 0.2 |
| 17. | Sodium Chloride | 0.5 |
| 18. | Water | Balance |
| | Total | 100 |

(Note 1)
Mixture of 15% (dimethicone/phenyl vinyl dimethicone) crosspolymer (labeling name) (INCI: Dimethicone/Phenyl Vinyl Dimethicone Crosspolymer) and 85% diphenylsiloxy phenyl trimethicone (labeling name) (INCI: Diphenylsiloxy Phenyl Trimethicone), produced by Shin-Etsu Chemical Co., Ltd.
(Note 2)
Cetyl PEG/PPG-10/1 dimethicone (labeling name) (INCI: Cetyl PEG/PPG-10/1 Dimethicone) produced by Shin-Etsu Chemical Co., Ltd.
(Note 3)
(Diphenyl dimethicone/vinyl diphenyl dimethicone/silsesquioxane) crosspolymer (labeling name) (INCI: Diphenyl Dimethicone/Vinyl Diphenyl Dimethicone/Silsesquioxane Crosspolymer) produced by Shin-Etsu Chemical Co., Ltd.
(Note 4)
Dispersion of 40% titanium dioxide (labeling name) (INCI: Titanium Dioxide) produced by Shin-Etsu Chemical Co., Ltd.
(Note 5)
Dispersion of 60% Zinc oxide (labeling name) (INCI: Zinc Oxide) produced by Shin-Etsu Chemical Co., Ltd.

The obtained W/O sunscreen cream was excellent in spreading property and richness and had fresh feeling and good stability over time.

Example 14

W/O Shaking Sunscreen

<Preparation of Cosmetic>

A: Components 11 to 14 were dispersed with a homomixer, and components 1 to 10 were added and uniformly mixed.

B: Components 15 to 21 were uniformly mixed.

C: The mixture of B was added to the mixture of A, and they were emulsified to obtain a W/O shaking sunscreen.

| | Components | Mass % |
|---|---|---|
| 1. | Composition of Preparation Example 7 | 0.5 |
| 2. | KSG-18A (Note 1) | 3 |
| 3. | KF-6038 (Note 2) | 2 |
| 4. | Coco-caprylate/caprate | 5.5 |
| 5. | Triethylhexanoin | 5 |
| 6. | Homosalate | 5 |
| 7. | Ethylhexyl salicylate | 5 |
| 8. | Bisethylhexyloxyphenol methoxyphenyltriazine | 2.5 |
| 9. | Octocrylene | 2 |
| 10. | KMP-590 (Note 3) | 0.5 |
| 11. | KF-96L-2cs | 27 |
| 12. | KF-6105 (Note 4) | 1.5 |
| 13. | Metal soap-treated microparticulate titanium oxide | 4.5 |
| 14. | Alkylsilane-treated microparticulate zinc oxide | 12 |
| 15. | BG | 3 |
| 16. | Ethanol | 6 |
| 17 | Tranexamic acid | 2 |
| 18. | Glyceryl caprylate | 0.1 |
| 19. | Sodium Citrate | 0.2 |
| 20. | Sodium Chloride | 0.5 |
| 21. | Water | Balance |
| | Total | 100 |

(Note 1)
Mixture of 15% (dimethicone/phenyl vinyl dimethicone) crosspolymer (labeling name) (INCI: Dimethicone/Phenyl Vinyl Dimethicone Crosspolymer) and 85% diphenylsiloxy phenyl trimethicone (labeling name) (INCI: Diphenylsiloxy Phenyl Trimethicone), produced by Shin-Etsu Chemical Co., Ltd.
(Note 2)
Lauryl PEG-9 polydimethylsiloxyethyl dimethicone (labeling name) (INCI: Lauryl PEG-9 Polydimethylsiloxyethyl Dimethicone) produced by Shin-Etsu Chemical Co., Ltd.
(Note 3)
Polymethylsilsesquioxane (labeling name) (INCI: Polymethylsilsesquioxane) produced by Shin-Etsu Chemical Co., Ltd.
(Note 4)
Lauryl polyglyceryl-3 polydimethylsiloxyethyl dimethicone (labeling name) (INCI: Lauryl Polyglyceryl-3 Polydimethylsiloxyethyl Dimethicone) produced by Shin-Etsu Chemical Co., Ltd.

The obtained W/O shaking sunscreen was excellent in spreading property and richness and had good stability over time.

Example 15

Shaking Foundation

<Preparation of Cosmetic>

A: Components 12 to 18 were dispersed by using a three-roll mill.

B: Components 1 to 11 were uniformly mixed.

C: The mixture of B was added to the mixture of A, and they are mixed uniformly to obtain a shaking foundation.

| | Components | Mass % |
|---|---|---|
| 1. | Composition of Preparation Example 3 | 0.5 |
| 2. | KSG-18A (Note 1) | 3 |
| 3. | KF-6038 (Note 2) | 2 |
| 4. | KSP-441 (Note 3) | 8 |
| 5. | KP-550 (Note 4) | 1.5 |
| 6. | Disteardimonium hectorite | 1.5 |
| 7. | Silica dimethyl silylate | 1.6 |
| 8. | Ethylhexyl methoxycinnamate | 5 |
| 9. | Triethylhexanoin | 6 |
| 10. | Isododecane | 10 |
| 11. | KF-96L-2cs | Balance |
| 12. | KF-96A-6cs | 6 |
| 13. | KF-6106 (Note 5) | 0.75 |
| 14. | Metal soap-treated microparticulate titanium oxide | 3 |
| 15. | KTP-09W (Note 6) | 8.5 |
| 16. | KTP-09Y (Note 7) | 0.9 |

-continued

| | Components | Mass % |
|---|---|---|
| 17. | KTP-09R (Note 7) | 0.5 |
| 18. | KTP-09B (Note 7) | 0.1 |
| 19. | Ethanol | 6 |
| | Total | 100 |

(Note 1)

Mixture of 15% (dimethicone/phenyl vinyl dimethicone) crosspolymer (labeling name) (INCI: Dimethicone/Phenyl Vinyl Dimethicone Crosspolymer) and 85% diphenylsiloxy phenyl trimethicone (labeling name) (INCI: Diphenylsiloxy Phenyl Trimethicone), produced by Shin-Etsu Chemical Co., Ltd.

(Note 2)

Lauryl PEG-9 polydimethylsiloxyethyl dimethicone (labeling name) (INCI: Lauryl PEG-9 Polydimethylsiloxyethyl Dimethicone) produced by Shin-Etsu Chemical Co., Ltd.

(Note 3)

Polysilicone-22 (labeling name) (INCI: Polysilicone-22) produced by Shin-Etsu Chemical Co., Ltd.

(Note 4)

(Acrylates/dimethicone) copolymer (labeling name) (INCI: Acrylates/Dimethicone Copolymer) produced by Shin-Etsu Chemical Co., Ltd.

(Note 5)

Polyglyceryl-3 polydimethylsiloxyethyl dimethicone (labeling name) (INCI: Polyglyceryl-3 Polydimethylsiloxyethyl Dimethicone) produced by Shin-Etsu Chemical Co., Ltd.

(Note 6)

Titanium dioxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

(Note 7)

Iron oxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

The obtained shaking foundation was excellent in spreading property and richness and had good stability over time.

Example 16

W/O Liquid Foundation

<Preparation of Cosmetic>

A: Components 9 to 14 were dispersed by using a three-roll mill.

B: Components 1 to 8 were uniformly mixed.

C: Components 15 to 18 were uniformly mixed.

D: The mixture of C was added to the mixture of B, and they were emulsified. The mixture of A was uniformly mixed thereto to obtain a W/O liquid foundation.

| | Components | Mass % |
|---|---|---|
| 1. | Composition of Preparation Example 10 | 2 |
| 2. | KSG-15 (Note 1) | 2 |
| 3. | KF-6017 (Note 2) | 2 |
| 4. | KF-56A (Note 3) | 5 |
| 5. | Disteardimonium hectorite | 1 |
| 6. | KF-995 | 17.1 |
| 7. | KF-96A-6cs | 5 |
| 8. | KSP-100 (Note 4) | 2 |
| 9. | Ethylhexyl palmitate | 5 |
| 10. | KP-578 (Note 5) | 0.2 |
| 11. | KTP-09W (Note 6) | 15 |
| 12. | KTP-09Y (Note 7) | 0.9 |
| 13. | KTP-09R (Note 7) | 0.5 |
| 14. | KTP-09B (Note 7) | 0.1 |

-continued

| | Components | Mass % |
|---|---|---|
| 15. | BG | 5 |
| 16. | Sodium Citrate | 0.2 |
| 17. | Sodium Chloride | 0.5 |
| 18. | Water | Balance |
| | Total | 100 |

(Note 1)

Mixture of 7% (dimethicone/vinyl dimethicone) crosspolymer (labeling name) (INCI: Dimethicone/Vinyl Dimethicone Crosspolymer) and 93% cyclopentasiloxane (labeling name) (INCI: Cyclopentasiloxane), produced by Shin-Etsu Chemical Co., Ltd.

(Note 2)

PEG-10 dimethicone (labeling name) (INCI: PEG-10 Dimethicone) produced by Shin-Etsu Chemical Co., Ltd.

(Note 3)

Diphenylsiloxy phenyl trimethicone (labeling name) (INCI: Diphenylsiloxy Phenyl Trimethicone) produced by Shin-Etsu Chemical Co., Ltd.

(Note 4)

(Vinyl dimethicone/methicone silsesquioxane) crosspolymer (labeling name) (INCI: Vinyl Dimethicone/Methicone Silsesquioxane Crosspolymer) produced by Shin-Etsu Chemical Co., Ltd.

(Note 5)

(Acrylates/ethylhexyl acrylate/dimethicone methacrylate) copolymer (labeling name) (INCI: Acrylates/Ethylhexyl Acrylate/Dimethicone Methacrylate Copolymer) produced by Shin-Etsu Chemical Co., Ltd.

(Note 6)

Titanium dioxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

(Note 7)

Iron oxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

The obtained W/O foundation was excellent in spreading property and richness and had good stability over time.

Example 17

W/O Liquid Foundation

<Preparation of Cosmetic>

A: Components 8 to 14 were dispersed by using a three-roll mill.

B: Components 1 to 7 were uniformly mixed.

C: Components 15 to 18 were uniformly mixed.

D: The mixture of C was added to the mixture of B, and they were emulsified. The mixture of A was uniformly mixed thereto to obtain a W/O liquid foundation.

| | Components | Mass % |
|---|---|---|
| 1. | KSG-360Z (Note 1) | 3 |
| 2. | KSG-19 (Note 2) | 5 |
| 3. | KF-6028 (Note 3) | 3 |
| 4. | KF-96L-2cs | 24.8 |
| 5. | Disteardimonium hectorite | 1.2 |
| 6. | PG dicaprylate | 5 |
| 7. | KF-7312L (Note 4) | 1.5 |
| 8. | Cetyl ethylhexanoate | 6 |
| 9. | Composition of Preparation Example 3 | 0.5 |
| 10. | Metal soap-treated microparticulate titanium oxide | 5 |
| 11. | KF-9901 (Note 5) -treated titanium oxide | 8.5 |
| 12. | KF-9901 (Note 5) -treated yellow iron oxide | 0.9 |
| 13. | KF-9901 (Note 5) -treated red iron oxide | 0.5 |
| 14. | KF-9901 (Note 5) -treated black iron oxide | 0.1 |

-continued

| Components | Mass % |
|---|---|
| 15. DPG | 5 |
| 16. Sodium Citrate | 0.2 |
| 17. Sodium Chloride | 1 |
| 18. Water | Balance |
| Total | 100 |

(Note 1)

Mixture of 35% (PEG-15/lauryl polydimethylsiloxyethyl dimethicone) crosspolymer (labeling name) (INCI: PEG-15/Lauryl Polydimethylsiloxyethyl Dimethicone Crosspolymer) and 93% dimethicone (labeling name) (INCI: Dimethicone), produced by Shin-Etsu Chemical Co., Ltd.

(Note 2)

Mixture of 15% (dimethicone/vinyl dimethicone) crosspolymer (labeling name) (INCI: Dimethicone/Vinyl Dimethicone Crosspolymer) and 85% dimethicone (labeling name) (INCI: Dimethicone), produced by Shin-Etsu Chemical Co., Ltd.

(Note 3)

PEG-9 polydimethylsiloxyethyl dimethicone (labeling name) (INCI: PEG-9 Polydimethylsiloxyethyl Dimethicone) produced by Shin-Etsu Chemical Co., Ltd.

(Note 4)

Trimethylsiloxysilicate (labeling name) (INCI: Trimethylsiloxysilicate) produced by Shin-Etsu Chemical Co., Ltd.

(Note 5)

Hydrogen dimethicone (labeling name) (INCI: Hydrogen Dimethicone) produced by Shin-Etsu Chemical Co., Ltd.

The obtained W/O foundation was excellent in spreading property and richness and had good stability over time.

Example 18

BB Cream

<Preparation of Cosmetic>

A: Components 12 to 17 were dispersed by using a three-roll mill.

B: Components 1 to 11 were uniformly mixed.

C: Components 18 to 21 were uniformly mixed.

D: The mixture of C was added to the mixture of B, the mixture of A was uniformly mixed thereto to obtain a BB cream.

| Components | Mass % |
|---|---|
| 1. Composition of Preparation Example 3 | 3 |
| 2. KSG-42A (Note 1) | 5 |
| 3. KF-6048 (Note 2) | 3 |
| 4. Disteardimonium hectorite | 1 |
| 5. Isododecane | 12 |
| 6. Hexyl laurate | 5 |
| 7. t-butyl methoxydibenzoylmethane | 3 |
| 8. Homosalate | 8 |
| 9. Octocrylene | 5 |
| 10. Ethylhexyl salicylate | 5 |
| 11. Bisethylhexyloxyphenol methoxyphenyltriazine | 1.5 |
| 12. Isotridecyl isononanoate | 2 |
| 13. KF-6105 | 0.2 |
| 14. AES-3083 (Note 3) -treated titanium dioxide | 6 |
| 15. AES-3083 (Note 3) -treated yellow iron oxide | 0.8 |
| 16. AES-3083 (Note 3) -treated red iron oxide | 0.4 |
| 17. AES-3083 (Note 3) -treated black iron oxide | 0.1 |
| 18. BG | 5 |
| 19. Sodium Citrate | 0.2 |
| 20. Sodium Chloride | 1 |
| 21. Water | Balance |
| Total | 100 |

(Note 1)

Mixture of 20% (vinyl dimethicone/lauryl dimethicone) crosspolymer (labeling name) (INCI: Vinyl Dimethicone/Lauryl Dimethicone Crosspolymer) and 80% isododecane (labeling name) (INCI: Isododecane), produced by Shin-Etsu Chemical Co., Ltd.

(Note 2)

Cetyl PEG/PPG-10/1 dimethicone (labeling name) (INCI: Cetyl PEG/PPG-10/1 Dimethicone) produced by Shin-Etsu Chemical Co., Ltd.

(Note 3)

Triethoxycaprylylsilane (labeling name) (INCI: Triethoxycaprylylsilane) produced by Shin-Etsu Chemical Co., Ltd.

The obtained BB cream was excellent in spreading property and richness and had good stability over time.

Example 19

Solid Foundation

<Preparation of Cosmetic>

A: Components 1 to 12 were dispersed with a homomixer, and Component 13 was added thereto and heated to 95° C.

B: Components 14 to 20 were uniformly mixed at 85° C.

C: The mixture of A was added to the mixture of B, and they were emulsified. The obtained emulsion was added to a vessel and cooled to obtain a solid foundation.

| Components | Mass % |
|---|---|
| 1. KSG-240 (Note 1) | 3 |
| 2. Composition of Preparation Example 3 | 0.3 |
| 3. Ethylhexyl methoxycinnamate | 7.5 |
| 4. Octocrylene | 2 |
| 5. Diethylamino hydroxybenzoyl hexyl benzoate | 2.5 |
| 6. KF-56A (Note 2) | 6 |
| 7. KF-6105 | 0.3 |
| 8. Alkylsilane-treated microparticulate zinc oxide | 4 |
| 9. KTP-09W (Note 3) | 5 |
| 10. KTP-09Y (Note 4) | 0.6 |
| 11. KTP-09R (Note 4) | 0.3 |
| 12. KTP-09B (Note 4) | 0.1 |
| 13. Ceresine | 2.4 |
| 14. Phenoxy ethanol | 0.2 |
| 15. PCA-Na | 1 |
| 16. Glycerin | 4 |
| 17. BG | 8 |
| 18. Sodium Citrate | 0.2 |
| 19. Sodium Chloride | 1 |
| 20. Water | Balance |
| Total | 100 |

(Note 1)

Mixture of 20% dimethicone/(PEG-10/15) crosspolymer (labeling name) (INCI: Dimethicone/PEG-10/15 crosspolymer) and 80% cyclopentasiloxane (labeling name) (INCI: Cyclopentasiloxane), produced by Shin-Etsu Chemical Co., Ltd.

(Note 2)

Diphenylsiloxy phenyl trimethicone (labeling name) (INCI: Diphenylsiloxy Phenyl Trimethicone) produced by Shin-Etsu Chemical Co., Ltd.

(Note 3)

Titanium dioxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

(Note 4)

Iron oxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

The obtained solid foundation was excellent in spreading property and richness and had fresh feeling and good stability over time.

Example 20

Mascara

<Preparation of Cosmetic>

A: Components 1 to 9 were dispersed with a disperser, and Components 10 to 12 were added and heated to 95° C.

B: The mixture A was cooled to obtain a mascara.

| Components | Mass % |
|---|---|
| 1. TSPL-30-ID (Note 1) | 10 |
| 2. Isododecane | Balance |
| 3. Disteardimonium hectorite | 5 |
| 4. KP-574 (Note 2) -treated black iron oxide | 5 |
| 5. KP-574 (Note 2) -treated talc | 5 |
| 6. KMP-590 | 5 |
| 7. Composition of Preparation Example 10 | 1.2 |

-continued

| | Components | Mass % |
|---|---|---|
| 8. | Propylene carbonate | 1.6 |
| 9. | Phenoxy ethanol | 0.2 |
| 10. | Dextrin palmitate | 2 |
| 11. | Synthetic wax | 6 |
| 12. | Paraffin wax | 6 |
| | Total | 100 |

(Note 1)
Trimethylsiloxysilylcarbamoyl pullulan (labeling name) (INCI: Trimethylsiloxysilylcarbamoyl Pullulan) produced by Shin-Etsu Chemical Co., Ltd.
(Note 2)
(Acrylates/tridecyl acrylate/triethoxysilylpropyl methacrylate/dimethicone methacrylate) copolymer (labeling name) (INCI: Acrylates/Tridecyl Acrylate/Triethoxysilylpropyl Methacrylate/Dimethicone Methacrylate Copolymer) produced by Shin-Etsu Chemical Co., Ltd.

The obtained mascara was excellent in spreading property and richness and had good oil resistance.

Example 21

Lipstick

<Preparation of Cosmetic>

A: Components 9 to 16 were dispersed with a roll mill.

B: Components 1 to 8 were heated and uniformly mixed at 95° C.

C: The mixture of A, the mixture of B, and Components 17 and 18 were uniformed mixed and heated to 85° C.

D: The mixture of C was added to a stick vessel to obtain a lipstick.

| | Components | Mass % |
|---|---|---|
| 1. | Polyethylene | 7 |
| 2. | Microcrystalline wax | 3 |
| 3. | KP-561P (Note 1) | 10.5 |
| 4. | Triethylhexanoin | 14 |
| 5. | Neopentyl glycol diethylhexanoate | 14 |
| 6. | Neopentyl glycol dicaprate | 8 |
| 7. | Hydrogenated polyisobutene | Balance |
| 8. | KF-54HV (Note 2) | 7.5 |
| 9. | Sericite | 0.7 |
| 10. | Red No. 201 | Appropriate |
| 11. | Red No. 202 | Appropriate |
| 12. | Yellow No. 4 | Appropriate |
| 13. | KTP-09W (Note 3) | 2.7 |
| 14. | KTP-09B (Note 4) | Appropriate |
| 15. | KTP-09R (Note 4) | Appropriate |
| 16. | Polyglyceryl-2 triisostearate | 4 |
| 17. | Mica | 6 |
| 18. | Composition of Preparation Example 11 | 1 |
| | Total | 100 |

(Note 1)
(Acrylates/stearyl acrylate/dimethicone) methacrylate copolymer (labeling name) (INCI: Acrylates/Stearyl Acrylate/Dimethicone Methacrylate Copolymer) produced by Shin-Etsu Chemical Co., Ltd.
(Note 2)
Diphenyl dimethicone (labeling name) (INCI: Diphenyl Dimethicone) produced by Shin-Etsu Chemical Co., Ltd.
(Note 3)
Titanium dioxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.
(Note 4)
Iron oxide treated with triethoxysilylethyl polydimethylsiloxyethyl hexyl dimethicone (labeling name) (INCI: Triethoxysilylethyl Polydimethylsiloxyethyl Hexyl Dimethicone) produced by Shin-Etsu Chemical Co., Ltd.

The obtained lipstick was excellent in applicability and richness and had good adhesion resistance.

Example 22

Out-Bath Hair Treatment

<Preparation of Cosmetic>

A: Components 1 to 4 were uniformly mixed.

B: Components 6 to 11 were uniformly mixed.

C: The mixture of B was added to the mixture of A, they were emulsified, and Component 5 was added thereto to obtain an out-bath treatment.

| | Components | Mass % |
|---|---|---|
| 1. | Composition of Preparation Example 3 | 3 |
| 2. | KSG-19 (Note 2) | 1 |
| 3. | KF-6017 (Note 3) | 0.2 |
| 4. | KF-96A-6cs | 8.5 |
| 5. | Flavor | Appropriate |
| 6 | Dipropylene glycol | 8 |
| 7. | Ethanol | 5 |
| 8. | Methyl paraoxybenzoate | 0.1 |
| 9. | Sodium citrate | 0.2 |
| 10. | Sodium chloride | 0.5 |
| 11. | Purified water | Balance |
| | Total | 100 |

(Note 1)
Mixture of 15% (dimethicone/vinyl dimethicone) crosspolymer (labeling name) (INCI: Dimethicone/Vinyl Dimethicone Crosspolymer) and 85% dimethicone (labeling name) (INCI: Dimethicone), produced by Shin-Etsu Chemical Co., Ltd.
(Note 2)
PEG-10 dimethicone (labeling name) (INCI: PEG-10 Dimethicone) produced by Shin-Etsu Chemical Co., Ltd.

The obtained out-bath treatment had excellent smoothness and fresh feeling and good stability over time.

The invention claimed is:

1. A crosslinked organic silicon resin represented by the average composition formula (1):

$$(R^1{}_3SiO_{1/2})_{a1}(R^2{}_3SiO_{1/2})_{a2}(R^3{}_3SiO_{1/2})_{a3}(R^1{}_{3-p}(X_{1/2})_pSiO_{1/2})_{a4}(R^1{}_2SiO_{2/2})_b(R^1SiO_{3/2})_c(SiO_{4/2})_d \quad (1)$$

wherein $R^1$ is, independently of each other, unsubstituted or substituted, an alkyl group having 1 to 30 carbon atoms, an aryl group having 6 to 30 carbon atoms, or an aralkyl group having 7 to 30 carbon atoms, $R^2$ is, independently of each other, a polyoxyalkylene-containing group, a polyhydric alcohol-containing hydrocarbon group having two or more hydroxyl groups and/or alkoxy groups, or a group selected from groups for $R^1$, one or more of $R^2$ in each $R^2{}_3SiO_{1/2}$ unit are a polyoxyalkylene-containing group or a polyhydric alcohol-containing hydrocarbon group having two or more hydroxyl groups and/or alkoxy groups, $R^3$ is, independently of each other, an organopolysiloxane-containing group or a group selected from groups for $R^1$, each $R^{33}SiO_{1/2}$ unit has one or more organopolysiloxane-containing group, X is a divalent polyoxyalkylene-containing group represented by the following formula (2) or a divalent group represented by the following formula (3), and some of $R^2$, $R^3$ and X are optionally hydroxyl groups, $$—Y^1—O—(C_2H_4O)_{e1}(C_3H_6O)_{e2}(C_4H_8O)_{e3}—Y^1— \quad (2)$$

wherein e1, e2, and e3 are numbers satisfying the equations $0 \le e1 < 200$, $0 \le e2 < 200$, $0 \le e3 < 200$, and $0 < e1+e2+e3 \le 200$, and $Y^1$ is a hydrocarbon group having 3 to 20 carbon atoms, optionally having an ether bond or an ester bond or both, and $Y^1$ bonds to a silicon atom in the formula (1), $$—Y^1—O—Q^1—Y^1— \quad (3)$$

wherein $Y^1$ is a hydrocarbon group having 3 to 20 carbon atoms, optionally having an ether bond or an ester bond or both, and $Y^1$ bonds to a silicon atom in the formula (1), and $Q^1$ is a polyhydric alcohol-containing hydrocarbon group having 3 to 20 carbon atoms and having two or more hydroxyl groups and/or alkoxy groups, a1, a2, a3, a4, b, c and d are numbers satisfying equations $0<a1\leq400$, $0\leq a2\leq200$, $0\leq a3\leq400$, $0<a4\leq50$, $0\leq b\leq320$, $0\leq c\leq320$, $0<d\leq1000$, and $0.5\leq(a1+a2+a3+a4)/(c+d)\leq1.5$, and p is a number satisfying the equation $1\leq p\leq3$.

2. The crosslinked organic silicon resin according to claim 1, wherein X is a divalent polyoxyalkylene-containing group represented by the formula (2).

3. The crosslinked organic silicon resin according to claim 1, wherein $Q^1$ in the formula (3) has at least one structure represented by $—CH_2CH(OR^4)CH_2O—$, wherein $R^4$ is an unsubstituted or substituted monovalent hydrocarbon group having 1 to 30 carbon atoms or a hydrogen atom.

4. The crosslinked organic silicon resin according to claim 1, wherein the polyoxyalkylene-containing group in the $R^2$ is represented by the following formula (11):

$$—Y^1—O—(C_2H_4O)_{e4}(C_3H_6O)_{e5}(C_4H_8O)_{e6}R^4 \quad (11)$$

wherein $Y^1$ is a hydrocarbon group having 3 to 20 carbon atoms, optionally having an ether bond or an ester bond or both, $R^4$ is an unsubstituted or substituted monovalent hydrocarbon group having 1 to 30 carbon atoms or a hydrogen atom, e4, e5, and e6 are numbers satisfying the equations $0\leq e4<200$, $0\leq e5<200$, $0\leq e6<200$ and $0<e4+e5+e6\leq200$.

5. The crosslinked organic silicon resin according to claim 1, wherein the organopolysiloxane-containing group for $R^3$ is represented by the following general formula (20), (21), (22) or (23):

$$—(CH_2)_2—C_nH_{2n}-(SiOR^1_2)_g—SiR^1_3 \quad (20)$$

$$—(CH_2)_2—C_nH_{2n}-SiR^1_{h1}-(OSiR^1_3)_{3-h1} \quad (21)$$

$$—(CH_2)_2—C_nH_{2n}-SiR^1_{h1}-(OSiR^1_{h2}(OSiR^1_3)_{3-h2})_{3-h1} \quad (22)$$

$$—(CH_2)_2—C_nH_{2n}-SiR^1_{h1}-(OSiR^1_{h2}(OSiR^1_{h3}(OSiR^1_3)_{3-h3})_{3-h2})_{3-h1} \quad (23)$$

wherein $R^1$ is as defined above, n and g are numbers satisfying the equations $0\leq n\leq5$ and $0\leq g\leq500$, and h1, h2 and h3 are, independently of each other, a number of from 0 to 2.

6. The crosslinked organic silicon resin according to claim 1, wherein the polyhydric alcohol-containing hydrocarbon group having two or more hydroxyl groups and/or alkoxy groups is represented by the following general formula (12):

$$—Y^1—O—Q^2 \quad (12)$$

wherein $Y^1$ is a hydrocarbon group having 3 to 20 carbon atoms, optionally having an ether bond or an ester bond or both, $Y^1$ is bonded to the silicon atom in the formula (1), $Q^2$ is a polyhydric alcohol-containing hydrocarbon group having 3 to 20 carbon atoms and having two or more hydroxyl groups and/or alkoxy groups.

7. The crosslinked organic silicon resin according to claim 6, wherein $Q^2$ in the formula (12) has at least one structure represented by $—CH_2CH(OR^4)CH_2OR^4$, wherein $R^4$ is an unsubstituted or substituted monovalent hydrocarbon group having 1 to 30 carbon atoms or a hydrogen atom.

8. The crosslinked organic silicon resin according to claim 1, having a weight-average molecular weight of 3,000 to 1,000,000.

9. The crosslinked organic silicon resin according to claim 1, having an HLB calculated by Griffin's method of 0.1 to 15.

10. The crosslinked organic silicon resin according to claim 1, having a form of liquid, gum or solid at 25° C., wherein one or more of X in the average composition formula (1) have a group represented by the formula (2), a4 in the average composition formula (1) satisfies the equation $0<a4\leq10$, e1, e2 and e3 in the general formula (2) satisfy the equation $0<e1+e2+e3\leq40$, and having an HLB calculated by Griffin's method of 0.1 to 6.0.

11. The crosslinked organic silicon resin according to claim 1, having a form of liquid or gum at 25° C., wherein one or more of X in the average composition formula (1) have a group represented by the formula (2), a3 and a4 in the average composition formula (1) satisfy the equations $1\leq a3\leq100$ and $0<a4\leq10$, e1, e2 and e3 in the general formula (2) satisfy the equation $8<e1+e2+e3\leq40$, and having a HLB calculated by Griffin's method of 0.1 to 6.0.

12. The crosslinked organic silicon resin according to claim 1, having a form of liquid at 25° C., wherein one or more of X in the average composition formula (1) have a group represented by the formula (2), a3 and a4 in the average composition formula (1) satisfy the equations $1\leq a3\leq100$ and $0<a4\leq3.5$, e1, e2, and e3 in the general formula (2) satisfy the equation $8<e1+e2+e3\leq40$, and having a HLB calculated by Griffin's method of 0.1 to 6.0.

13. The crosslinked organic silicon resin according to claim 1, wherein $R^1$ in the average composition formula (1) is an alkyl group having 1 to 12 carbon atoms and the crosslinked organic silicon resin having a weight-average molecular weight of 40,000 to 1,000,000.

14. A cosmetic comprising the crosslinked organic silicon resin according to claim 1.

15. The cosmetic according to claim 14, the cosmetic being an emulsion composition.

16. The cosmetic according to claim 14, the cosmetic being a sunscreen or makeup cosmetic.

17. A method for preparing the crosslinked organic silicon resin according to claim 1, wherein the method comprises a step of subjecting a hydrosilyl group-containing organic silicon resin represented by the average composition formula (26) and one or more terminal alkenyl group-containing compound selected from the groups consisting of compounds represented by the following general formula (24), (25), (27), (28), (29), (30), (31), or (32) to hydrosilylation to obtain the crosslinked organic silicon resin represented by the average composition formula (1), wherein the terminal alkenyl group-containing compound comprises at least one compound represented by the following formula (24), $$(R^1{}_3SiO_{1/2})_{a1}(H_qR^1{}_{3-q}SiO_{1/2})_{a2+a3+a4}(R^1{}_2SiO_{2/2})_b(R^1SiO_{3/2})_c(SiO_{4/2})_d \quad (26)$$

wherein $R^1$, a1, a2, a3, a4, b, c and d are as defined above, and q satisfies the equation $1 \le q \le 3$, $$Y^2—O—(C_2H_4O)_{e1}(C_3H_6O)_{e2}(C_4H_8O)_{e3}—Y^2 \quad (24)$$

wherein $Y^2$ is a hydrocarbon group having 3 to 20 carbon atoms and having a terminal alkenyl group, optionally having an ether bond or an ester bond or both, and e1, e2, and e3 are as defined above, $$Y^2—O—Q^1—Y^2 \quad (25)$$

wherein $Y^2$ is a hydrocarbon group having 3 to 20 carbon atoms and having a terminal alkenyl group, optionally having an ether bond or an ester bond or both, and $Q^1$ is as defined above, $$Y^2—O—(C_2H_4O)_{e4}(C_3H_6O)_{e5}(C_4H_8O)_{e6}R^4 \quad (27)$$

wherein $Y^2$ is a hydrocarbon group having 3 to 20 carbon atoms having a terminal alkenyl group, optionally having an ether bond or an ester bond or both, and $R^4$, e4, e5, and e6 are as defined above, $$Y^2—O—Q^2 \quad (28)$$

wherein $Y^2$ is a hydrocarbon group having 3 to 20 carbon atoms and having a terminal alkenyl group, optionally having an ether bond or an ester bond or both, and $Q^2$ is as defined above, $$CH_2{=}CH—C_nH_{2n}-(SiOR^1{}_2)_g—SiR^1{}_3 \quad (29)$$

$$CH_2{=}CH—C_nH_{2n}-SiR^1{}_{h1}-(OSiR^1{}_3)_{3-h1} \quad (30)$$

$$CH_2{=}CH—C_nH_{2n}-SiR^1{}_{h1}-(OSiR^1{}_{h2}(OSiR^1{}_3)_{3-h2})_{3-h1} \quad (31)$$

$$CH_2{=}CH—C_nH_{2n}-SiR^1{}_{h1}-(OSiR^1{}_{h2}(OSiR^1{}_{h3}(OSiR^1{}_3)_{3-h3})_{3-h2})_{3-h1} \quad (32)$$

wherein $R^1$, n, g, h1, h2, and h3 are as defined above.

18. The method according to claim 17, wherein $Q^1$ in the formula (25) has at least one structure represented by $—CH_2CH(OR^4)CH_2O—$, wherein $R^4$ is an unsubstituted or substituted monovalent hydrocarbon group having 1 to 30 carbon atoms or a hydrogen atom.

19. The method according to claim 17, wherein $Q^2$ in the formula (28) has at least one structure represented by $—CH_2CH(OR^4)CH_2OR^4$, wherein $R^4$ is an unsubstituted or substituted monovalent hydrocarbon group having 1 to 30 carbon atoms or a hydrogen atom.

20. The method according to claim 17, further comprising a step of preparing the hydrosilyl group-containing organic silicon resin represented by the average composition formula (26), wherein the method comprises steps of subjecting a mixture of one or two or more selected from the group consisting of an organic silicon compound represented by the following general formulas (33) and (34), one or two or more selected from the group consisting of hydrosilyl group-containing organic silicon compounds represented by the following general formulas (35) and (36), and one or two or more selected from the group consisting of a hydrolyzable silane represented by the following general formula (37), partially hydrolyzed condensate of the hydrolyzable silane, and a metal salt of the hydrolyzable silane, to hydrolysis in the presence of an acid catalyst, neutralizing the mixture by adding a basic catalyst in an amount greater than the molar equivalent of the acid catalyst and, then, subjecting the mixture to condensate reaction in the presence of a basic catalyst to obtain the hydrosilyl group-containing organic silicon resin represented by the average composition formula (26), $$R^1{}_3SiOSiR^1{}_3 \quad (33)$$

$$R^1{}_3SiX^1 \quad (34)$$

$$H_qR^1{}_{(3-q)}SiOSiR^1{}_{(3-q)}H_q \quad (35)$$

$$H_qR^1{}_{(3-q)}SiX^1 \quad (36)$$

$$SiX^1{}_4 \quad (37)$$

wherein $R^1$ is as defined above, $X^1$ is, independently of each other, a hydrolyzable functional group, and q satisfies the equation $1 \le q \le 3$.

21. The method according to claim 20, wherein the method comprises steps of subjecting a mixture of one or two or more selected from the group consisting of the organic silicon compounds represented by the general formulas (33) and (34) and one or two or more selected from the group consisting of the hydrolyzable silane represented by the general formula (37), partially hydrolyzed condensate of the hydrolyzable silane, and the metal salt of the hydrolyzable silane, to hydrolysis in the presence of an acid catalyst and, then, adding one or two or more selected from the group consisting of the hydrosilyl group-containing organic silicon compounds represented by the general formulas (35) and (36) to obtain the hydrosilyl group-containing organic silicon resin represented by the average composition formula (26).

22. The cosmetic according to claim 15, wherein the cosmetic is a sunscreen or makeup cosmetic.

* * * * *